US011789018B2

(12) United States Patent
Ladisch et al.

(10) Patent No.: US 11,789,018 B2
(45) Date of Patent: *Oct. 17, 2023

(54) RAPID CONCENTRATION, RECOVERY AND DETECTION OF PATHOGENS IN FOOD SAMPLES

(71) Applicant: Purdue Research Foundation, West Lafayette, IN (US)

(72) Inventors: Michael Ralph Ladisch, West Lafayette, IN (US); Eduardo de Aquino Ximenes, West Lafayette, IN (US); Seockmo Ku, West Lafayette, IN (US); Kirk Solon Foster, West Lafayette, IN (US); Thomas Richard Kreke, West Lafayette, IN (US); Xingya (Linda) Liu, West Lafayette, IN (US); James Thomas Jones, Brookston, IN (US); Amanda Deering, West Lafayette, IN (US); Jaycey Hardenstein, West Lafayette, IN (US); Alisha Tungare, West Lafayette, IN (US)

(73) Assignee: Purdue Research Foundation, West Lafayette, IN (US)

(*) Notice: Subject to any disclaimer, the term of this patent is extended or adjusted under 35 U.S.C. 154(b) by 173 days.

This patent is subject to a terminal disclaimer.

(21) Appl. No.: 15/735,273

(22) PCT Filed: Jul. 22, 2016

(86) PCT No.: PCT/US2016/043596
§ 371 (c)(1),
(2) Date: Dec. 11, 2017

(87) PCT Pub. No.: WO2017/015574
PCT Pub. Date: Jan. 26, 2017

(65) Prior Publication Data
US 2018/0180611 A1 Jun. 28, 2018

Related U.S. Application Data

(60) Provisional application No. 62/196,216, filed on Jul. 23, 2015.

(51) Int. Cl.
*G01N 1/40* (2006.01)
*G01N 33/569* (2006.01)
*C12Q 1/10* (2006.01)
*C12Q 1/04* (2006.01)
*G01N 1/28* (2006.01)

(52) U.S. Cl.
CPC ......... *G01N 33/56916* (2013.01); *C12Q 1/04* (2013.01); *C12Q 1/10* (2013.01); *G01N 1/4005* (2013.01); *G01N 1/4044* (2013.01); *G01N 2001/2866* (2013.01); *G01N 2001/4088* (2013.01); *G01N 2333/245* (2013.01); *G01N 2333/255* (2013.01)

(58) Field of Classification Search
CPC .................................................. G01N 1/4005
See application file for complete search history.

(56) References Cited

U.S. PATENT DOCUMENTS

| 5,368,869 A | 11/1994 | Savello et al. |
| 7,547,526 B2 * | 6/2009 | Ladisch ............... G01N 1/4005 435/30 |
| 9,651,551 B2 * | 5/2017 | Ladisch ................... C12Q 1/22 |
| 2015/0293094 A1 * | 10/2015 | Ladisch ................... C12Q 1/22 435/7.35 |

FOREIGN PATENT DOCUMENTS

| WO | 2013/149003 A1 | 10/2013 |
| WO | WO-2013149003 A1 * | 10/2013 ............. B01D 63/02 |

OTHER PUBLICATIONS

Li et al. Rapid sample processing for detection of food-borne pathogens via cross-flow microfiltration. Appl Environ Microbiol. Nov. 2013; 79(22):7048-54. Epub Sep. 6, 2013. (Year: 2013).*
Li B, Hu Z, Elkins CA. Detection of live *Escherichia coli* O157: H7 cells by PMA-qPCR. JoVE (Journal of Visualized Experiments). Feb. 1, 2014(84):e50967 pp. 1-6. (Year: 2014).*
Leskinen et al. Detection of *E. coli* O157: H7 in complex matrices under varying flow parameters with a robotic fluorometric assay system. InFrontiers in Pathogen Detection: From Nanosensors to Systems. Feb. 19, 2009. Proc of SPIE (vol. 7167, pp. 71670J-1 to 71670J-10). (Year: 2009).*
Fernandez-Astorga, A., Hijarrubia, M.J., Lazaro, B. and Barcina, I., 1996. Effect of the pre-treatments for milk samples filtration on direct viable cell counts. Journal of applied bacteriology, 80(5), pp. 511-516. (Year: 1996).*
Van Vliet, K.M., Blouin, V., Brument, N., Agbandje-McKenna, M. and Snyder, R.O., 2008. The role of the adeno-associated virus capsid in gene transfer. In Drug Delivery Systems (pp. 51-91). Humana Press. (Year: 2008).*
Li, X., 2014. Improved detection techniques for foodborne pathogens: Separation techniques using crossflow microfiltration pp. 1-148 (Doctoral dissertation, Purdue University). (Year: 2014).*
Brewster, J. 2009. Large-volume filtration for recovery and concentration of *Escherichia coli* O157:H7 from ground beef. Journal of Rapid Methods and Automation in Microbiology. 17(2):242-256. (Year: 2009).*

(Continued)

*Primary Examiner* — Gary Benzion
*Assistant Examiner* — Olayinka A Oyeyemi
(74) *Attorney, Agent, or Firm* — Brown Rudnick LLP; Adam M. Schoen

(57) ABSTRACT

Methods for rapidly concentrating a food sample for efficient detection of bacteria are disclosed. A microfiltration approach followed by centrifugation was used to concentrate the cells with an enzyme (e.g., a protease) added at the beginning of the process to facilitate more efficient microfiltering. The enzyme was found to have no significant effect on cell viability.

21 Claims, 29 Drawing Sheets

Specification includes a Sequence Listing.

(56) References Cited

OTHER PUBLICATIONS

Wang, D., Wang, Z., He, F., Kinchla, A.J. and Nugen, S.R., 2016. Enzymatic digestion for improved bacteria separation from leafy green vegetables. Journal of food protection, 79(8), pp. 1378-1386. (Year: 2016).*
Bernhardt, M., Pennell, D.R., Almer, L.S. and Schell, R.F., 1991. Detection of bacteria in blood by centrifugation and filtration. Journal of clinical microbiology, 29(3), pp. 422-425. (Year: 1991).*
de Oliveira et al., 2014. Uses of mechanically separated chicken meat for production from protein hydrolysates different proteolytic enzymes. Semina: Ciencias Agrarias, 35(1), pp. 291-302. (Year: 2014).*
Fukushima et al., 2007. Rapid separation and concentration of food-borne pathogens in food samples prior to quantification by viable-cell counting and real-time PCR. Applied and Environmental Microbiology, 73(1), pp. 92-100. (Year: 2007).*
Khan et al., 2014. Enzymatic cleaning of biofouled thin-film composite reverse osmosis (RO) membrane operated in a biofilm membrane reactor. Biofouling, 30(2), pp. 153-167. (Year: 2014).*
Nilsang et al., 2005. Optimization of enzymatic hydrolysis of fish soluble concentrate by commercial proteases. Journal of food Engineering, 70(4), pp. 571-578. (Year: 2005).*
Stevens, K.A. and Jaykus, L.A., 2004. Bacterial separation and concentration from complex sample matrices: a review. Critical reviews in microbiology, 30(1), pp. 7-24. (Year: 2004).*
Hardenstein, Enzyme-Assisted Pathogen Detection Applied to a Microfiltration System for Food Safety, Purdue University, Poster.
Centers for Disease Control and Prevention—Gould, 2013, Surveillance for foodborne disease outbreaks—United States, 1998-2008. MMWR 2013; vol. 62, No. 2: pp. 1-34.
Food Safety and Inspection Services. (2015). Detection, Isolation and Identification of *Escherichia coli* O157:H7 from Meat Products and Carcass and Environmental Sponges. United States Department of Agriculture.
Bio-Rad Solutions, 2013, Food Safety and Quality Diagnostics, Bio Rad Laboratories, Inc.
Braun, 1995, Migration of *Salmonella enteritidis* from the albumen into the egg yolk. International Journal of Food Microbiology, vol. 25: pp. 95-99.
Miyamoto, 1997, *Salmonella enteritidis* Contamination of Eggs from Hens Inoculated by Vaginal, Cloacal and Intravenous Routes. Avian Diseases, vol. 41: pp. 296-303.
Grijspeerdt, 2005, Individual-based modelling of growth and migration of *Salmonella enteritidis* in hens' eggs. International J. Food Microbio., vol. 15: pp. 323-333.
Andreoletti, 2009, Special measures to reduce the risk for consumers through *Salmonella* in table eggs—e.g. cooling of table eggs, The EFSA Journal, vol. 957: pp. 1-29.
Gantois, 2009, Mechanisms of egg contamination by *Salmonella enteritidis*., FEMS Microbiology Reviews, vol. 33: pp. 718-738.
Stevens, 2004, Bacterial Separation and Concentration from Complex Sample Matrices: a Review, Critical Reviews in Microbiology, vol. 30(1): pp. 7-24.
Margot, 2013, Comparison of rapid cultural methods for the detection of *Salmonella* species, International Journal of Food Microbiology, vol. 163: pp. 47-50.
Cheung, 2012, *Salmonella* in food surveillance: PCR, immunoassays, and other rapid detection and quantification methods. Food Research International, vol. 45: pp. 802-808.
Li, 2013, Rapid Sample Processing for Detection of Food-borne Pathogens via Cross-flow Microfiltration, Appl. Environ. Microbiol., vol. 79(22): pp. 7048-7054.
Bell, 2016, Recent and emerging innovations in *Salmonella* detection: a food and environmental perspective, Microb Biotechnol. Vo. 9: pp. 279-292.
Vibbert, 2015, Accelerating sample preparation through enzyme-assisted microfiltration of *Salmonella* in chicken extract, Biotechnol Prog, vol. 31: pp. 1551-1562.
Zadernowska, 2012, Detection of *Salmonella* spp. Presence in Food, *Salmonella*—A Dangerous Foodborne Pathogen, Dr. Barakat S.M. Mahmoud (Ed.) ISBN: 978-953-307-782-2, InTech.
Hoppe, 2010, Examination of egg white proteins and effects of high pressure on select physical and functional properties (thesis). University of Nebraska Lincoln, Food Science and Technology Department, Fall Dec. 2010.
Johnson, 1981, Egg Albumen Proteins Interactions in an Angel Food Cake System, J. Food Science, vol. 46: pp. 1231-1236.
Raeker, 1995, Cake-baking (High-Ratio White Layer) Properties of Egg White, Bovine Blood Plasma, and Their Protein Fractions, Cereal Chem., vol. 72 (3): pp. 299-303.
Lechevalier, 2003, Ovalbumin, Ovotransferrin, Lysozyme: Three Model Proteins for Structural Modifications at the Air-Water Interface, J. of Agric. Food Chem., vol. 51: pp. 6354-6361.
Lechevalier, 2005, Evidence for synergy in the denaturation at the air-water interface of ovalbumin, ovotransferrin and lysozyme in ternary mixture, J.Food Chem., vol. 92: pp. 79-87.
Wang, 2009, Egg yolk protein modification by controlled enzymatic hydrolysis for improved functionalities, International Journal of Food Science and Technology, vol. 44: pp. 763-769.
Ensign, 1966, Characterization of a Small Proteolytic Enzyme Which Lyses Bacterial Cell Walls, J. Bacteriology, vol. 2: pp. 524-534.
Scott, 1980, Lyticase: Endoglucanase and Protease Activities That Act Together in Yeast Cell Lysis, Journal of Bacteriology, vol. 142, No. 2: pp. 414-423.
Kodama, 2007, Effect of Bacillus subtilis spo0A Mutation on Cell Wall Lytic Enzymes and Extracellular Proteases, and Prevention of Cell Lysis, J. Bioscience and Bioengineering, vol. 103: pp. 13-21.
Rice, 2008, Molecular Control of Bacterial Death and Lysis, Microbiol. Mol. biol. Rev.; vol. 72: pp. 85-109.
Salazar, 2007, Enzymatic lysis of microbial cells, Biotechnol Lett, vol. 29: pp. 985-994.
Choi, 2005, Effect of permeate flux and tangential flow on membrane fouling for wastewater treatment, Separation and Purification Technology, vol. 45: pp. 68-78.
Ladisch, 2001, Bioseparations Engineering: Principles, Practice, and Economics (100-106), NY: Wiley Interscience.
Rijpens, 1999, Rapid detection of stressed *Salmonella* spp. in dairy and egg products using immunomagnetic separation and PCR, International Journal of Food Microbiology, vol. 46: pp. 37-44.
Soria, 2012, A comparative study of culture methods and polymerase chain reaction for *Salmonella* detection in egg content, Poultry Science, vol. 91: pp. 2668-2676.
International Preliminary Report on Patentability, Written Opinion and International Search Report for PCT/US2016/043596, 8 pages.
Brewster, 2009, Large-volume filtration for recovery and concentration of *Escherichia coli* O157:H7 from ground beef, Journal of Rapid methods and Autonation in Microbiology, 17(2):242-256.
Li, 2014, Improved detection techniques for foodborne pathogens: Separation techniques using crossflow microfiltration pp. 1-148.
Mexican Office Action issued in Mexican Application No. MX/a/2018/000840, dated Nov. 10, 2021, 6 pages.
Wang, 2016, Enzymatic digestion for improved bacteria separation from leafy green vegetables, Journal of food protection, 79(8):1378-1386.
Berhardt, 1991, Detection of bacteria in blood by centifugation and filtration, Journal of clinical microbiology, 29 (3):422-425.
de Oliveira, 2014, Uses of mechanically separated chicken meat for production from hydrolysates different proteolytic enzymes, Semina: Ciencias Agrarias, 35(1):291-302.
Fukushima, 2007, Rapid separation and concentration of food-borne pathogens in food samples prior to quantification by viable-cell counting and real-time PCR, Applied and Environmental Microbiology, 73(1):92-100.
Khan, 2014, Enzymatic cleaning of biofouled thin-film composite reverse osmosis (RO) membrane operated in a biofilm membrane reactor, Biofouling, 30(2):153-167.

(56) References Cited

OTHER PUBLICATIONS

Nilsang, 2005, Optimization of enzymatic hydrolysis of fish soluble concentrate by commercial proteases, Journal of food Engineering, 70(4):571-578.

* cited by examiner

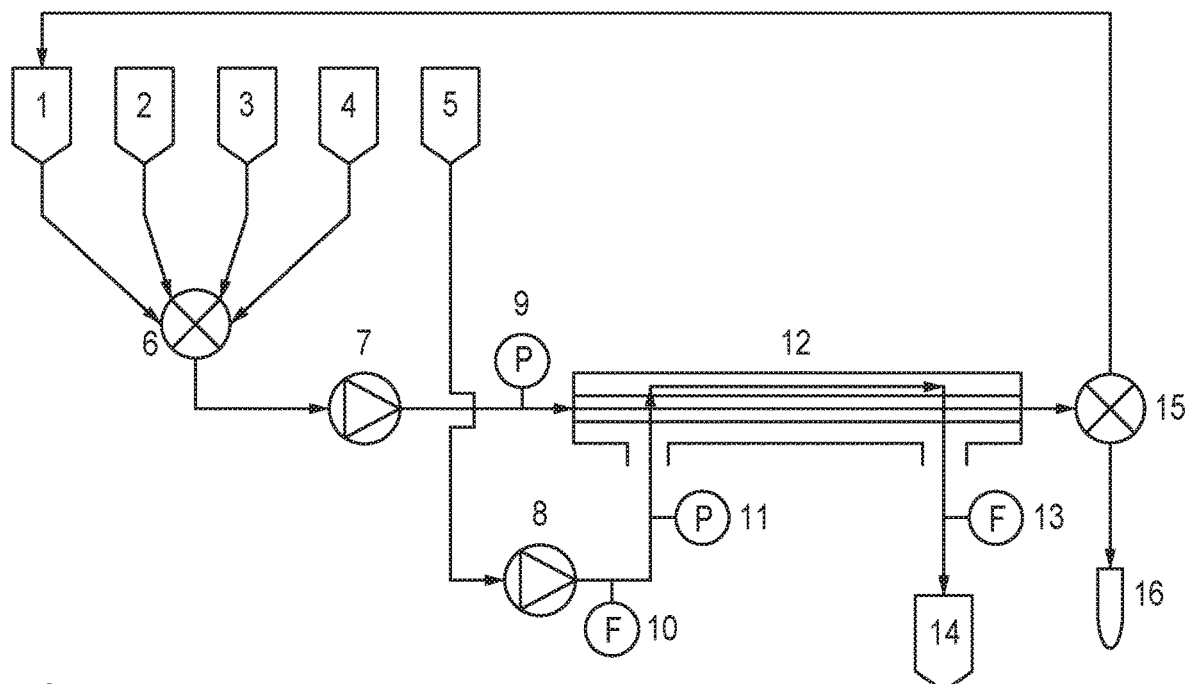

1. Sample reservoir
2. Ethanol reservoir
3. NaOH reservoir
4. Elution buffer reservoir
5. Water reservoir
6. 4-to-1 source select valve
7. Peristaltic pump 1
8. Peristaltic pump 2
9. Pressure transducer 1
10. Flow sensor2
11. Pressure transducer2
12. Membrane module
13. Flow sensor 1
14. Permeate tank
15. Valve
16. Sample collection tube A schematic representation of the Continuous Cell Concentration Device ($C^3D$)

FIG. 6

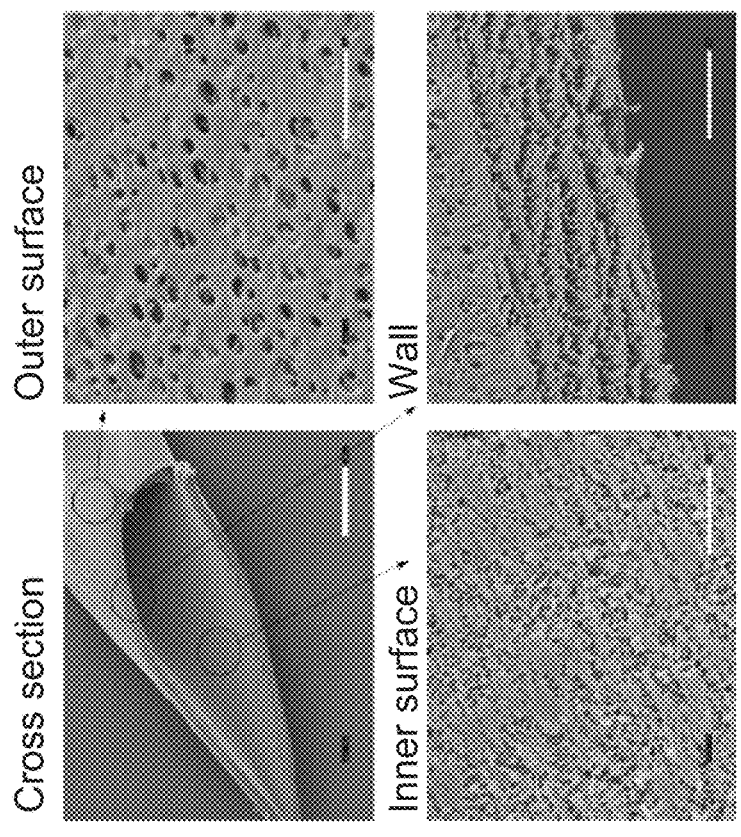
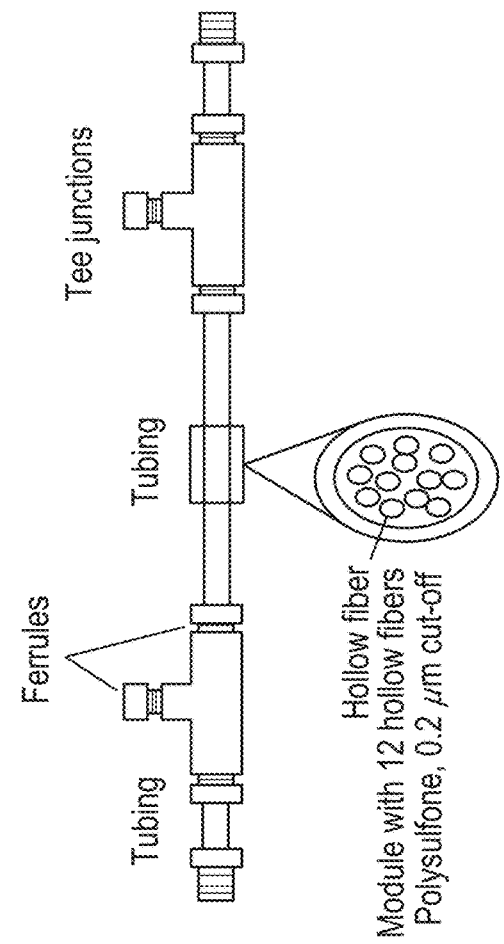
FIG. 30

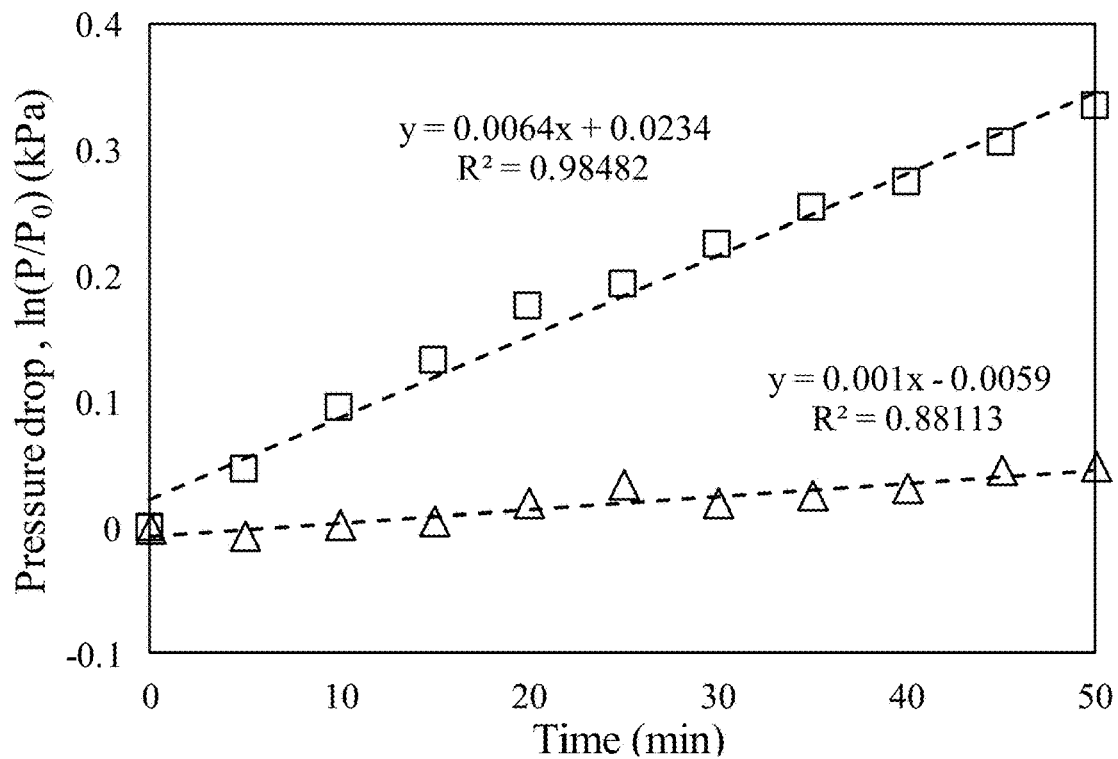
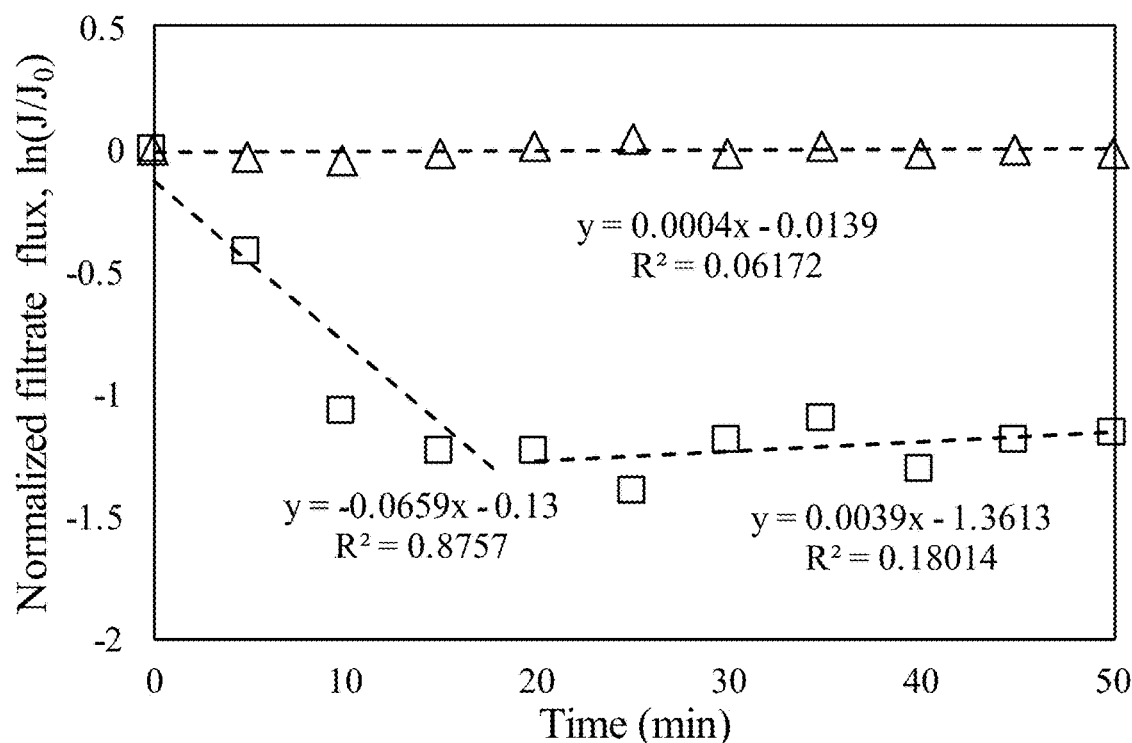
FIG. 41

SEQUENCE LISTING

<160> NUMBER OF SEQ ID NOS: 6

<210> SEQ ID NO 1
<211> LENGTH: 26
<212> TYPE: DNA
<213> ORGANISM: Salmonella enterica

<400> SEQUENCE: 1
gtgaaattat cgccacgttc gggcaa                26

<210> SEQ ID NO 2
<211> LENGTH: 22
<212> TYPE: DNA
<213> ORGANISM: Salmonella enterica

<400> SEQUENCE: 2
tcatcgcacc gtcaaaggaa cc                22

<210> SEQ ID NO 3
<211> LENGTH: 20
<212> TYPE: DNA
<213> ORGANISM: Salmonella enterica

<400> SEQUENCE: 3
ctgccgcagt gttaaggata                20

<210> SEQ ID NO 4
<211> LENGTH: 18
<212> TYPE: DNA
<213> ORGANISM: Salmonella enterica

<400> SEQUENCE: 4
gtcgccttaa tcgcatgg                18

<210> SEQ ID NO 5
<211> LENGTH: 25
<212> TYPE: DNA
<213> ORGANISM: Salmonella enterica

<400> SEQUENCE: 5
actggcgtta tccctttctc tggtg                25

<210> SEQ ID NO 6
<211> LENGTH: 23

```
<212> TYPE: DNA
<213> ORGANISM: Salmonella enterica

<400> SEQUENCE: 6
gttgtcctgc ccctggtaag aga                                              23
```

RAPID CONCENTRATION, RECOVERY AND DETECTION OF PATHOGENS IN FOOD SAMPLES

RELATED APPLICATION

This application is a U.S. National Stage filing of PCT/US2016/043596, filed Jul. 22, 2016, which claims the benefit of and priority to U.S. Provisional No. 62/196,216, filed Jul. 23, 2015, which is incorporated by reference in its entirety.

GOVERNMENT INTEREST

This invention was made with government support under OSQR935-42000-049-00D awarded by the United States Department of Agriculture. The government has certain rights in the invention.

TECHNICAL FIELD

The present invention generally relates to methods for rapid concentration, recovery and detection of pathogens in food products.

BACKGROUND

Foodborne illnesses, caused by various pathogens contaminating the food we eat, affect 1 in 6 Americans each year according to the Centers for Disease Control and Prevention (CDC). More than 250 different foodborne illnesses have been described and their effect can range from discomfort and missed work to serious complications and death. The spread of foodborne illnesses can be prevented through careful monitoring of food by producers and sellers. Unfortunately, this monitoring, using current techniques, can be expensive and time consuming, often taking multiple days to obtain results. The resulting delays between processing and sale of certain foods while awaiting results can be problematic, especially with food items such as meat, fruits, and vegetables.

*Salmonella* provides a good model for understanding the danger of foodborne pathogens as well as the current state of the art in foodborne pathogen detection. The CDC reports about 42,000 *Salmonella* outbreaks annually in the United States. Eggs, poultry, meat, and raw fruits and vegetables may act as possible *Salmonella* reservoirs in the food chain and cause illness when consumed by people.

Recently, *Salmonella* contamination showed significant impacts on the food industry. One such example is a *Salmonella* Enteritidis contamination that led to recall of more than a half billion eggs from Iowa between May and November, 2010. There were 1,939 infections linked to that outbreak (Center for Disease Control and Prevention, 2014b). Internationally, egg contamination has been responsible for 247 cases and 3 deaths in the United Kingdom (Public Health England, 2014), 130 cases in the other European countries (European Food Safety Authority, 2014) and 353 cases in the South Australia since the beginning of 2014 (Government of South Australia, 2014) (Table 1).

TABLE 1

Incidence of *Salmonella* Enteritidis associated with eggs in the U.S. and European countries.

| Country | Date | Reported Case | Organization |
| --- | --- | --- | --- |
| U.K. | August 2014 | 247 (3 deaths) | Public Health England |
| France | August 2014 | 45 | European Food Safety Authority |
| Austria | June 2014 | 61 | European Food Safety Authority |
| Germany | June 2014 | 24 | European Food Safety Authority |
| Australia | April 2014 | 353 | Government of South Australia |
| U.S.A. | May 2010 | 1939 | Center for Disease Control |

Monitoring pathogens such as *Salmonella* in eggs can be particularly important to vaccine manufacturing processes for quality assurance and risk control. In general, *Salmonella* contaminations are more often observed in the albumen (egg whites) than in the yolk. Clavijo, et al., (2006), Identification of genes associated with survival of *Salmonella enterica* Serovar Enteritidis in chicken egg albumen, *Applied and Environmental Microbiology*, 72, 1055-1064 (incorporated herein by reference) reported that *Salmonella* are more adept at thriving in egg albumen compared with other microorganisms because of distinctive genes related their cell wall formation and metabolism. Mechanisms of egg white contamination by *Salmonella* have been described in numerous studies during the last two decades (Braun & Fehlhaber, (1995), Migration of *Salmonella enteritidis* from the albumen into the egg yolk. *International Journal of Food Microbiology* 25, 95-99; Miyamoto T et al., (1997), *Salmonella* Enteritidis contamination of eggs from hens inoculated by vaginal, cloacal and intravenous routes. *Avian Diseases*, 41, 296-303; Grijspeerdt, et al., (2005), Individual-based modelling of growth and migration of *Salmonella enteritidis* in hens' eggs. *International Journal of Food Microbiology*, 15, 323-33; Andreoletti, et al. (2009), Special measures to reduce the risk for consumers through *Salmonella* in table eggs—e.g. cooling of table eggs, *The EFSA Journal*, 957, 1-29., 2009; Gantois, et al, (2009), Mechanisms of egg contamination by *Salmonella* Enteritidis., *FEMS Microbiology Reviews*, 33, 718-38; the contents of each of which are incorporated by reference.

Egg samples are typically enriched for the detection of *Salmonella* using traditional plating methods (Stevens & Jaykus (2004), Bacterial separation and concentration from complex sample matrices: a review, *Critical Reviews in Microbiology*, 30, 1, 7-24, incorporated herein by reference).

Standardized methods are regarded as the "gold standard" of detecting foodborne pathogenic bacteria (such as ISO 6579:2002, 2002) but are often labor intensive and with times up to 7 days (Margot, et al., (2013), Comparison of rapid cultural methods for the detection of *Salmonella* species, *International Journal of Food Microbiology*, 163, 47-50, incorporated herein by reference). At least 3 to 4 days are needed to indicate negative results of *Salmonella* contamination through plating on selective agar plates (Cheung, & Kam (2012), *Salmonella* in food surveillance: PCR, immunoassays, and other rapid detection and quantification methods. *Food Research International*, 45, 802-808, incorporated herein by reference).

In order to reduce time for *Salmonella* detection, rapid methods have been developed that are equivalent to U.S. FDA approved assays for egg safety. These include SDIX RapidChek SELECT™ *Salmonella Enteritidis* Test System; Neogen Reveal *Salmonella Enteritidis* (SE) Test System; Applied Biosystems TaqMan® *Salmonella Enteritidis* Detection Kit and the BAX® System PCR Assay (U.S. Food and Drug Administration, 2014a). These technologies still require a 1 to 2 day enrichment process, delaying results in the time sensitive food industry.

SUMMARY OF THE INVENTION

The invention provides for rapid screening of food or other samples for pathogens such as *Salmonella*. Methods of the invention may be used to identify pathogens such as *Salmonella* from whole food in as little as 7 hours, providing a significant improvement over the processes detailed above. Methods of the invention include sample preparation, treatment, and concentration protocols that allow for recovery and identification of small amounts of pathogen in food (e.g., less than 0.5 CFU/g of *Salmonella* in as little as 7 hours). Methods may include preparation/homogenization of the food sample using, for example a stomacher or a blender to create a sample solution comprising both interior and surface pathogens from the food sample. The food sample may be treated with one or more enzymes such as a protease before filtration and concentration. Enzyme treatment may hydrolyze coagulated proteins and reduce foaming that may occur during sample preparation. By treating the sample prior to filtration, large, filter clogging molecules may be reduced or eliminated, allowing for the use of microfiltration techniques such as the Continuous Cell Concentration Device ($C^3D$) described below. Samples may additionally be subjected to pre-filtration to remove large particles before microfiltration and concentration. The resulting concentrate may then be assayed for contamination by known methods such as polymerase chain reaction (PCR)-based detection techniques or plating on selective media for specific pathogens.

By reducing the detection time for foodborne pathogens from days to hours, potential threats to public health can be more quickly identified and prevented. Furthermore, decreased testing times may allow for additional testing thereby increasing coverage and helping to prevent the spread of foodborne disease.

Aspects of the invention include methods for detecting pathogens in food samples. Steps of the methods may include obtaining a food sample, treating the food sample with an enzyme, microfiltering the treated food sample, and assaying the microfiltered food sample for presence of a pathogen. Cellular viability of the pathogen is maintained throughout the steps of the method. The treated food sample may include a solution and the food sample may include egg, chicken, spinach, beef, or turkey.

Further steps may include preparing the food sample before the treating step by mechanically blending the food sample. The prepared food sample may include coagulated proteins. In certain embodiments, treating the food sample may include hydrolyzing proteins in the food sample. The enzyme may include a protease which may be incubated with the food sample for less than about 90 minutes. In various embodiments, the enzyme may include a lipase, a cellulase, a hemicellulase, a lysosome, or some combination thereof.

In certain embodiments, assaying steps may include plating the microfiltered food sample on a selective media to detect the pathogen, conducting a polymerase chain reaction (PCR)-based detection of nucleic acid of the pathogen, or a combination of the two. The pathogen being detected may include *Salmonella* or *E. coli*. Methods of the invention may further include a prefiltering step of the food sample just after the treating step but before the microfiltering step. Alternatively, a prefiltering step may be carried out prior to the treating step.

Microfiltering may include cross flow microfiltration which may include concentrating the food sample by passing the food sample through a hollow fiber membrane.

BRIEF DESCRIPTION OF THE FIGURES

FIG. 6 shows a diagram of a Continuous Cell Concentration Device ($C^3D$) according to certain embodiments.

FIG. 30 shows an exemplary hollow fiber module according to certain embodiments.

FIG. 41 shows (A) Pressure drop as a function of time during microfiltration process at room temperature. Enzyme hydrolyzed group (Δ) (n=5) and untreated group (□) (n=3). (B) Permeate flux as a function of time during microfiltration process at room temperature. Permeate flux of enzyme hydrolyzed group (Δ) (n=5) and untreated group (□) (n=3).

DETAILED DESCRIPTION

Systems and methods of the invention relate to rapid detection of pathogens in food samples. Testing may be applied to any food including pork, fruits and vegetables (e.g., spinach or lettuce), beef, chicken, turkey, or other poultry. Methods of the invention may be used to detect the presence of any cellular contaminant or pathogen where the maintenance of cellular viability is important in the sample preparation process (e.g., where presence of the pathogen is determined through growth on media). Pathogens may include any bacteria or fungus. In preferred embodiments, eggs may be tested for the presence of pathogens such as *Salmonella*.

Systems and methods provide for rapid detection of pathogens using specialized sample preparation to capture both interior and surface pathogens from the food sample; enzymatic treatment and optionally pre-filtration to reduce large microfilter-clogging particles; and microfiltration/concentration to prepare a concentrated sample containing viable cells of pathogens present in the original food sample. The concentrated sample may be investigated via PCR or through plating on selective media to identify specific pathogens. Systems and methods may be used to detect pathogens present in food samples at ratios less than 0.5 CFU/g in as little as 7 hours. Pre-filtration to avoid membrane fouling may be conducted with any known filter including, for example, glass microfiber filters (e.g., at 2.7 μm) or nylon filters (e.g., at 10 μm).

Figure 11:
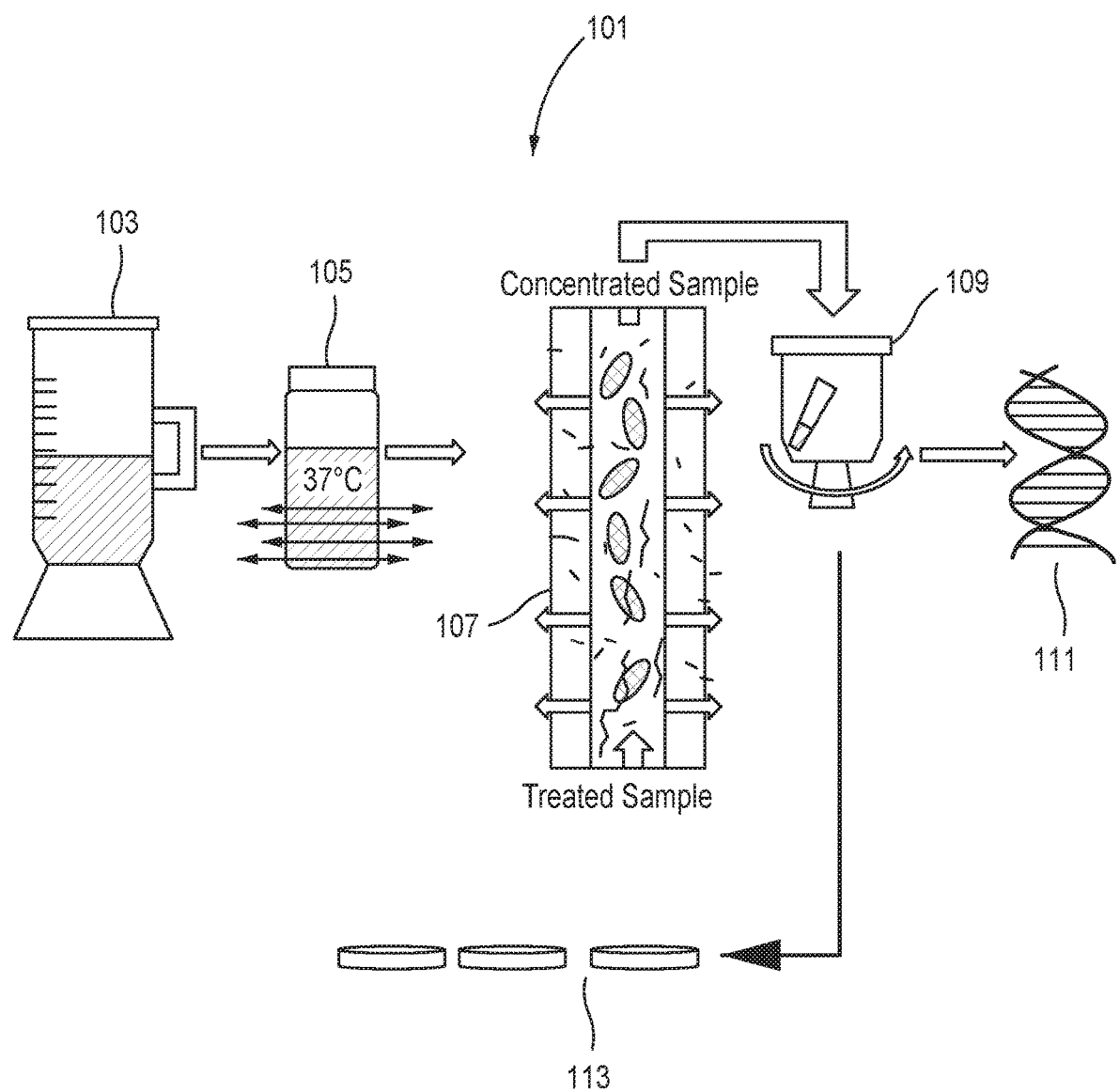
FIG. 11 illustrates exemplary steps according to certain methods of the invention.

FIG. 11 diagrams an exemplary method of the invention. The depicted method 101 includes homogenizing the food sample 103 (e.g., through mechanical blending); treating the homogenized food sample with an enzyme 105 (e.g., 1-5 hour incubation at 37° C.); microfiltering the treated sample to concentrate pathogens therein 107 (e.g., crossflow microfiltration); centrifugation to further concentrate pathogen cells from the food sample 109; followed by plating the concentrated food sample on a selective media 113 and/or conducting PCR-based detection techniques 111 to determine the presence of specific pathogens in the original food sample. Steps of the method should maintain cellular viability of target pathogens at least through the microfiltration step 107.

In one aspect, disclosed herein are methods for concentrating and separating *Salmonella* from egg white samples using a Continuous Cell Concentration Device ($C^3D$) in order to decrease enrichment time. The $C^3D$ utilizes commercially available cross-flow microfiltration modules for concentrating samples in order to enable detection of 0.5 CFU/g of *Salmonella*. (see, Li, et al., 2013, Rapid sample processing for detection of food-borne pathogens via cross-flow microfiltration, *Appl. Environ. Microbiol.*, 79(22): 7048-7054, incorporated herein by reference. It is herein disclosed that concentration and recovery of *Salmonella* originally present in egg white at 0.5 CFU/g and confirmation of the presence of *Salmonella* in egg white through BAX® System PCR assay. Time to detection <0.5 CFU/g of *Salmonella* is 7 hours.

Figure 1:
FIG. 1 shows enzyme hydrolysis effects on egg white homogenates. The vial marked A contains egg white homogenates before enzyme hydrolysis, and the vial marked B contains egg white homogenates after 1 h enzyme hydrolysis.

In certain embodiments, a food sample, such as eggs may be obtained or prepared. The food sample may be prepared by mechanically breaking down the food sample using, for example, a stomacher (Seward, Ltd., West Sussex, UK) or a high shear force blender such as commercially available models from, for example, Kenmore (KCD IP, LLC, Hoffman Estates, IL). Because the $C^3D$ and other microfiltration devices may become clogged with larger particulate matter in a sample, such matter should be reduced or eliminated prior to microfiltration. Accordingly, methods of the invention may include a treatment step after the mechanical preparation or generally prior to microfiltration. Specifically, high shear mechanical blending may cause foaming, coagulation, or other structural changes proteins of the food sample. Treatment steps of the invention may include incubating the prepared food sample with an enzyme to, for example, reduce the presence or size of large particles in the sample. For example, a prepared egg sample may be treated with a protease enzyme to help hydrolyze larger proteins and reduce foaming and coagulation as shown in FIG. 1 (pre-treatment sample on the left and post treatment sample on the right). Food samples may also be treated with enzymes such as cellulase, hemicellulase, lipase, lysozyme, or some combination thereof.

Figure 9:
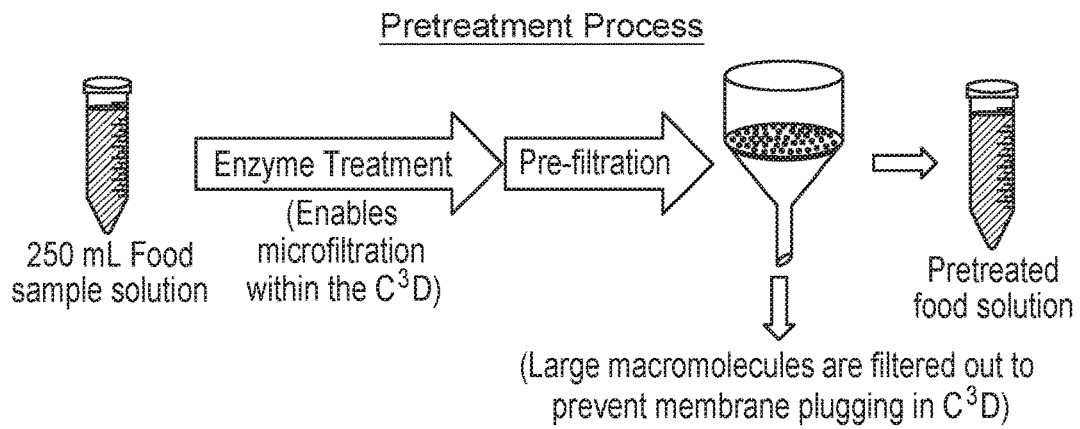
FIG. 9 illustrates exemplary pre-microfiltering steps of certain methods of the invention including enzyme treatment.
Figure 10:
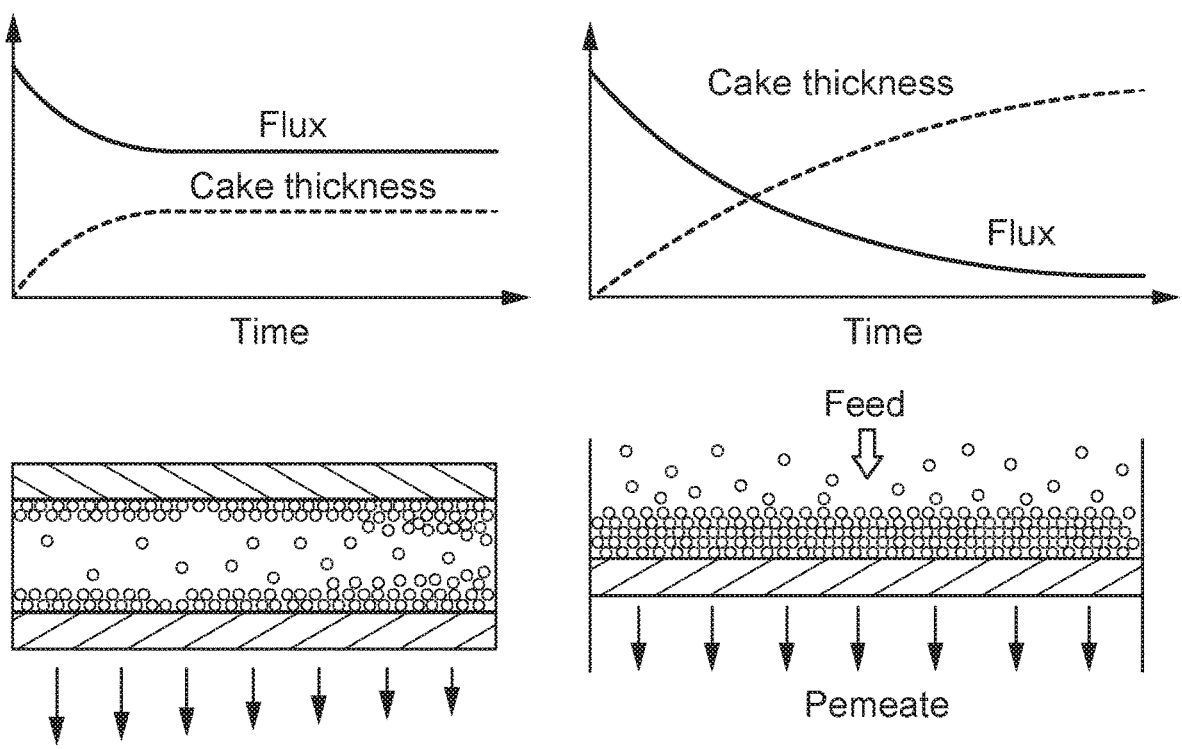
FIG. 10 illustrates compares crossflow and dead end filtration techniques.

FIG. 9 illustrates exemplary pre-microfiltering steps of certain methods of the invention including enzyme treatment. As shown in FIG. 9, the food sample may be subjected to pre-filtration using, for example, a dead end filtration technique. FIG. 10 illustrates the differences between cross-flow (depicted on the left) and dead end filtration (depicted on the right). Optionally, food samples may be subjected to pre-filtering before enzyme treatment, after enzyme treatment, or both. 37° C.

Enzyme treatment may include incubating the food sample with one or more enzymes for any period including, for example 30 minutes, 1 hour, 90 minutes, 2 hours, 3 hours, 4 hours, 5 hours, or more. According to methods of the invention, enzyme treatment should not significantly affect cell viability of the pathogen, preserving the ability to later detect the pathogen using cell culture or other techniques dependent on cellular viability. Food samples may be treated with, for example, a protease to hydrolyze coagulated proteins or otherwise reduce filter clogging particles before microfiltration. Proteases that may be used in treatment steps of the invention include, for example, Protex 7 L available from Genencor Division of Danisco (Rochester, NY) and Promod 298 L available from Biocatalysts Ltd. (Wales, UK). Protex 7 L and Promod 298 L are proteases from *Bacillus* species. Enzymes may be added to the food sample at any concentration including, for example, at about 0.05 mg/mL, 0.075 mg/mL 0.1 mg/mL, 0.15 mg/mL, 0.2 mg/mL, 0.25 mg/mL, or 0.3 mg/mL. Other protease enzymes may include those derived from naturally occurring enzymes found in organisms such as bacteria. Proteases may include serine proteases, cysteine proteases, threonine proteases, aspartic proteases, glutamic proteases, metalloproteases, asparagine proteases, or some combination thereof.

Food samples may also be treated with a lipase, alone or in combination with other enzymes. In certain experiments, treatment with a protease and lipase combination was not found to significantly alter filtration time above that of treatment with protease alone. Individual treatment with lipase or protease did reduce filtration time over untreated food samples however. See FIG. 28. Lipases, or enzymes that catalyze hydrolysis of lipids, used in methods of the invention may include those naturally occurring in organisms such as bacteria. Any lipase may be used with methods of the invention including, for example, Lipomod 34P, Lipomod 957MDP, Lipomod 801MDP, Lipomod 768MDP, Lipomod 691MDP, Lipomod 621MDP, Lipomod 338MDP, Lipomod 224P, Lipomod 187MDP, or Lipomod 29P available from Biocatalysts Ltd. (Wales, UK).

Microfiltration may include any known small pore membrane filtration system. Preferably, microfiltration is performed using a $C^3D$ microfiltration device as described herein. FIG. 6 shows a $C^3D$ according to certain embodiments. The sample may be cycled through a hollow fiber membrane to concentrate the sample using a $C^3D$. The $C^3D$ depicted in FIG. 6 comprises a sample reservoir 1, an ethanol reservoir 2, a NaOH reservoir 3, and an elution buffer reservoir 4 coupled to a 4-1 source selection valve 6 to determine which reservoir flowed by a peristaltic pump 7 through a pressure transducer 9 and through the membrane module 12. Water from a water reservoir 5 is also flowed through the membrane module 12 after being pumped through a flow sensor 10 and pressure transducer 11 by a second pump 8. Permeates are collected by the water, passed through a flow sensor 13, and gathered in a permeate tank 14. Sample, after flowing through the membrane module 12, is directed by a valve 15 either back to the sample reservoir 1 or into a sample collection tube 16 after the microfiltration process is complete.

Figure 7:
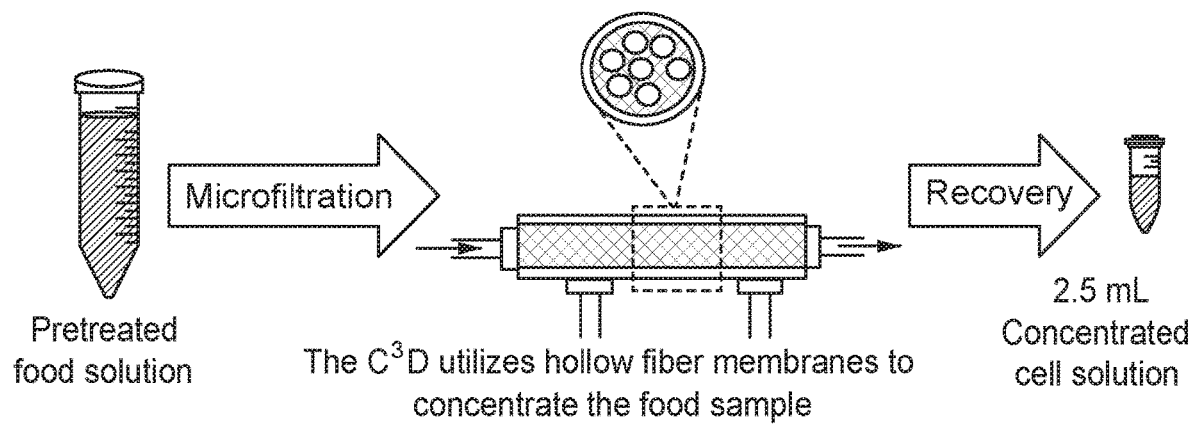
FIG. 7 diagrams exemplary microfiltration steps of the method according to certain embodiments.
Figure 8:
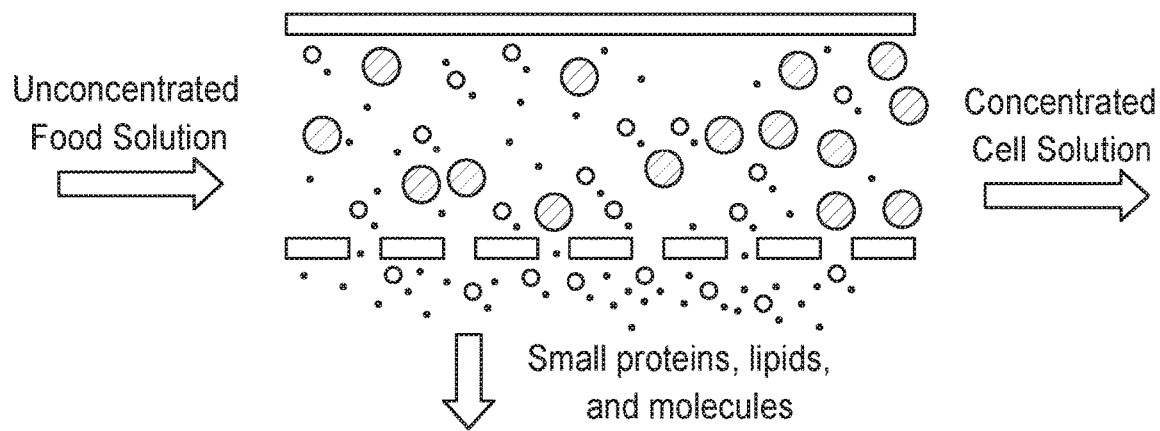
FIG. 8 illustrates the process of cross flow microfiltration according to certain embodiments.

FIG. 7 diagrams exemplary microfiltration steps of the method according to certain embodiments. FIG. 8 illustrates the process of cross flow microfiltration according to certain embodiments. Hollow fiber filtration, as used in the a $C^3D$, provides certain advantages over flat membrane filtration. Specifically, hollow fibers provide a higher surface to volume ratio, increased flux per unit volume of membrane module, and allow continuous operation as the sample can be cycled through the hollow fiber. FIG. 30 shows an exemplary hollow fiber module according to certain embodiments.

Detection of pathogens after treatment and concentration may be through any known means including mass spectrometry, PCR verification, or cell culturing. In preferred embodiments, PCR verification may be used to detect the presence of pathogen specific nucleic acid sequences in the concentrated food sample using amplification primers targeting those sequences. For example, PCR amplification may target the invA (284 bp) gene fragment of *Salmonella* using the following primer sets: invA forward (5'-GTGAAATTATCGCCACGTTCGGGCAA-3' SEQ ID NO: 1), and invA reverse (5'-TCATCGCACCGTCAAAGGAACC-3' SEQ ID NO: 2). Cell culturing may be carried out by plating the concentrated food sample on selective media before incubating and then observing colonies that grow on plates containing the media. For example, *Salmonella* may be plated on Xylose lysine deoxycholate (XLD) agar (VWR, Batavia, IL). Detection of *Salmonella* using mass spectrometry are described, for example, in Bell, et al., 2016, Recent and emerging innovations in *Salmonella* detection: a food and environmental perspective, Microb Biotechnol. 9(3): 279-292, incorporated herein by reference.

Further exemplary systems and methods of the invention may be described using the following examples.

Example 1

Materials. *Salmonella Enteritidis* phage type (PT) 21 was incubated overnight in BBL™ brain heart infusion broth at 37° C., in a G24 environmental incubator shaker at 200 rpm. Fresh grade A shell eggs were purchased from a local grocery store (West Lafayette, IN). Samples were concentrated by microfiltration using a commercial hollow fiber module in an automated instrument ($C^3D$, Li, et al., (2013), Rapid sample processing for detection of food borne pathogens via cross-flow microfiltration, *Applied and Environmental Microbiology*, 79, 7048-7054, incorporated herein by reference).

After cells were recovered in a 10 mL solution, the entire system was cleaned by circulating 0.2 M sodium hydroxide and 70% ethanol before the next sample was processed (Li et al., 2013). The 10 mL sample was centrifuged at 14000 rpm, 10 min, room temperature in a centrifuge 5418 (Eppendorf, Hamburg, Germany) and cells recovered in about 1 mL volume after the supernatant had been decanted (Vibbert, et al. (2015) Accelerating sample preparation through enzyme-assisted microfiltration of *Salmonella* in chicken extract. Biotechnol Prog 31: 1551-1562, incorporated herein by reference).

Cell concentration and recovery process from egg white homogenates. The standard ISO 6579:2002 protocol (International Organization for Standardization, 2002) for liquid egg white homogenates was modified by increasing the buffered peptone water (BPW) from 225 mL to 500 mL, and substituting a Kenmore® Model Power 10 blender (Sears Holdings, Hoffman Estates, IL) in place of a stomacher. Sterilization before each run was through rinsing with 10% bleach for 10 min and 10% ethanol overnight.

Grade A shell eggs were soaked in 70% alcohol for 30 min (U.S. Food and Drug Administration, 2014b). 4 eggs were air-dried to prevent sample contamination before they were broken. Shells were broken using a sterile spoon and placed in the sterile blender. After removing the egg yolk using a sterile spoon, 100 g of egg whites were homogenized by blender for 15 seconds. The egg whites were then artificially spiked with <0.5 CFU/g of *Salmonella Enteritidis*. The aqueous egg white homogenates were then prepared by mixing 25 g of homogenized egg whites with 1 mg of Antifoam A concentrate (Sigma-Aldrich, St. Louis, MO, to minimize foam formation), 500 g of buffered peptone water and protease. After enzyme treatment and 1 to 5 hours enrichment, microfiltration using $C^3D$ and centrifugation was carried out (Li et al., 2013; Vibbert et al., 2015).

Optimization of enzyme exposure for microbial viability. The effect of protease on *Salmonella* viability was determined by incubating the microorganism in the presence of the enzyme for 120 minutes under different experimental conditions. Protex™ 7 L was provided by Genencor Division of Danisco (Rochester, NY), and Promod™ 298 L was purchased from Biocatalysts Ltd. (Wales, UK). Protex™ 7 L and Promod™ 298 L are protease from *Bacillus* species. Both enzymes were added to the egg white homogenates at 0.2 mg/mL respectively, followed by inoculation of *Salmonella* at 102 CFU/mL of aqueous egg white homogenates. Protein concentrations of Protex™ 7 L and Promod™ 298 L were 39.6 mg/mL and 42.4 mg/mL, respectively. The concentration of protein in commercial enzymes was determined by the method reported earlier (Vibbert et al., 2015).

Plating. Xylose lysine deoxycholate (XLD) agar (VWR, Batavia, IL) was used as the selective medium for enumeration of *Salmonella*. Two different sizes of petri dishes were used to determine the number of viable cells. 100 μL of aqueous egg white homogenates and concentrated samples were spread on the 100×15 mm petri dishes (VWR, Catalog No. 25384-094, Batavia, IL) and 1 g of egg whites were spread on the 150×15 mm petri dishes (VWR, Catalog No. 25384-326, Batavia, IL) to count initial cell numbers. For all experiments, colonies were plated on XLD and counted after 20 h of incubation at 37° C. During the microfiltration process through the $C^3D$, the data for the permeate flux and pressures were collected each 100 seconds (Li et al., 2013).

Sodium dodecyl sulfate polyacrylamide gel electrophoresis (SDS PAGE) analysis. All the samples were prepared by mixing Laemmli Sample Buffer with 5% (v/v) of 2-mercaptoethanol and heating at 95° C. for 5 minutes based on instruction manual (Bio-Rad, Hercules, CA).

SDS-PAGE was performed by loading 10 μL of samples containing 0.5 to 17 μg protein on 12% Mini-PROTEAN® TGX™ Precast Gels. Gels were stained for 2 hours in Coomassie Brilliant Blue R-250 Staining Solution, and de-stained in Coomassie Blue R-250 de-staining solution (Methanol:Acetic acid:DI water=4:1:5).

*Salmonella* detection using BAX®-PCR system and conventional PCR.

BAX®-PCR method was performed using the manufacturer's protocol. Conventional PCR experiments for invA (284 bp) gene fragment amplification were carried out using primer sets and methods reported earlier (Vibbert et al., 2015). The following primer sets were used to target the invA gene: invA forward (5'-GTGAAATTATCGC-CACGTTCGGGCAA-3' SEQ ID NO: 1), and invA reverse (5'-TCATCGCACCGTCAAAGGAACC-3' SEQ ID NO: 2).

Statistical analysis. For statistical evaluation of microbial growth activities, an ANOVA test was performed using the Minitab® 17. This was followed by post hoc comparisons using the Tukey's test. Significance was determined at $p<0.05$ (Vibbert et al., 2015).

Results and Discussion:

Mechanical blending. Inappropriate sampling results in false negatives. Therefore, the collected food sample should represent the original food as exactly as possible (Zadernowska, A. & Chajecka, W. (2012), Detection of *Salmonella* spp. presence in food. In Mahmoud B. S. M. (Eds.), *Salmonella*—a dangerous foodborne pathogen (pp. 393-412). Croatia: In Tech, incorporated by reference). In the classical protocol, the stomacher approach has been used to extract microorganisms from the surface of food samples. However, for cases of egg contamination, *Salmonella* can swim and move inside egg whites (Grijspeerdt K, Kreft J U & Messens W, 2005). In order to recover the equivalent of 0.5 CFU/g of *Salmonella* in egg white samples, mechanical blending was used to obtain a homogeneous mixture of both interior and surface pathogens suitable for concentration by microfiltration (Li X et al., 2013; Vibbert et al., 2015).

Enzyme treatment. The main components for egg whites are shown in Tables 2 and 3 (Belitz, et al., (2009) *Food Chemistry*. (4th ed.). *Heidelberg: Springer*, (Chapter 11), incorporated herein by reference). Blending the sample with strong shear force instead of conventional stomaching generates egg white homogenates with high concentrations of dispersed and soluble protein with coagulation and foaming of protein (Stadelman W. J., Cotterill O. (1995), Egg Science and Technology. NY: Food Products Press, incorporated by reference).

TABLE 2

The composition of egg whites (Adapted and modified from Food chemistry 4th edition, 2009).
Egg whites

| Composition | Percentage (%) |
|---|---|
| Protein | 10.6 |
| Fat | 0.03 |
| Carbohydrate | 0.9 |
| Minerals | 0.6 |
| Water | 87.9 |

TABLE 3

The composition of characteristics of egg white proteins (Adapted and modified from Food chemistry $4^{th}$ edition, 2009)
Egg white proteins

| Composition | Percentage (%) | Molecular weight (kda1) | pI (pH) |
|---|---|---|---|
| Ovalbumin | 54 | 44.5 | 4.5 |
| Ovotransferrin | 12 | 76 | 6.1 |
| Ovomucoid | 11 | 28 | 4.1 |
| Ovomucin | 3.5 | $5.5\text{-}8.3 \times 10^6$ | 4.5-5.0 |
| Lysozyme | 3.4 | 14.3 | 10.7 |
| Ovoglobulin G2 | 4 | 30-45 | 5.5 |
| Ovoglobulin G3 | 4 | — | 5.8 |
| Flavoprotein | 0.8 | 32 | 4.0 |
| Ovoglycoprotein | 1 | 24 | 3.9 |
| Ovomacroglobulin | 0.5 | 760-900 | 4.5 |
| Ovoinhibitor | 1.5 | 49 | 5.1 |

Table 4 shows the concentration of *Salmonella* cells present in the sample at each step of the process for enzyme incubation/hydrolysis times of 1, 2, 3, and 5 hours.

(pp. 1-42). John Wiley & Sons, Inc.; Hoppe, A. (2010). Examination of egg white proteins and effects of high pressure on select physical and functional properties (thesis). University of Nebraska Lincoln, Food Science and Technology Department; Johnson, T. M. and Zabik, M. (1981), Egg albumen proteins interactions in an angel food cake system, Journal of Food Science, 46, 1231-1236; Raeker, M. O. and Johnson L. A. (1995) Cake-baking (high-ratio white layer) properties of egg white, bovine blood plasma, and their protein fractions, Cereal Chem, 72 (3): 299-303; Yang, X. (2014), Optimizing textural properties of soft solid foods: replacing eggs. In Yadunandan, L. D. & Joseph M. L. (Eds.), Food texture design and optimization (Chapter 03). Wiley Blackwell; each of which is incorporated by reference). When shear forces are applied to egg whites, ovalbumin undergoes structural changes and formation of disulfide bridges with other ovalbumin particles. Consequently, protein aggregation with stable foams can be generated (Hoppe A, 2010).

According to Lechevalier et al (2005), ovalbumin, ovotransferrin and lysozyme undergo strong molecular covalent aggregates when they are exposed to air—water interface and play synergistic effects in the protein denaturation. Lechevalier, et al., (2005), Ovalbumin, ovotransferrin, lysozyme: three model proteins for structural modifications at the air-water interface, *Journal of Agricultural and Food Chemistry*, 51, 6354-6361, incorporated herein by reference). Ovalbumin and ovotransferrin showed secondary structural modification at the air-water interface from α-helix to β-sheet and β-turn with enhanced surface hydrophobicity and formed insoluble particles (Lechevalier, et al., (2005) Evidence for synergy in the denaturation at the air—water interface of ovalbumin, ovotransferrin and lysozyme in ternary mixture, *Food Chemistry*, 92 (1), 79-87, incorporated herein by reference). The precise mechanism of foaming properties from globulin proteins is not clear (Eunice C. Y., Chan, L. & Kim H. O. (2008), Structure and chemical composition of eggs. In Mine Y. (Eds.), Egg bioscience and biotechnology (pp. 1-42). John Wiley & Sons, Inc.; Mine, Y. (1995). Recent advances in the understanding of egg-white protein functionality. Trends in Food Science & Technology, 6(7), 225-232; Sugino, H., Nitoda, T. & Juneja, L. R. (1997), General chemical composition of hen eggs. In Yamamoto, T., Juneja, L. R., Hatta, H. & Kim, M. (Eds.), Hen eggs, their basic and applied science (pp. 13-24). CRC press LLC., each

TABLE 4

Concentration and recovery of artificially spiked *Salmonella* in egg whites. The *Salmonella* cells were enumerated for each step by plating.
Data are presented as mean ± standard deviation where n = 3 or 5.

| | Enzyme hydrolysis time (h) | Cell in egg white (CFU/g) | Cells in egg white homogenates after each processing step | | | |
|---|---|---|---|---|---|---|
| Experiment | | | Microfiltration (CFU/mL) | Microfiltered volume (mL) | Centrifugation (CFU/mL) | Centrifuged volume (mL) |
| 1 (n = 5) | 1 | 0.9 ± 0.5 | 7 ± 4 | 8 ± 1 | 66 ± 23 | 0.9 ± 0.4 |
| 2 (n = 5) | 2 | 0.8 ± 0.4 | 41 ± 16 | 8 ± 1 | 299 ± 146 | 1.0 ± 0.5 |
| 3 (n = 8) | 3 | 0.5 ± 0.4 | 87 ± 38 | 9 ± 1 | 559 ± 465 | 1.1 ± 0.3 |
| 4 (n = 5) | 5 | 0.3 ± 0.2 | 441 ± 375 | 11 ± 1 | 3379 ± 2640 | 1.1 ± 0.4 |

Several studies reported that ovalbumin, ovotransferrin, lysozyme and globulin proteins expressed a key role in foaming properties of egg whites (Eunice C. Y., Chan, L. & Kim H. O. (2008), Structure and chemical composition of eggs. In Mine Y. (Eds.), Egg bioscience and biotechnology of which is incorporated by reference). Consequently, concentration of homogenized egg white samples obtained from a blender are more difficult for microfiltration procedure.

The coagulated and denatured protein block micro-filter pores, and prevents microfiltration or significantly slows the process previously explained mechanisms include formation of protein films on the membrane resulted in the filter fouling over the microfiltration process by bovine serum albumen (Li X et al., 2013; Vibbert et al., 2015; Kelly, S. T., & Zydny, A. L. (1997). Protein Fouling During Microfiltration: Comparative behavior of different model proteins. *Biotechnology and Bioengineering*, 55(1), 91-100, incorporated herein by reference). To minimize the fouling effects of the proteins during sample microfiltration for microbial concentration and recovery, a biochemical pretreatment step using enzymes (protease) is needed. Addition of protease to the homogenized egg whites clarifies the sample and enables rapid microfiltration to be achieved (FIG. 1).

Figure 2:
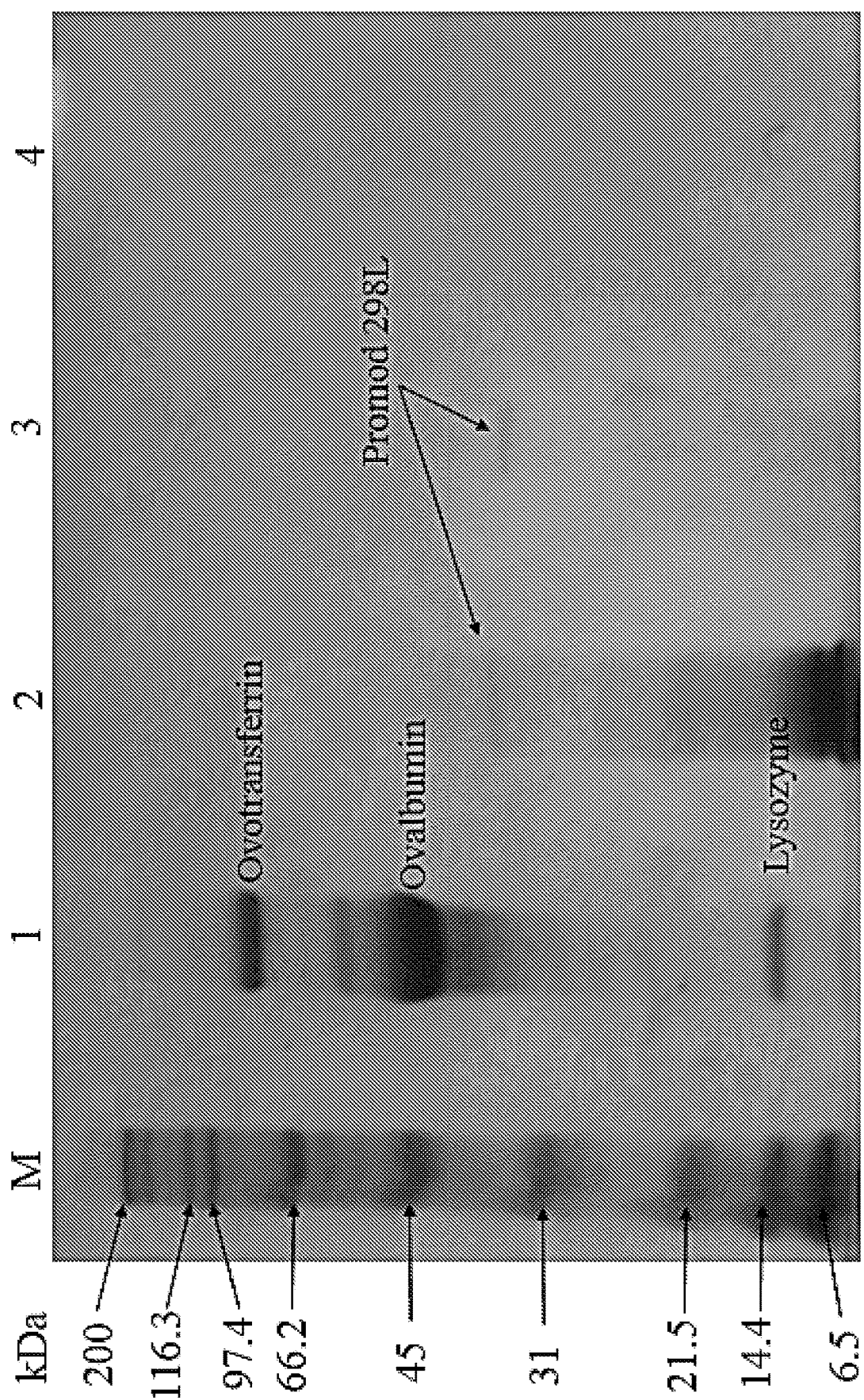
FIG. 2 shows SDS PAGE analysis performed by loading 17 µg of protein for lane 1 (Egg white homogenates) to 2 (enzyme incubated egg white homogenates), 0.5 µg protein for lane 3 (Protease) and 5.4 µg of protein for lane 4 (Buffered peptone water) respectively using 12% Mini-PROTEAN® TGX™ Precast Gels.

SDS PAGE analysis showed the use of the protease changed the protein profile in the lane 1 which includes ovalbumin, ovotransferrin and lysozyme to what is observed in lane 2 where the sample was derived from egg white homogenates after the protease was added and incubated for 3 hours (FIG. 2). The protein distribution shows a decrease in molecular weight after the protease is added and can explain the changed color and turbidity of the samples. This results suggest successful hydrolysis of egg white proteins can be applicable to rapid microfiltration when using Promod™ 298L.

Evaluation of cell viability. Wang G and Wang T. (2008) showed the successful egg-yolk protein hydrolysis with Protex™ 7L and significantly increased the protein solubility. Wang, G. & Wang, T. (2009), Egg yolk protein modification by controlled enzymatic hydrolysis for improved functionalities, *International Journal of Food Science and Technology*, 44, 763-769, incorporated by reference. Vibbert et al. (2015) treated Protex™ 7L to chicken extract to degrade protein particles to enable microfiltration. However, since proteases are effective in inactivating microorganisms according to most authors (Ensign, J. C. & Wolfe, R. S. (1966), Characterization of a small proteolytic enzyme which lyses bacterial cell walls, *Journal of bacteriology*, 2, 524-534; Scott, J. H. & Schekman, R. (1980), Lyticase: endoglucanase and protease activities that act together in yeast cell lysis, *Journal of bacteriology*, 414-423; Kodama, T., Endo, K., Ara, K., Ozaki, K., Kakeshita, H., Yamane, K., & Sekiguchi, J. (2007), Effect of *Bacillus subtilis* spoOA mutation on cell wall lytic enzymes and extracellular proteases, and prevention of cell lysis, *Journal of bioscience and bioengineering*, 103, 13-21; Rice, K. C., & Bayles, K. W. (2008), Molecular control of bacterial death and lysis, Microbiology and molecular biology reviews, 85-109; Salazar, O., & Asenjo J. A. (2007), Enzymatic lysis of microbial cells, *Biotechnology Letters*, 29, 985-994, each of which is incorporated by reference), their effect in lengthy *Salmonella* incubation time was tested.

Figure 3:
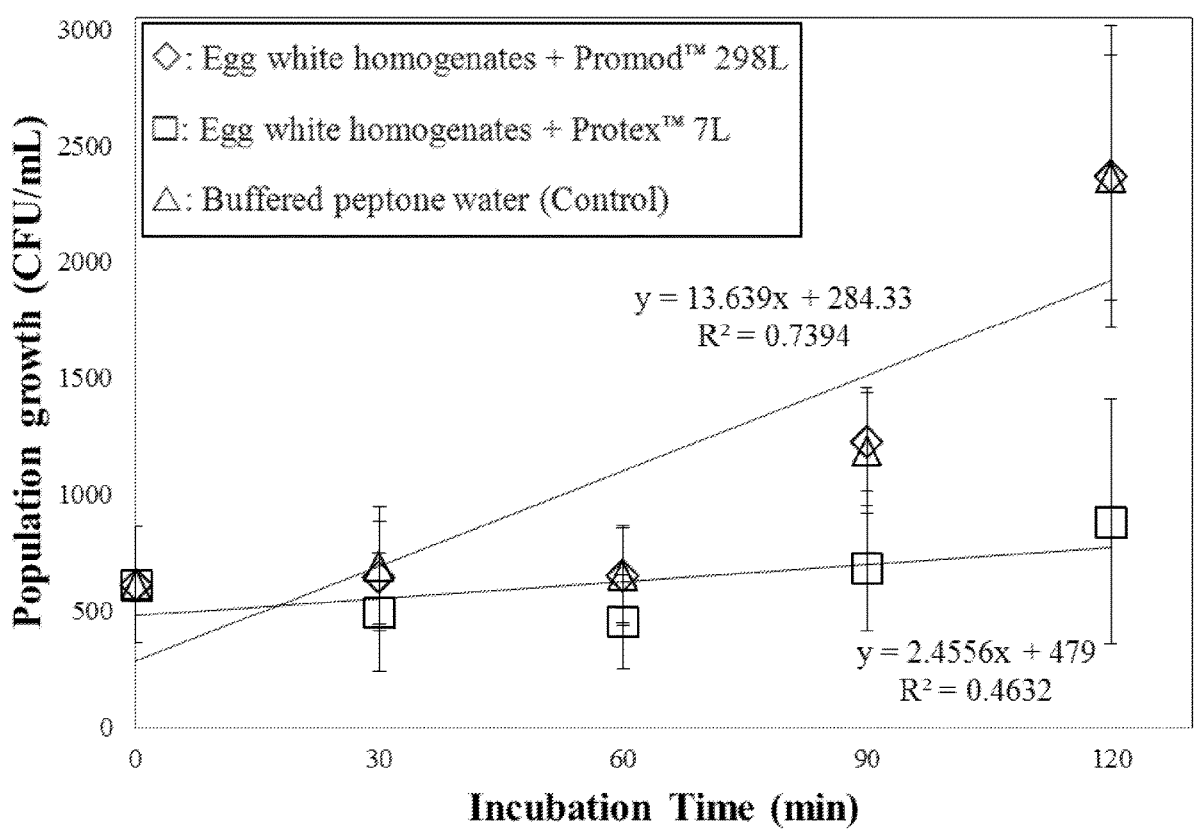
FIG. 3 shows a plot of cell population (*Salmonella*, 103 CFU/mL) growth rate when inoculated with 0.2 mg/mL of Promod™ 298L (□) 0.2 mg/mL of Protex™ 7L (◇), or without enzyme as control group (Δ) in egg white homogenates. Data are the average of three replicates. Error bars represent standard deviation. Population growth rates up to 90 minutes of inoculation time are not significantly different at the 95% confidence level.

A comparison of the effects on the growth of *Salmonella Enteritidis* was carried out for two different enzymes (Protex™ 7L (0.2 mg/mL) and Promod™ 298L (0.2 mg/mL) for a period of 2 h (FIG. 3). Cell viability is not significantly affected after 90 min (p>0.05) and the number of cells increased over the period of 2 hours. However at 120 min, Protex™ 7L led to significantly slower growth of cells compared to other samples (p<0.05). Over longer incubation times *Salmonella* growth is more sensitive to Protex™ 7L. Statistical analysis using an ANOVA suggests that there are no significant differences in the average cell growth between control group and Promod™ 298L treated group (p>0.05) for 2 h. In this case, *Salmonella* enrichment can be expected during the enzymatic hydrolysis step with Promod™ 298L and increased cell recovery may be expected after enzyme treatment followed by microfiltration and centrifugation.

Figure 4A:
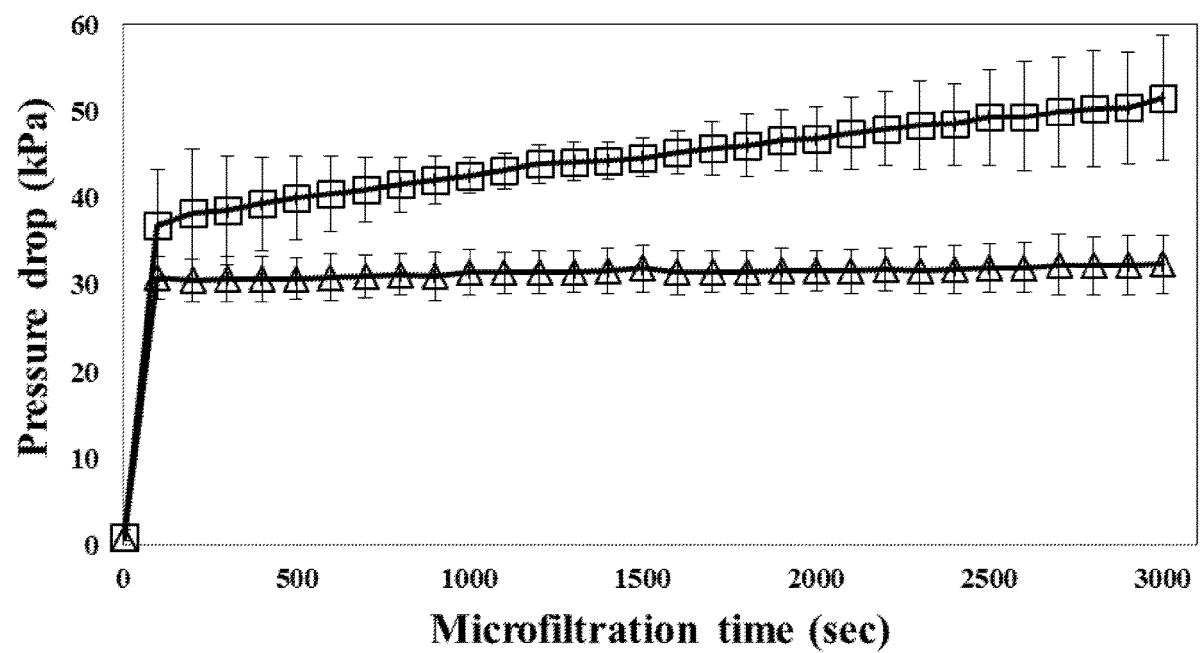
FIGS. 4A and 4B show plots of transmembrane pressure (FIG. 4A) and permeate flux (FIG. 4B) as a function of time during microfiltration process by $C^3D$ at room temperature. Enzyme hydrolyzed group (Δ) (n=5) and untreated group (□) (n=3). Error bars represent standard deviation.
Figure 4B:
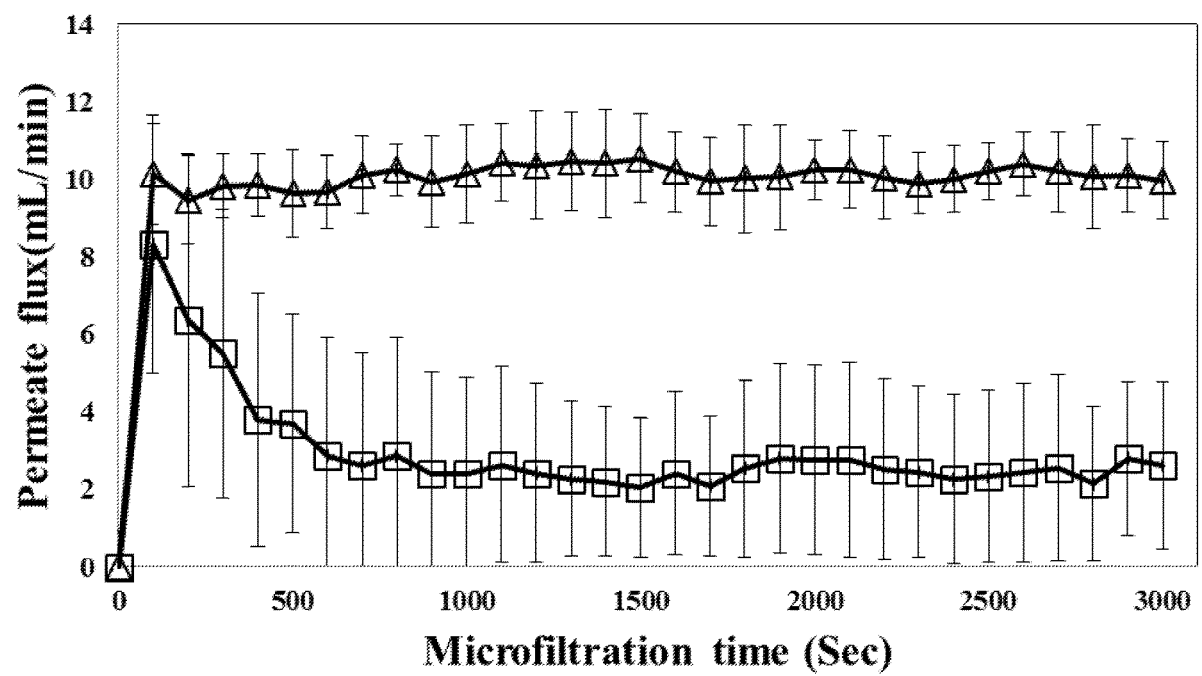

Cell concentration and recovery using Microfiltration. Microfiltration of enzyme treated egg white homogenates using commercial hollow-fiber membranes finished within 60 min at the permeate flow rate of 9.8±1.8 mL/min with the pressure drop across the hollow fiber module at 30.3±0.7 kPa (FIGS. 4A and 4B). However, the untreated samples took more than 3.5 h or could not be completed due to clogging of the filter.

Pressure drop across the hollow-fiber module and permeate flux are key indicators of microfiltration membrane fouling. During the microfiltration process, pressure drop gradually increased to compensate for the membrane surface fouling by particles. On the other hand, flux gradually decreases because of presence of proteins (Choi, H., Zhang, K., Dionysiou, D. D., Oerther, D. B., & Sorial, G. A. (2005), Effect of permeate flux and tangential flow on membrane fouling for wastewater treatment, *Separation and Purification Technology*, 45, 68-78; Ladisch, M. R. (2001). Bioseparations Engineering: Principles, Practice, and Economics (100-106), NY: Wiley Interscience; each of which are incorporated by reference).

An increasing pressure drop with decreasing flux was detected in egg white homogenates that were not enzyme treated compared to a high flux rate and low pressure drop observed during the entire microfiltration and cell recovery process for the protease treated samples. The <60 min microfiltration period for 525 mL of enzyme treated egg white homogenates is not statistically significantly different compared to processing time for 525 mL of buffered peptone water alone (<60 min) (p>0.05).

Figure 5:
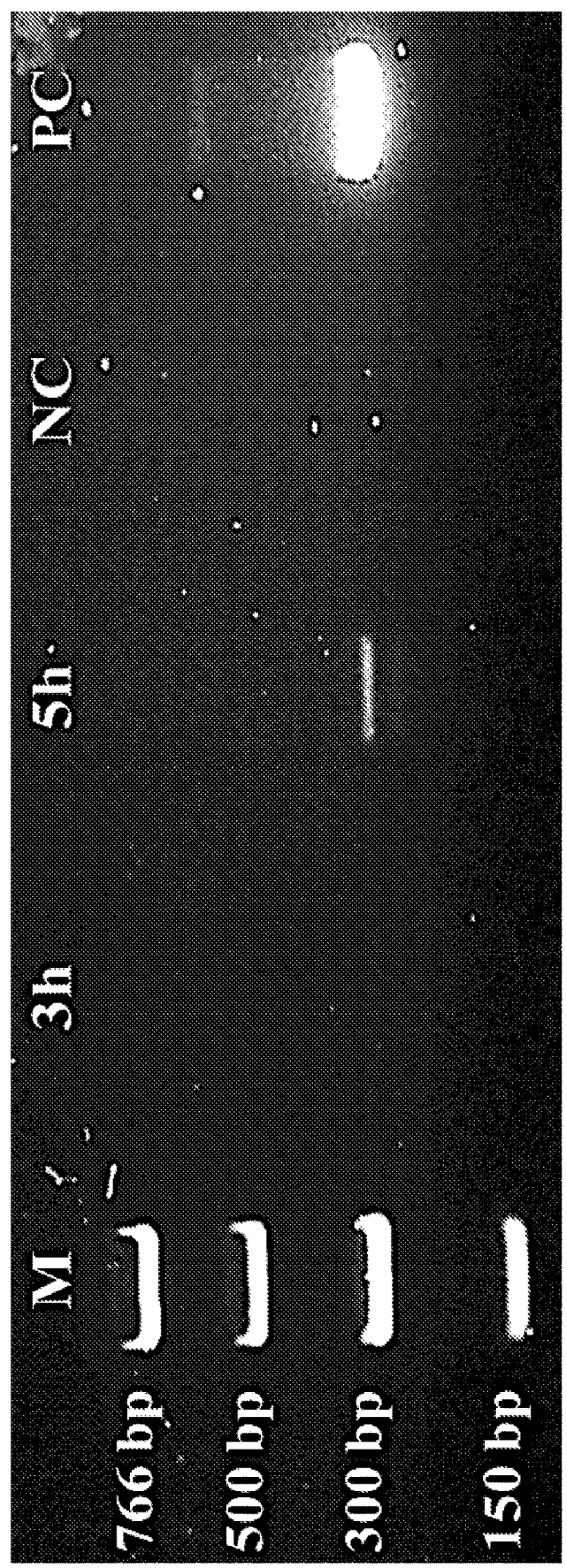
FIG. 5 shows PCR results used to determine the minimum enzyme hydrolysis time. 3 h and 5 h samples were from the microbial lysate extracted by commercial DNA kit from *Salmonella Enteritidis* after 3 h and 5 h enrichment (enzyme hydrolysis) steps respectively. NC is a negative control, PC is a positive control (microbial lysate extracted by commercial DNA kit from 108 CFU of *Salmonella Enteritidis*).

*Salmonella* detection. The minimum time required was about 3 h for simultaneous enrichment and enzyme treatment followed by microfiltration and centrifugation required to obtain higher than 102 CFU of *Salmonella* that could be detected using BAX®-PCR in samples spiked with <0.5 CFU/g (Table 1). The minimum number of cells concentrated and recovered from the processed egg white homogenates allowing visualization of a positive signal bands (invA: 284 bp and hilA: 497 bp), about 103 CFU/mL, is consistent with previous results (FIG. 5) (Vibbert et al., 2015). Rijpens et al. (1999) and Soria et al. (2012) spent more than 20 h for the only enrichment step to detect *Salmonella* from egg white and yolk-albumen samples using PCR. Rijpens N., Herman L., Vereecken F., Jannes G., De Smedt J. and De Zutter L. (1999), Rapid detection of stressed *Salmonella* spp. in dairy and egg products using immunomagnetic separation and PCR, *International Journal of Food Microbiology*, 46, 37-44; Soria M A, Soria M C & Bueno D J. (2012), A comparative study of culture methods and polymerase chain reaction for *Salmonella* detection in egg content, Poultry Science 91, 2668-2676; each of which is incorporated by reference. However, whole process (enrichment, microfiltration, centrifugation and PCR) to detect <0.5 CFU/g of *Salmonella* in egg whites is completed in 7 h. In conclusion, protease pretreatment is simultaneously a pre-enrichment step (3 h) that facilitates *Salmonella* growth in egg white homogenates and reduces microfiltration time (<1 h). Through these processes, we yield detectable level of *Salmonella* using PCR. The total time to detect <0.5 CFU/g of *Salmonella* in egg whites can be completed in 7 h.

Additional disclosure is found in Appendix-A and Appendix-B, Appendix-C, Appendix-D, Appendix-E, Appendix-F, Appendix-G, Appendix-H, and Appendix-I filed herewith, entirety of which are incorporated herein by reference into the present disclosure.

Those skilled in the art will recognize that numerous modifications can be made to the specific implementations described above. The implementations should not be limited to the particular limitations described. Other implementations may be possible.

Example 2

Figure 12:
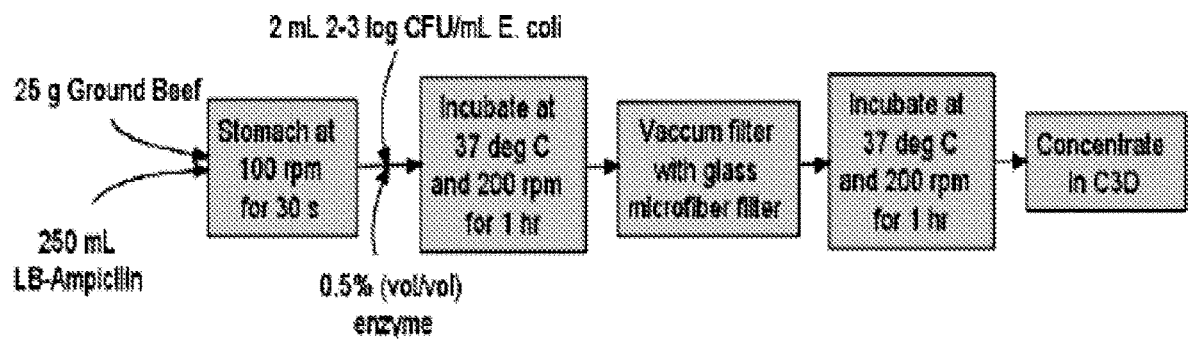
FIG. 12 illustrates processing methods for ground beef as used in Example 2.
Figure 13:
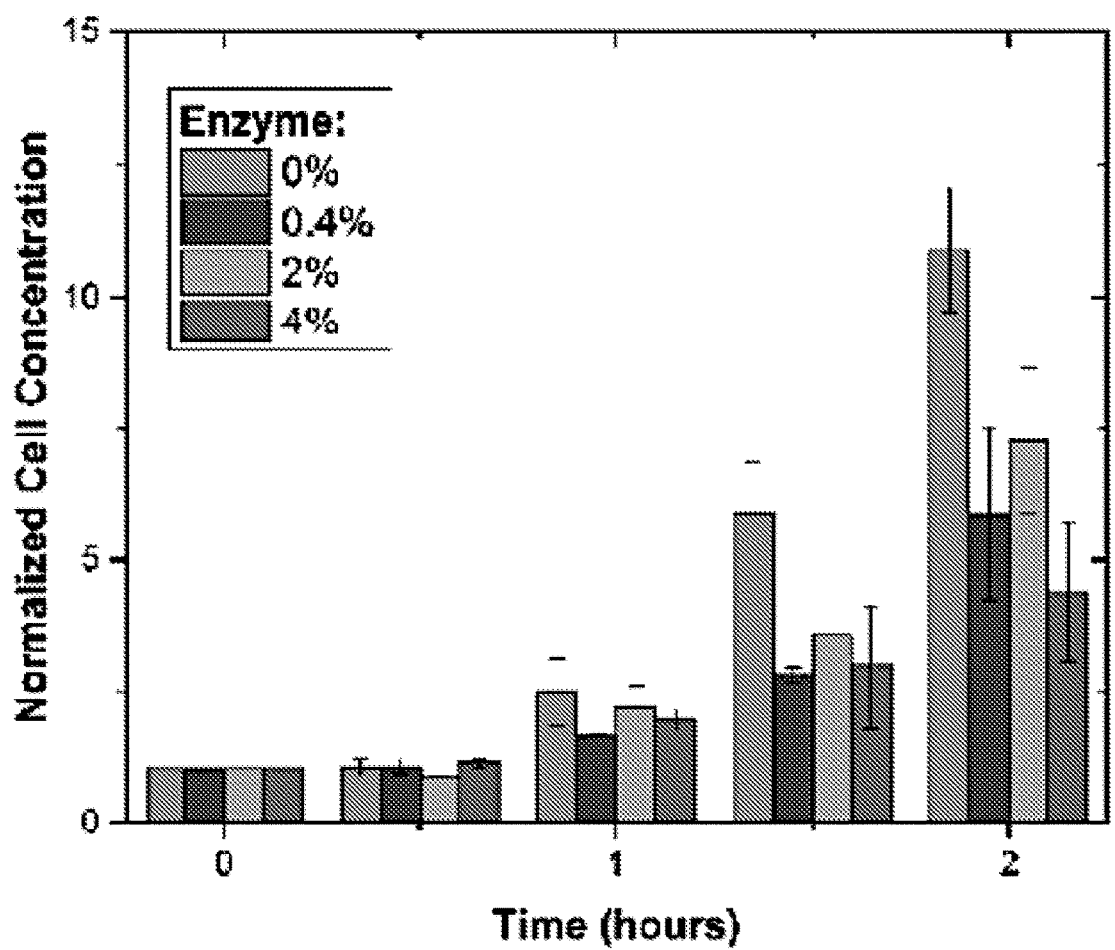
FIG. 13 shows cell population (*E. coli*) percent change when incubated with protease.

The role of protease to enable microfiltration and ensure recovery of *E. coli* in ground beef was investigated. Experiments were conducted to determine the effect of enzyme hydrolysis, if any, on microbial cell growth and recovery. Samples were processed as illustrated in FIG. 12. Once processed, cell populations were quantified by plating on selective media. Microfiltration rates were obtained throughout the concentration process in the $C^3D$. Changes in cell population up through 90 minutes of incubation time were not significant between enzyme-treated and control solutions. Differences in enzyme loading do not significantly affect cell population growth. FIG. 13 shows cell population (*E. coli*) percent change when incubated with protease. As seen in Table 5, percent recovery for 0.4% enzyme loading was extremely low, indicating a higher enzyme loading requirement. 4% enzyme loading results showed the highest average percent recovery for both the C3D and overall process. Samples were treated with the protease PromoD 439 enzyme.

TABLE 5

| Enzyme Loading | Trial | % Recovery from $C^3D$ | Total % Recovery |
|---|---|---|---|
| 0.40% | 1 | 3% | 4.86% |
|  | Average | — | — |
| 2% | 2 | 43% | 35.09% |
|  | 3 | 12% | 6.54% |
|  | 4 | 49% | 1.78% |
|  | Average | 35% | 14.47% |
| 4% | 5 | 50% | 37.46% |
|  | 6 | 61% | 36.24% |
|  | 7 | 55% | 36.55% |
|  | Average | 55% | 36.75% |

Conclusions 90 mins is the maximum enzyme hydrolysis time up to which differences in cell viability are not statistically significant when compared to non-enzyme treated samples.

Enzyme loading is viable for treating ground beef solutions. Differences in cell viability are not statistically significant between 0.40%, 2%, and 4% enzyme loading up to 2 hours.

Enzyme loaded samples had significantly larger cell recoveries for both the C3D and overall process. Generally, as the percent enzyme loading increases, percent cell recovery increases.

Example 3

A protocol was developed for rapid concentration, recovery and detection of *Salmonella* in various food samples at bacterial levels of 1 CFU/g of less. A microfiltration approach, followed by centrifugation, was used to concentrate the cells with PCR based methods used for final detection. The entire process (sample preparation, concentration, recover, and PCR based detection) was completed in 7 hours. Further confirmation of results using standard methods was obtained in 20 hours using enrichment and plating on a selective media Enzymatic hydrolyzing process: Evaluation of the effectiveness of treating with optimal enzymes that do not show bacterial cytotoxicity to hydrolyze various food samples was carried out. Various filters based on dead-end filtration were evaluated to separate huge particles from the food samples with maximized quantities of target bacteria. Increased concentration of bacteria was checked by plating and PCR methods after treatment and microfiltration. Concentration methods including enzymatic hydrolyzing, pre-filtering, and $C^3D$ concentration/microfiltration were used to investigate concentration and recovery of microbiota from chicken carcass and tap water as well as concentration and recovery of *Salmonella* from egg white and spinach. Results indicated that both naturally occurring bacteria and inoculated *Salmonella* could be concentrated and separated from various food samples rapidly by $C^3D$ cross-flow microfiltration. Pre-treatment with an optimal enzyme cocktail reduced time for the bacterial separation step and increased yield of bacteria with low volume. Recovery and detection of the target bacteria was accomplished within 7 hours.

Example 4

Enzyme pretreatment for rapid microfiltration, recovery and detection of *salmonella* in raw chicken samples was investigated. Commercial poultry is one of the fastest growing sectors of the agricultural industry. Consequently, an increase in poultry consumption increases the potential risk for exposure to *Salmonella* through contaminated food commodities. Microfiltration-based (0.1 μm-10 μm) strategies to concentrate bacteria, protozoa, and viruses from water have seen widespread success during the last two decades. The presence of colloidal particles, proteins, lipids, and carbohydrates can agglomerate and foul membrane modules during microfiltration. The combined approach (Enzyme treatment and commercial hollow fiber membranes module) maximizes both flux and recovery of about 70% of target viable microorganisms from chicken carcass rinses. The whole procedure from sample processing to microbial detection by PCR takes about 8 hours, including a short enrichment step. Both naturally occurring and spiked *Salmonella* were recovered from low initial cell levels (less than 10 CFU/g).

Methods

Preparation of aqueous chicken homogenates and carcass rinses: Aqueous chicken homogenates and chicken carcass rinses were prepared from store-purchased chicken meat following the USDA protocol. Enzymatic hydrolyzing process: Evaluation of the effectiveness of treating with optimal enzymes that do not show bacterial cytotoxicity to hydrolyze various food samples was carried out. Pre-filtering process: Various flat sheet membranes were evaluated to separate huge particles from the food samples with maximized quantities of target bacteria. Cell concentration by C3D and centrifugation: Increased concentration of bacteria was checked by plating and PCR methods.

Figure 14:
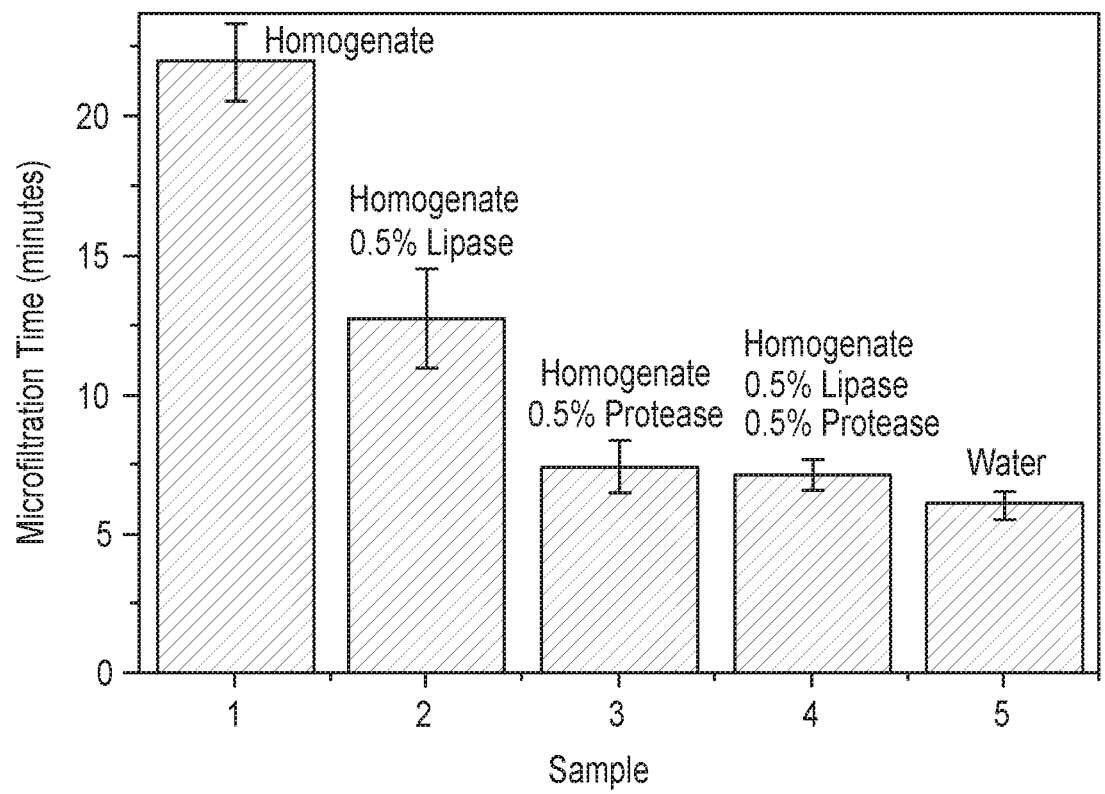
FIG. 14 shows filtration time using different biochemical pretreatment methods.
Figure 15:
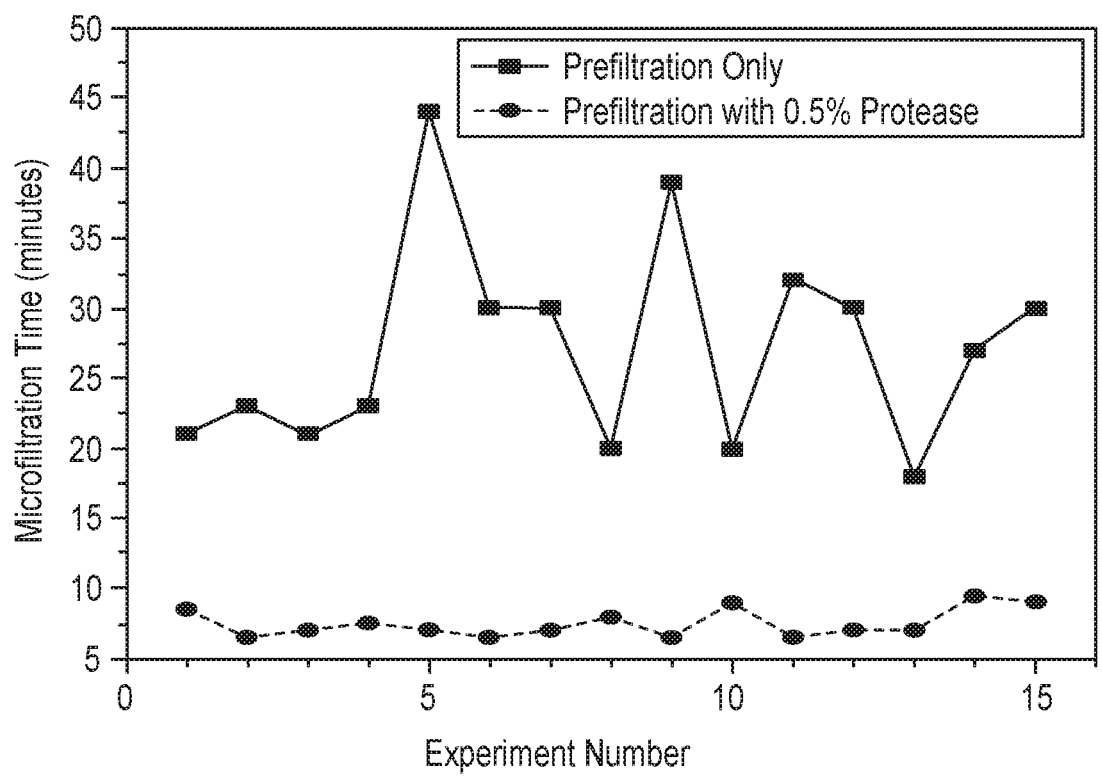
FIG. 15 shows variability in microfiltration times for filtered aqueous chicken homogenates, either pretreated or not pretreated with 0.5% (v/v) protease.
Figure 16:
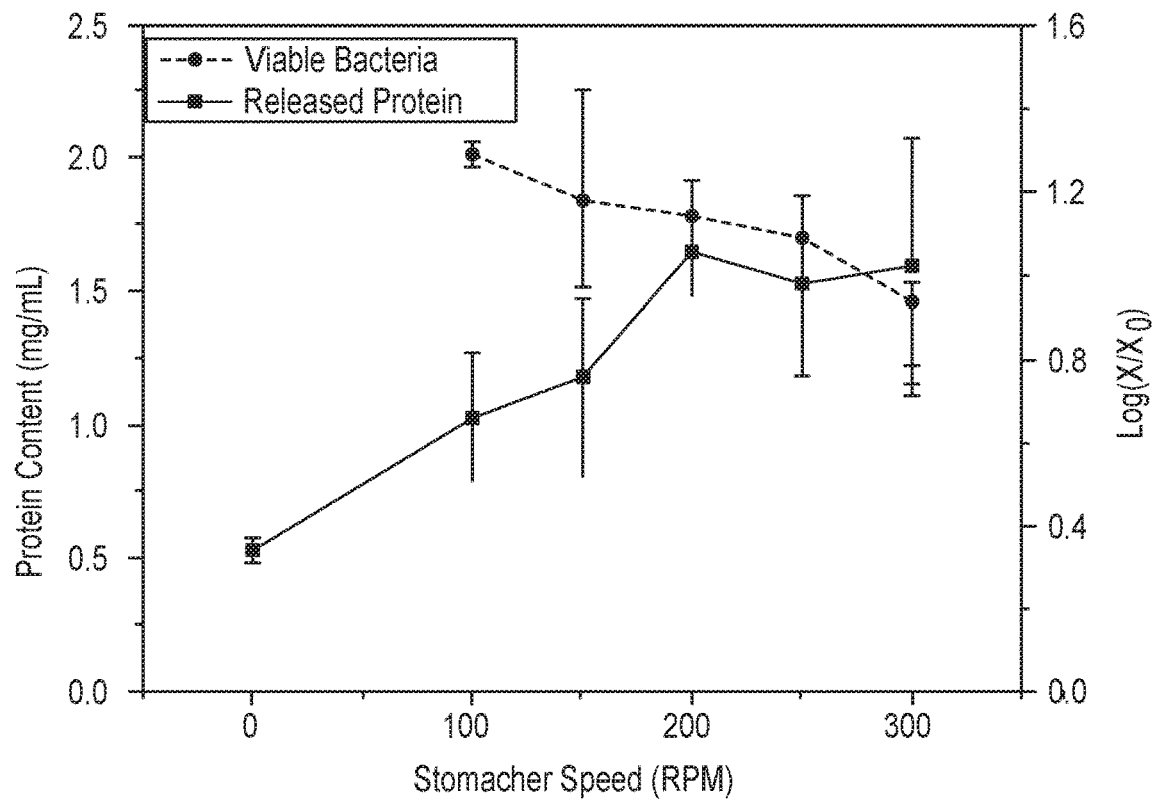
FIG. 16 shows effects of stomacher speed and time on protein concentration and bacterial viability.
Figure 17:
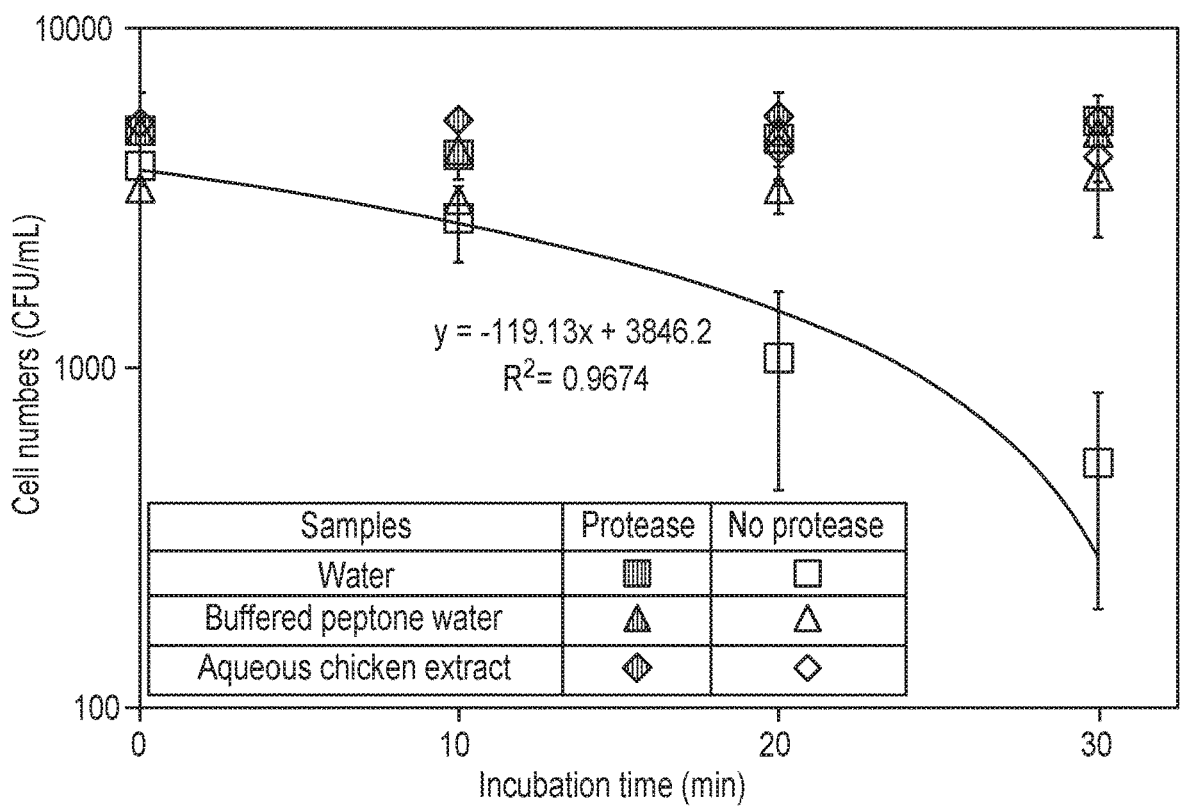
FIG. 17 shows a plot of cell population (*Salmonella*, 103 CFU/mL) growth rate under different experimental conditions.

Results are shown in FIGS. 14-17. FIG. 14 shows filtration time using different biochemical pretreatment methods. Samples, from left to right are: (1) no enzyme added control, (2) addition of 0.5% (v/v) lipase, (3) addition of 0.5% (v/v) protease, (4) addition of 0.5% (v/v) protease and lipase, (5) water control. Enzyme treatment was performed at 37° C., 200 rpm for 30 min. FIG. 15 shows variability in microfiltration times for filtered aqueous chicken homogenates, either pretreated or not pretreated with 0.5% (v/v) protease. FIG. 16 shows effects of stomacher speed and time on protein concentration and bacterial viability. Log (X/X0)

represents the ratio of the concentration of bacteria (CFU/mL) at the desired stomacher speed (X) to the concentration of the bacteria for a washing step at 0 RPM (X0). Protein content was measured with 30 seconds of stomaching time at speeds from 100 to 300 RPM in 50 RPM increments (Four replicates). FIG. 17 shows a plot of cell population (*Salmonella*, 103 CFU/mL) growth rate under different experimental conditions. Population growth rates up to 30 minutes of inoculation time were not significantly different at the 95% confidence level. A similar pattern was observed when inoculating the cells in chicken carcass rinses.

Conclusion

The addition of enzyme pretreatment reduced cell concentration and recovery time. We maintained viability of recovered microorganisms under the controlled protease incubation process. The whole process was 8 hour to detect low concentration of *Salmonella*. Further confirmation is possible on the following day by plating on selective medium.

Example 5

Rapid concentration, recovery, and detection of *Salmonella* in spinach: A protocol was developed for rapid concentration, recovery and detection of *Salmonella* in spinach at bacterial cell levels of 1 CFU/g or less. Rappaport Vassiliadis broth was used to decrease microbial background. There were no statistically significant differences between rinsing and stomaching. Spinach homogenates were concentrated approximately 500 folds within 90 minutes. More than 100% of *Salmonella* cells were concentrated and recovered from the spinach without filter degrading.

*Salmonella* was spiked onto 25 g of spinach which was dried for 10 min at room temperature. 500 g of Rappaport Vassiliadis broth was mixed with the 25 g of spinach. The Rappaport Vassiliadis broth with spiked spinach was subjected to cell enrichment and enzyme hydrolysis for 1 to 5 hours. The treated sample was then pre-filtered by flat sheet membrane before being microfiltered by $C^3D$. The sample was then centrifuged to further concentrate the pathogen cells before being pathogen identification using PCR.

Figure 18:
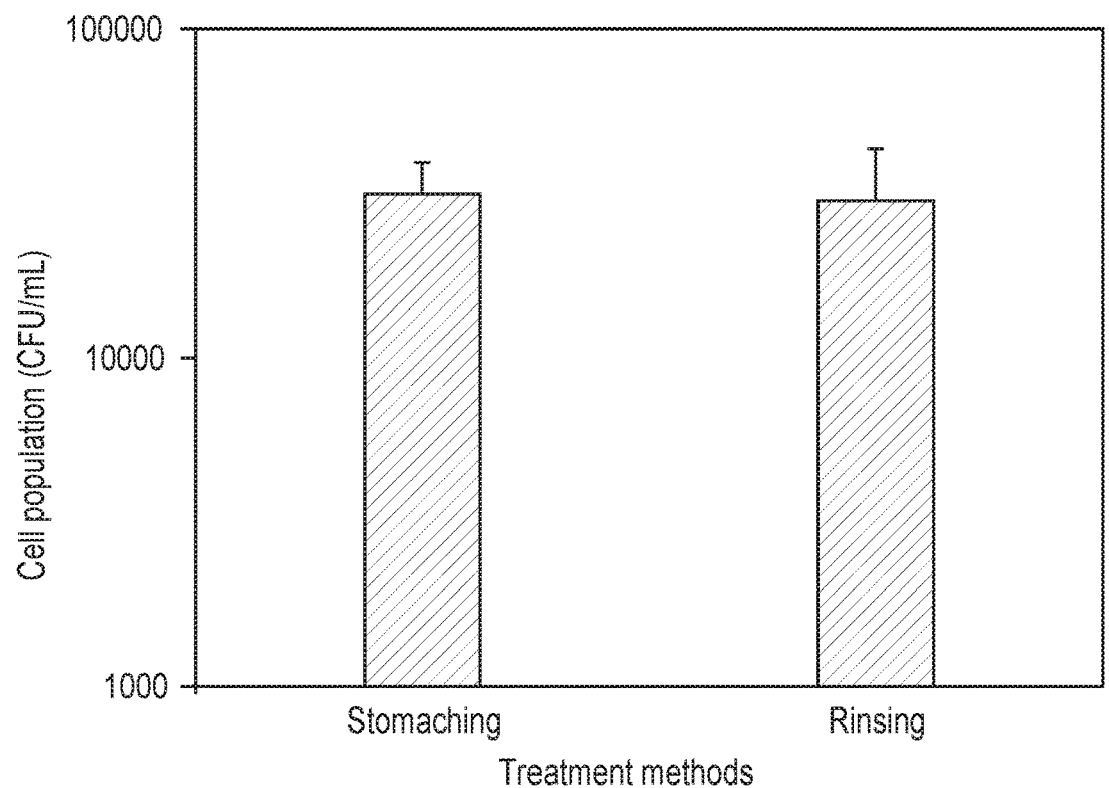
FIG. 18 graphs microbial recovery using stomaching and rinsing methods.

FIG. 18 graphs microbial recovery using stomaching and rinsing methods. Results are the average of experiments done in triplicate. The concentration of naturally occurring microbiota in buffered peptone water was observed by plating method (BHI). There were no statistical significantly differences at the 95% confidence level.

Figure 19:
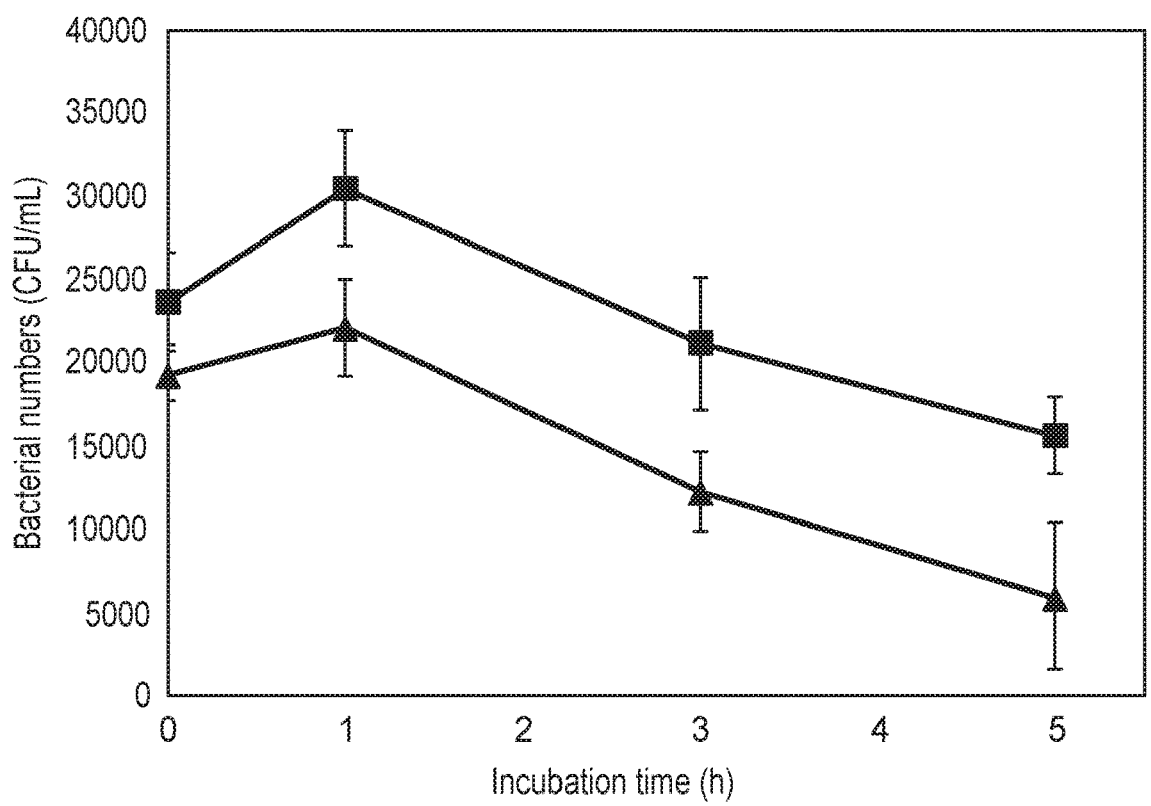
FIG. 19 shows a graph of growth rates of naturally occurring microbiota when inoculated with Rappaport Vassiliadis broth.

FIG. 19 graphs growth rates of naturally occurring microbiota when inoculated with Rappaport Vassiliadis broth. BHI (■) and XLD (▲) were used for plating. Population growth rates up to 3 h of inoculation time are not significantly different at the 95% confidence level.

Table 6 shows enumerated cell numbers on XLD selective media after 5 hours of enrichment. Results are the average of experiments done in triplicate.

Figure 20:
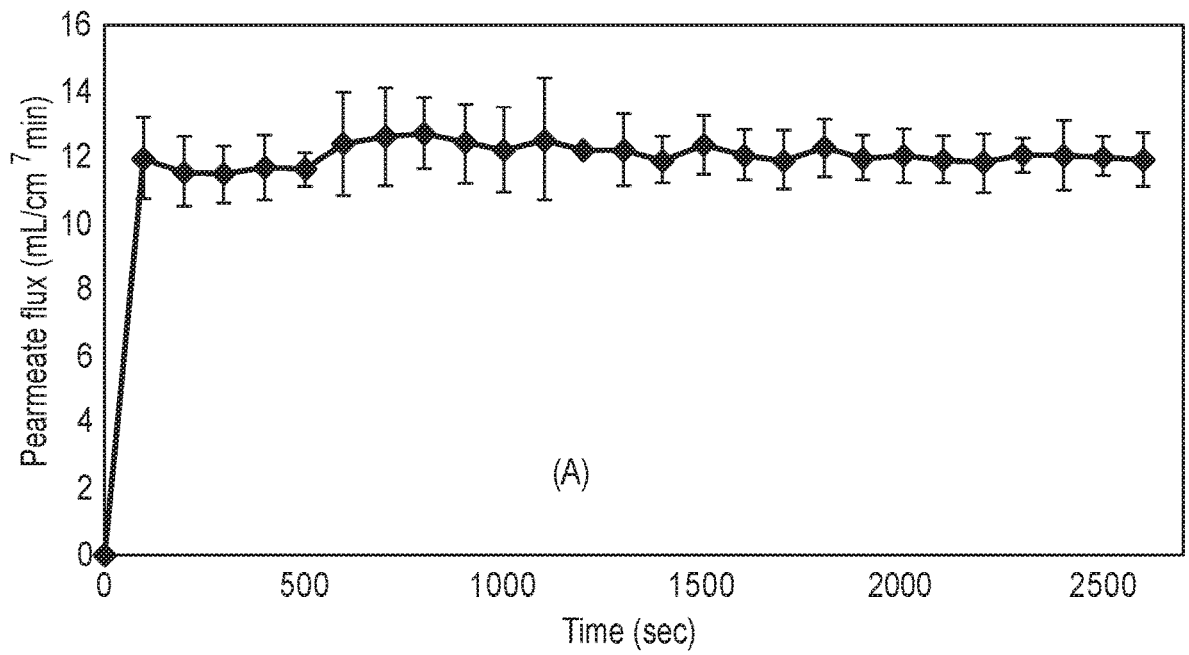
FIG. 20 shows permeate flux as a function of time during the microfiltration process by $C^3D$ at room temperature.
Figure 21:
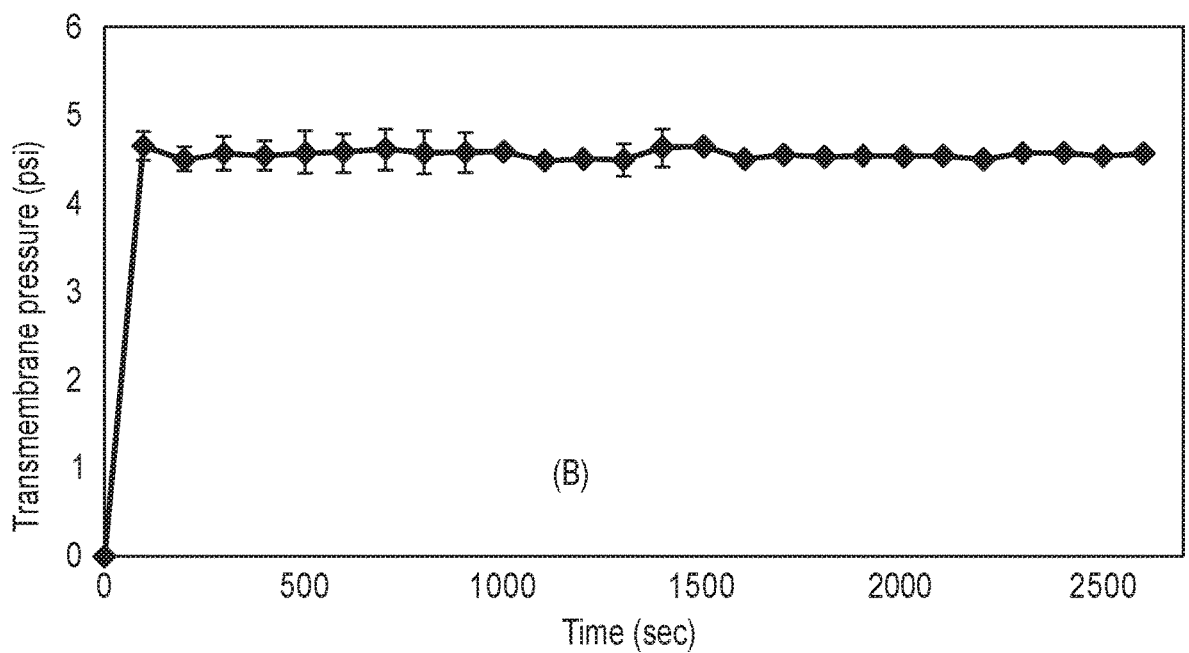
FIG. 21 shows transmembrane pressure as a function of time during the microfiltration process by $C^3D$ at room temperature

FIG. 20 shows permeate flux as a function of time during the microfiltration process by $C^3D$ at room temperature. FIG. 21 shows transmembrane pressure as a function of time during the microfiltration process by $C^3D$ at room temperature. The speed of motor 1 and motor 2 were kept constant at 100% and 20% respectively.

The entire process (sample preparation, concentration, recovery and PCR based detection) to detect <1CFU/g of *Salmonella* from spinach was completed in 9 hours. Further confirmation of results using standard methods was obtained in 20 hours using enrichment and plating on a selective medium.

Example 6

Rapid concentration and recovery of microorganisms from water samples for metagenomic analysis: We investigated new methods that have the potential to reduce the microbial detection time to less than 5 hours from a large volume water sample (5 to 10 L). For the cell concentration and recovery steps, the water was pre-filtered to remove large particles and then concentrated using microfiltration before being finally concentrated using $C^3D$.

Figure 22:
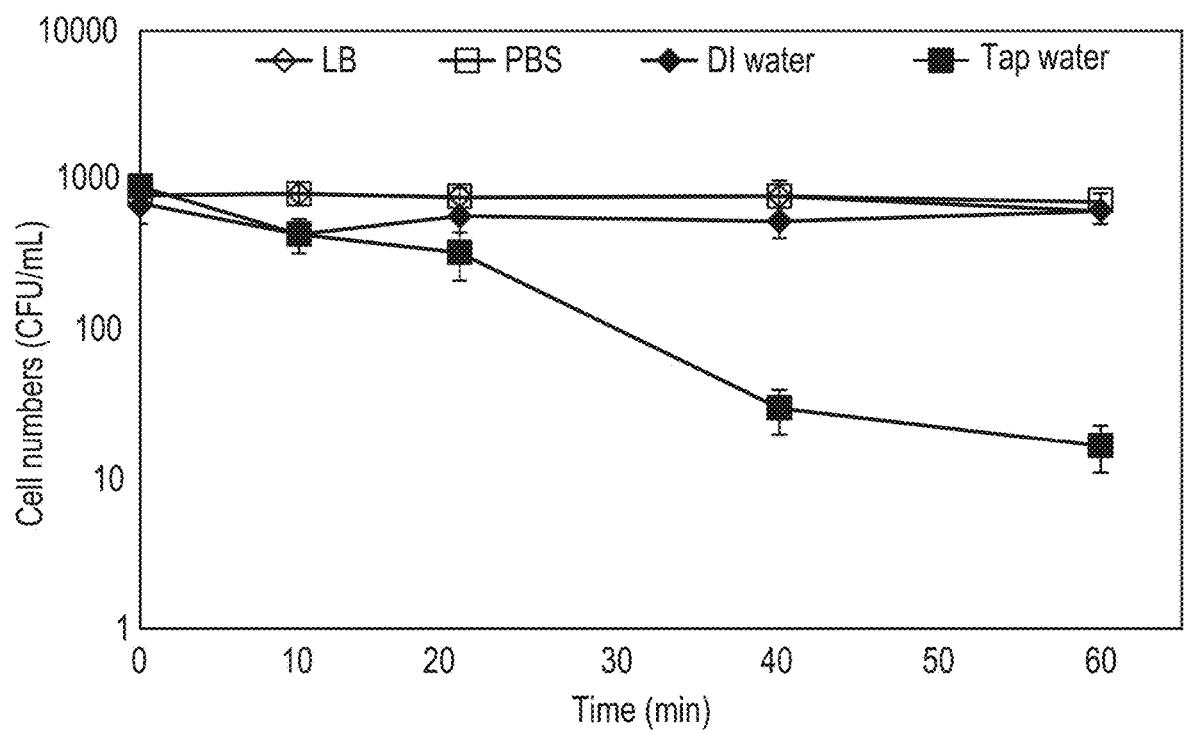
FIG. 22 shows *E. coli* expressing GFP cell numbers observed fusing 4 diluents.
Figure 23:
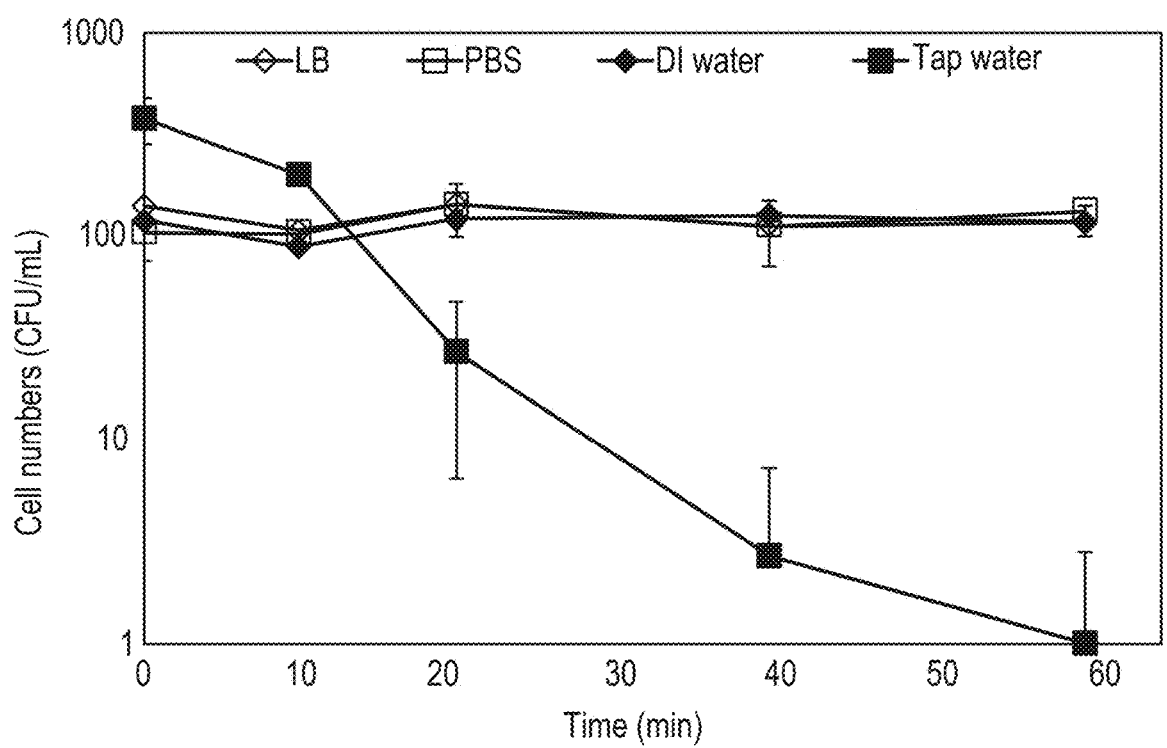
FIG. 23 shows *Salmonella Enteritidis* PT 21 cell numbers observed using 4 diluents.

Microbial viability was tested in 4 different diluents, LB, PBS, deionized water, and tap water. Initial concentration of spiked microorganism was adjusted to 102 CFU/mL. Microorganisms tested were *Escherichia coli* expressing green fluorescent protein (GFP) and *Salmonella Enteritidis* PT 21 plated on LB and Chromo agar media, respectively. FIG. 22 shows *E. coli* expressing GFP cell numbers observed for the 4 diluents and FIG. 23 shows *Salmonella Enteritidis* PT 21 cell numbers observed for the 4 diluents.

Concentration of naturally occurring microbiota in tap water was assessed at each step of the cell concentration and recovery process outlined above. For each starting cell level, three replicate experiments were conducted. On average, 103 and 7×103 CFU/g of naturally occurring microbiota in tap water were detected from each step by incubation on BHI agars, after 24 hours. Results are shown in Table 7.

TABLE 7

| | | Cell concentration and recovery process | | |
|---|---|---|---|---|
| | Type of media | Original sample (CFU/g) | Large volume concentration (CFU/g) | $C^3D$ (CFU/g) |
| Test 1 | BHI | 0 | 2880.0 | 19200.0 |
| Test 2 | BHI | 0 | 146.7 | 1633.3 |
| Test 3 | BHI | 0 | 386.7 | 1300.0 |

TABLE 6

| | | | | Process for Microbial Concentration | | | | | | | | |
|---|---|---|---|---|---|---|---|---|---|---|---|---|
| Type of Selective Media | Spiked cell | Original sample (CFU/g) | Weight (g) | After 5 h Enzyme Incubation (CFU/g) | Weight (g) | After Nylon filtration (CFU/g) | Weight (g) | After $C^3D$ (CFU/g) | Weight (g) | After Centrifugation (CFU/g) | Weight (g) | Rec. (%) |
| 1 XLD | 3.6 | 0 | 500.0 | 0 | 500.0 | 0 | 473.5 | 250.0 | 11.2 | 4150.0 | 1.3 | 1515.4 |
| 2 XLD | 6.8 | 0 | 500.0 | 0 | 500.0 | 0 | 476.9 | 550.0 | 11.0 | 5150.0 | 1.5 | 1136.0 |
| 3 XLD | 3.4 | 0 | 500.0 | 0 | 500.0 | 0 | 470.0 | 400.0 | 12.0 | 4000 | 1.5 | 1785.7 |
| Average | 4.6 | 0 | 500.0 | 0 | 500.0 | 0 | 473.5 | 400.0 | 11.4 | 4433.3 | 1.4 | 1479.1 |

After large volume cell concentration, the initial sample (10 L) was reduced down to 55 mL after 2 h. 55 mL of concentrated sample was further reduced down to 0.5 mL by in-house microfiltration module. Concentrated tap water after microfiltration was significantly more turbid than normal tab water. It was apparent that microfiltration of tap water resulted in concentration of ion, bacteria and other particles. However, after concentration of sterilized DI water, sample color was not changed and there were no recovered microorganism. The whole procedure from sample collection to microfiltration finished within 2.5 h.

Finally, concentration of naturally occurring microbiota from 10 L of a Wabashi river water sample and 5 L of vegetable wash sample was investigated. The sample was vacuum filtered using glass microfiber membrane (2.7 µm) before microfiltration on large volume concentrator and C3D using polyethersulfone (0.2 µm) hollow fiber membranes. The resulting recovered sample was plated on BHI medium. Vegetable wash was treated by chlorine (14.0 ppm).

Large volumes of water samples (5 to 10 L) can be concentrated through a 3 steps filtration approach. For concentration of microorganisms naturally occurring at low levels, and their recovery at low volume with enough cells for detection using gold standard methods (plating), fast detection approaches (PCR) or metagenomic analysis. This approach can also be used to access sterilization of water after treatment for possible re-use.

Example 7

Use of an automated continuous cell concentration device (c3d) for rapid concentration and recovery of *salmonella* in ground turkey: The Centers for Disease Control and Prevention reported *Salmonella* species to be leading cause of foodborne illness hospitalizations and deaths in the United States. Commercial poultry is one of the fastest growing sectors of the agricultural industry and as a significant reservoir for *Salmonella* an increase in poultry consumption increases the potential risk of *Salmonella* induced disease. Detection of pathogens is critical for reducing foodborne disease outbreaks and disease. Culture-based non-selective and selective enrichment require as much as two days or more to reach minimum cell levels necessary to be detected by current rapid detection methods. These techniques are often laborious while waiting days for test results has a negative economic impact on poultry processors. Rapid, precise and accurate detection methods are in demand from regulators, poultry processors and researchers who are looking for a faster alternative to the standard enrichment based methods.
Methods Pretreatment: A 25 g of sample ground turkey (93/7 lean/fat) was transferred to a plastic bag and pressed by hand from outside the bag into a roughly 1 cm thick square and allowed to reach room temperature. Following that, a 250 µL volume of *Salmonella Enteritidis* at different concentrations used in this work was spread evenly over the surface of the turkey square. The square was then folded along its median and gently massaged by hand back to the original 1 cm thickness. The folding and massaging was then repeated. The spiked ground turkey was placed in a Filtra Bag, mixed with 225 mL of saline solution (0.9% (w/v)) or Rappaport Vassiliadis (RV) broth and homogenized in a Seward Stomacher 400 circulator at 100 rpm for 30 s. The aqueous fraction was then transferred to a 500 mL glass bottle and incubated at 37° C. for 20 to 180 min. Three equal fractions of the broth were then individually filtered through one 2.7 µm GF/D glass filter each and recombined. After that, the broth was incubated at 200 rpm and 37° C. for 20 min with a final loading of 0.3 mg/mL Promod 439L. All the above steps were carried out under aseptic conditions.

Concentration: The resulting liquid was processed through the automated C3D begun by adding liquid to the sample reservoir and initiating the LabVIEW control program. Once the sample has been concentrated down to ~5 mL, 10 mL of 0.002% (v/v) Tween 20 was added to the sample reservoir aid in sample elution. The concentrated liquid was collected, added to 1.5 mL Eppendorf tubes, and spun down to be recovered in ~0.5 mL of final concentrated sample.

Figure 24:
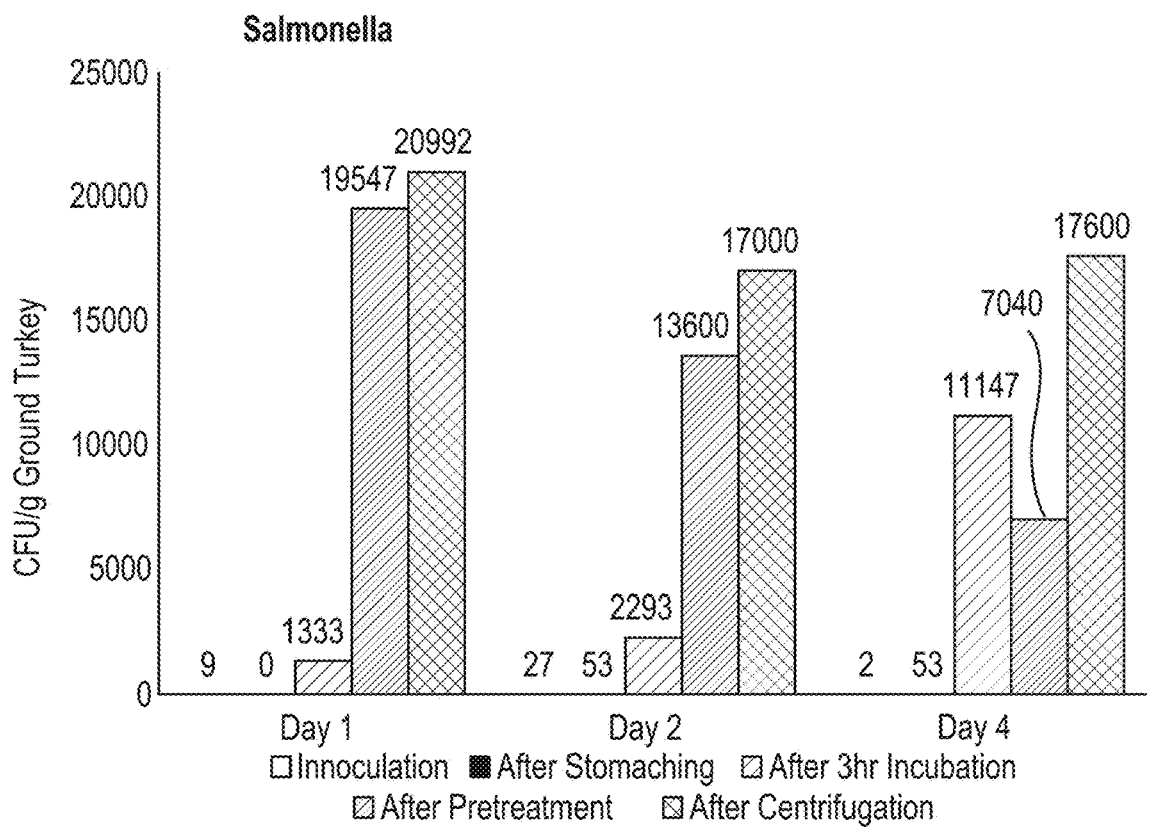
FIG. 24 illustrates CFU/g of ground turkey detected at various stages of pretreatment and concentration.
Figure 25:
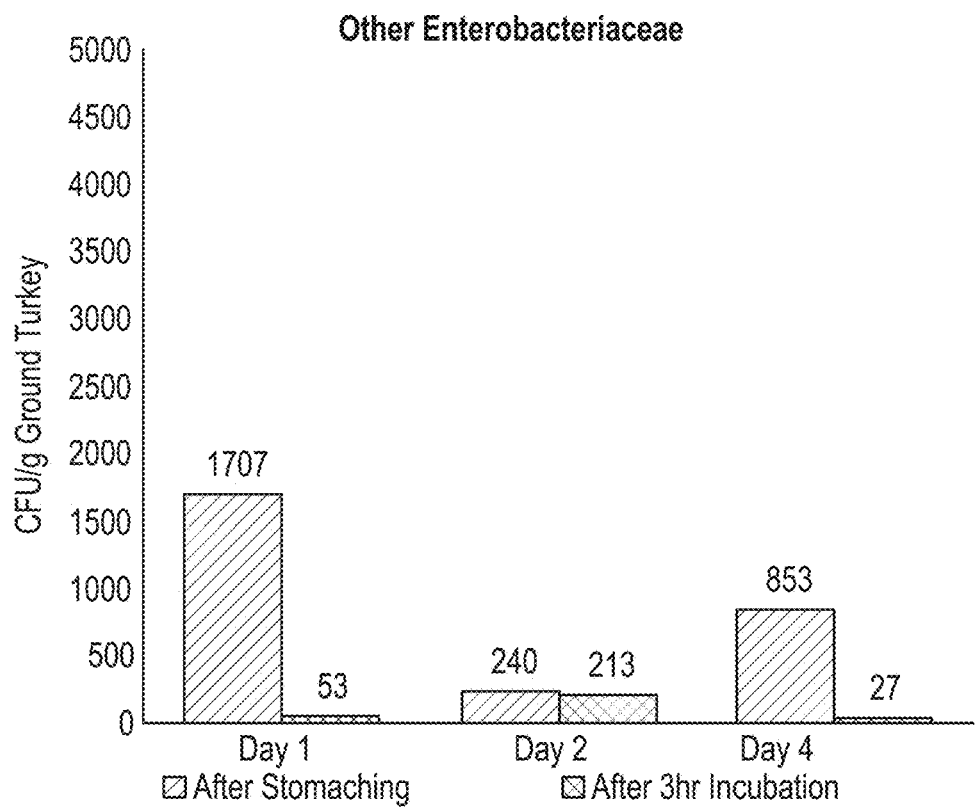
FIG. 25 depicts CFU/g of other enterobacteriacae detected at various stages of pretreatment and concentration.

Detection: The recovered sample can now be analyzed for *Salmonella* by plating, PCR or possibly other methods requiring a small volume of concentrated cells.
Results CFU per gram of ground turkey was measured by plating at various stages of pretreatment and concentration. FIG. 24 illustrates CFU/g of *Salmonella* detected in ground turkey at various stages of pretreatment and concentration. FIG. 24 depicts CFU/g of other Enterobacteriacae detected at various stages of pretreatment and concentration. FIG. 24 shows a significant increase of *Salmonella* CFU while the FIG. 25 shows suppression and even elimination of other Enterobacteriaceae at simultaneous steps in pretreatment. ChromAgar selective plates were used to detect and quantify CFU amounts. These plates showed the increase of *Salmonella* and simultaneous suppression of other Enterobacteriaceae colonies. *Salmonella* was detected by PCR from three final samples of concentrated cells.
Conclusion Pre-filtration using the glass microfiber filter before enzyme hydrolysis coupled to a short enrichment step minimizes loss of target microbial recovery from ground turkey spiked at low concentrations (101CFU/g). Under these conditions, recoveries of 100% or higher *Salmonella* cells from ground turkey were obtained. The whole process from sample processing to PCR detection may take 8 hours. Further confirmation by plating on selective medium may be achieved in 24 h.

Example 8

Optimization of Pretreatment Steps Applied to a Microfiltration System for Rapid Pathogen Detection: With a growing number of consumers in the American market and with food production at an all-time high, food safety is a huge priority for both consumers and corporations everywhere. Recently, the Laboratory of Renewable Resources Engineering (LORRE) at Purdue University developed a Continuous Cell Concentration Device (C3D) that has the potential to reduce the amount of time required to detect foodborne pathogens. The $C^3D$ utilizes microfiltration to produce a smaller, concentrated sample, which facilitates the identification of microbial populations. Before cell concentration, food samples are subjected to a pretreatment process that utilizes enzymes to prevent protein aggregation and fouling of the hollow-fiber membranes used in the $C^3D$. We investigated the role of enzymes to enable microfiltration and ensure recovery of *Escherichia coli* (*E. coli*) in ground beef solutions. We are working to quantify the effect of enzyme pretreatment on hollow-fiber membrane flux and *E. coli* cell viability. Preliminary results show that enzyme pretreatment effectively breaks down large proteins and prevents fouling of the hollow-fiber membrane. Thus, enzyme pretreatment, coupled with C³D technology, begins to address the critical need for rapid pathogen detection.

Microfiltration is a rather simple method to reduce large samples to a small volume and effectively increase the cell concentration. Once concentrated, the cell solution can be probed for the presence of pathogenic organisms through the method of plating. This experiment aimed to develop approaches for pre-filtration and enzyme hydrolysis of ground beef, which are critical to concentrating and recovering microorganisms via microfiltration. Once the process is optimized, the presence or absence of an effect of enzyme treatment on cell viability can be determined.

Food Solution Preparation for C3D Processing: Approach: *E. coli* cell recoveries and microfiltration rates are determined from C3D processed samples. Cell recovery is determined by plating, and when compared to non-enzyme treated samples, provides insight into the effect of enzyme treatment on cell viability. Microfiltration rates provide an indication of the effectiveness of the pretreatment process, as well as the rate at which the performance of the microfiltration module degrades after consecutive trials. Steps for preparation and recovery included: 1. homogenized ground beef solution was spiked with 2 mL 103-104 CFU/mL *E. coli* O157 (GFP) to simulate a contaminated sample; 2. a short enrichment period followed inoculation to enable enzyme hydrolysis; 3. the pre-filtration step used a glass microfiber filter to remove large colloids and enable microfiltration with the C3D; 4. the short enrichment period was repeated since it is typical for >40% of cells to be lost from pre-filtration; 5. finally, the sample was concentrated in the C3D and recovered.

Optimization of the Pretreatment Process Approach: Previous experiments with turkey homogenates have suggested that reversing the order of the pretreatment process (pre-filtration prior to enzyme hydrolysis) reduces the loss of cells. In this experiment, cell recoveries were determined by plating after each pretreatment step (pre-filtration and enzyme hydrolysis) in order to optimize the pretreatment process. Homogenized ground beef solution was enriched for 3 hours to enable cell growth prior to pretreatment. Incubation with the enzyme (enzyme hydrolysis) was reduced to 20 minutes to reduce the time at which the cells were exposed to the protease. Pathway 1: Pre-filtration was conducted prior to enzyme hydrolysis. Pathway 2: Enzyme hydrolysis was conducted prior to pre-filtration.

Figure 26:
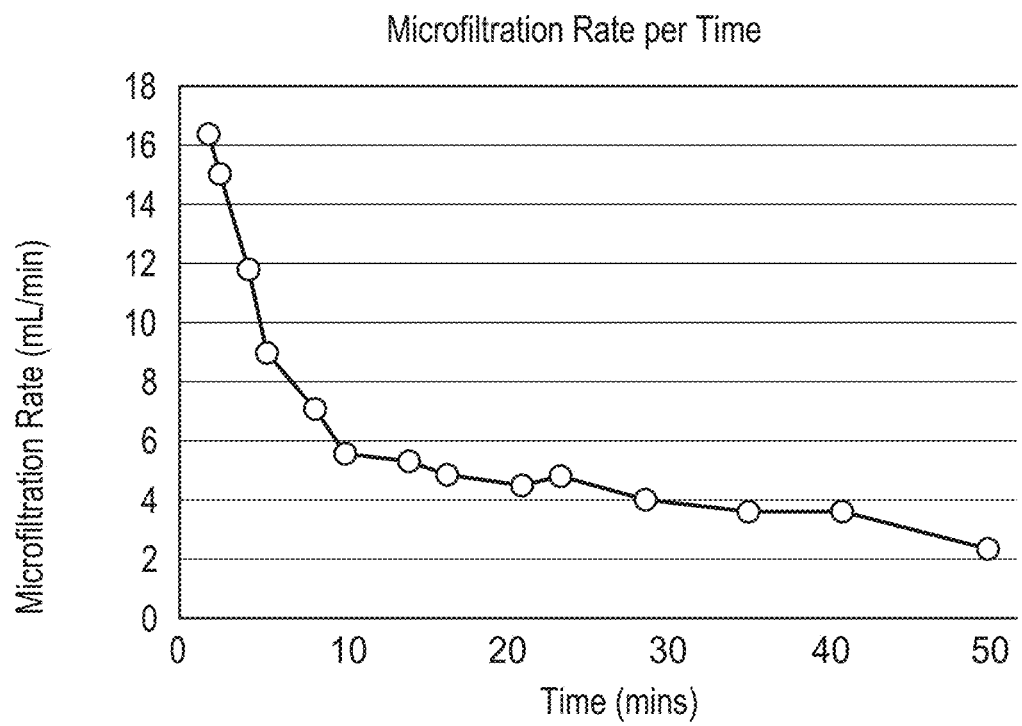
FIG. 26 shows microfiltration rate over time during $C^3D$ processing.
Figure 27:
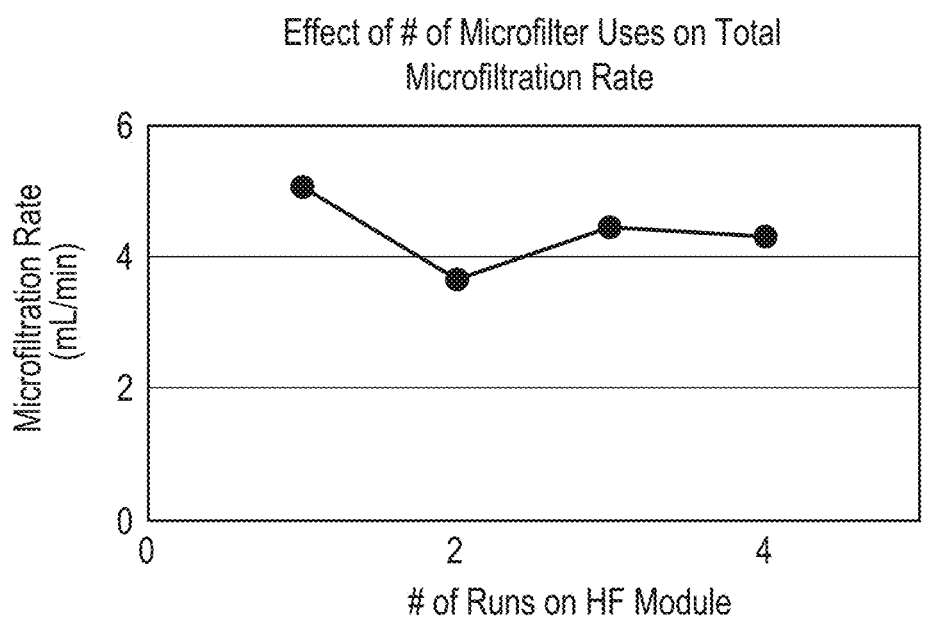
FIG. 27 shows the effect of multiple runs on microfiltration rate.
Figure 28:
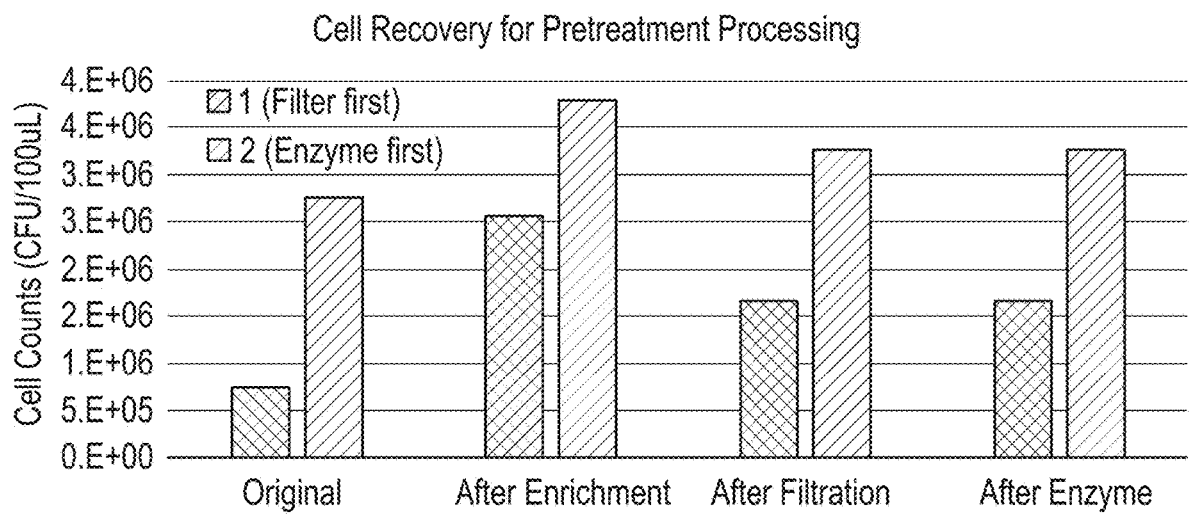
FIG. 28 shows cell recovery in pretreatment processing for pre-filtration before enzyme hydrolysis or after enzyme hydrolysis.
Figure 29:
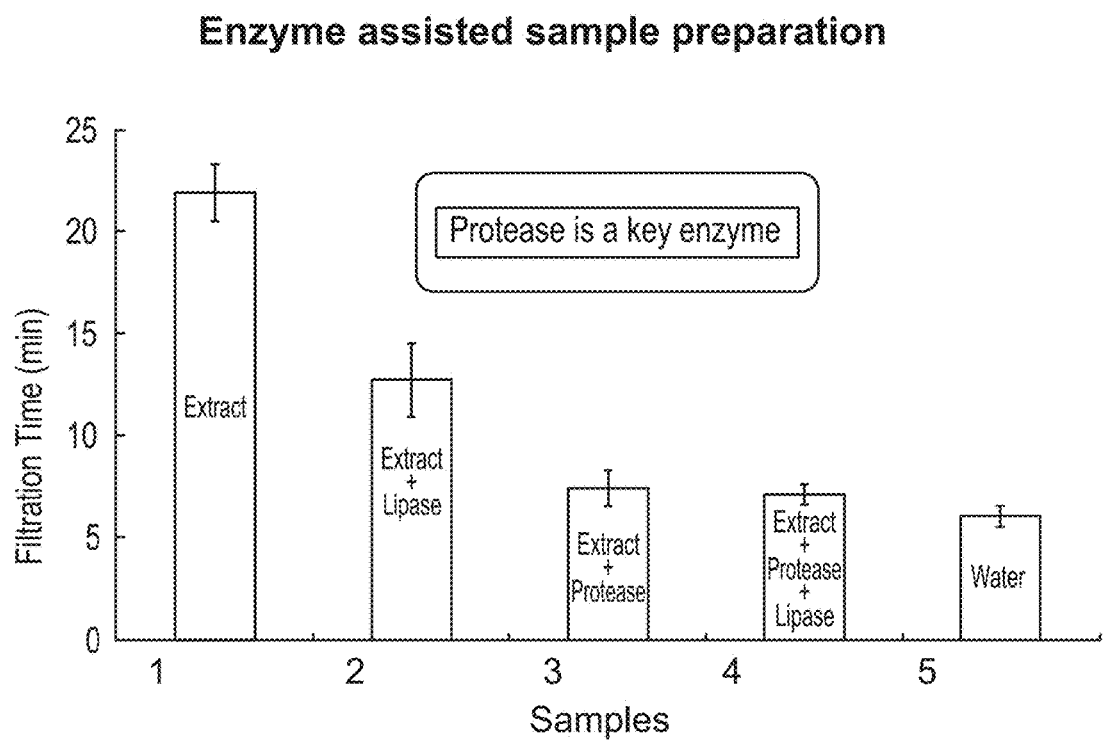
FIG. 29 shows filtration times for extract with various enzyme treatments compared to filtration time for untreated extract and water.

RESULTS: FIG. 26 shows microfiltration rate over time during C³D processing. FIG. 27 shows the effect of multiple runs on microfiltration rate. FIG. 28 shows cell recovery in pretreatment processing for pre-filtration before enzyme hydrolysis or after enzyme hydrolysis. The effects of pre-filtration and enzyme hydrolysis ordering are also shown in Table 8.

TABLE 8

Preteatment Process Data

| | Pathway 1 | Pathway 2 |
|---|---|---|
| % Loss from Pre-Filtration | 87.8% | 25.8% |
| Pre-filtration Time (mins) | 30 | 10 |

Example 9

Figure 31:
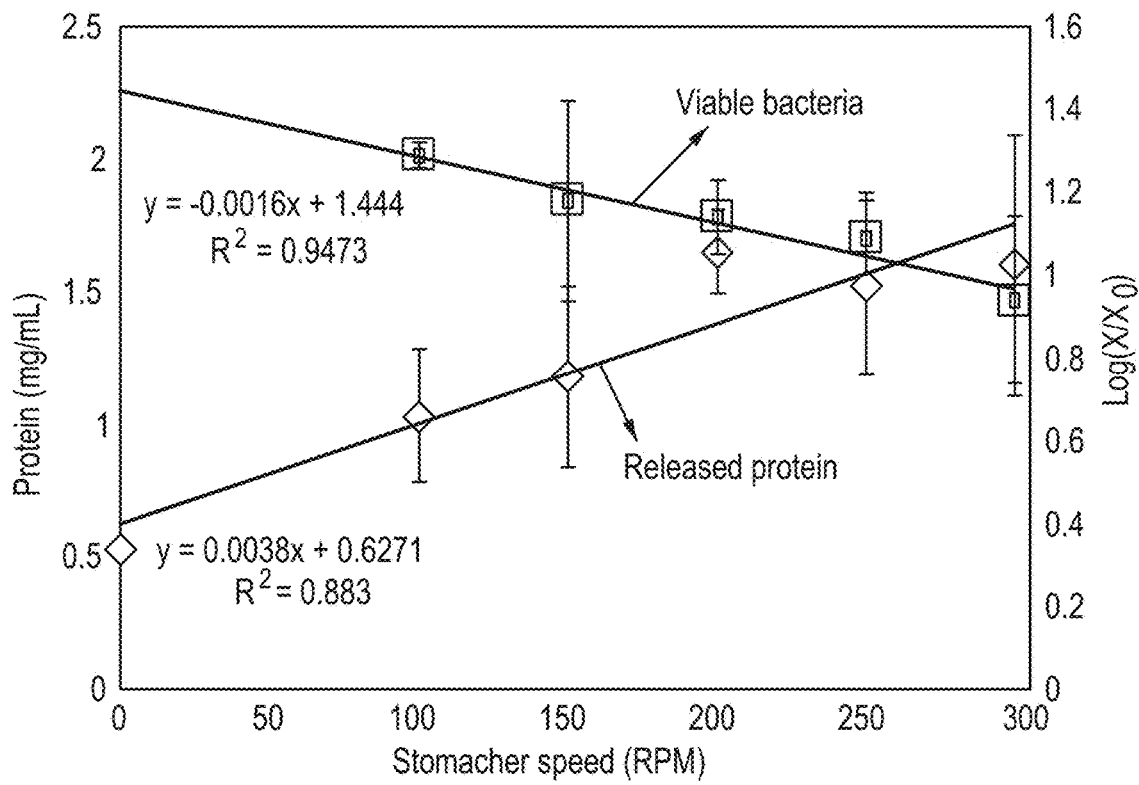
FIG. 31 shows effects of stomacher speed on protein concentration and bacterial viability.

Accelerating sample preparation through enzyme-assisted microfiltration of *salmonella* in chicken extract: Microfiltration of chicken extracts has the potential to significantly decrease the time required to detect *Salmonella*, as long as the extract can be efficiently filtered and the pathogenic microorganisms kept in a viable state during this process. We examined conditions that can enable microfiltration by adding endopeptidase from *Bacillus amyloliquefaciens* to chicken extracts or chicken rinse, prior to microfiltration with fluid flow on both retentate and permeate sides of a 0.2 lm cutoff polysulfone and polyethersulfone hollow fiber membranes. After treatment with this protease, the distribution of micron, submicron, and nanometer particles in chicken extracts was changed so that the size of the remaining particles corresponded to 0.4-1 lm. Together with alteration of dissolved proteins, this change helps to explain how membrane fouling might be minimized because the potential foulants are significantly smaller or larger than the membrane pore size. At the same time, we found that the presence of protein protects *Salmonella* from protease action, thus maintaining cell viability for later detection. Concentration and recovery of 1-10 CFU *Salmonella*/mL from 400 mL chicken rinse was found to be possible in less than 4 h, with the microfiltration step requiring less than 25 min at fluxes of 0.028-0.32 mL/cm2 min. The entire procedure—from sample processing to detection by polymerase chain reaction—could be completed in 8 h.

Materials and Methods

Microorganism and enzymes *Salmonella enterica* serovar *enteritidis*, from 4% dimethyl sulfoxide freezer stocks stored at −80° C., was grown overnight in 5 mL BBL™ brain heart infusion (BHI, Sparks, Baltimore, MD) broth at 37° C. with shaking at 200 rpm. BBL™ BHI agar (Sparks) was used as a nonselective medium for the growth of the naturally occurring microbiota from skinned chicken meat. Xylose lysine deoxycholate (XLD) agar (VWR, Batavia, IL) was used to further enumerate *Salmonella* cells, although confirmation of the presence of *Salmonella* sp. required polymerase chain reaction (PCR). Following spread plating, all plates were incubated overnight at 37° C. Protex™ 7L (bacterial neutral protease obtained from *Bacillus amyloliquefaciens*) and G-ZYME G999 (lysophospholipase obtained from *Aspergillus niger*) were provided by Genencor Division of Danisco (Palo Alto, CA).

Microbial viability was determined by spread plating in selective media and obtaining colony counts on plates. Aqueous chicken homogenates were prepared from store purchased chicken legs using deionized water. The deionized water consisted of city tap water processed first through a reverse osmosis system, then through a Barnstead E-pure system (comprised of four filters: micropure, high capacity DI, organic-free, and ultrapure deionized water to a final rating of 17 ohms) for stomaching, filtering, and characterizing the samples. Water (225 mL) was added to raw chicken (25 g) in a sterile filter bag (Filtra, Fischer Scientific, Waltham, MA) and stomached at settings between 0 and 300 rpm for 0.5-1 min using a Seward.5 StomacherVR 400 Circulator (Port Saint Lucie, FL). The pH of the stomached samples was pH 6.8. Chicken carcass rinses were obtained from whole chicken (2.960.1 kg) purchased in a grocery store by mixing a carcass with 400 mL of sterile buffered peptone water (BPW) in a sterile bag and inverting the carcass back and forth for 1 min. The wash water included blood as was evident by the red color of the wash and noted previously by Cheryan. Protein buffered the extract at pH 6.8. Six extracts derived from individual chicken samples (three with inoculated samples and three without inoculation) were tested.

Compression and shearing forces are needed to release the bacteria. Measurements were performed at 0, 100, 150, 200, 250, and 300 rpm and at 0, 30, and 60 s for 50 mL of aqueous chicken homogenates. A sample (100 lit) of stomached solution from each condition was spread on a BHIagar plate and incubated overnight at 37° C. Protein concentrations were quantified by the Pierce (Thermo Scientific, Rockford, IL) bicinchoninic acid protein assay using bovine serum albumin as a standard and 100 μL samples volumes taken from the stomacher bag. The pH was measured by a Beckman 690 pH temp mV ISE Meter (Beckman Coulter, Brea, CA). Stomaching at 100 rpm for 30 s was used in subsequent runs to minimize protein release while detaching microorganisms (FIG. 31). Stomaching provided a slurry that resembles material from a blender. FIG. 31 shows effects of stomacher speed on protein concentration and bacterial viability. Log $(X/X_0)$ represents the ratio of the concentration of bacteria (CFU/mL) at the desired stomacher speed (X) to the concentration of the bacteria for a washing step at 0 rpm (X0). Four biological replicates (50 mL aqueous chicken homogenates) were used in this experiment. Protein content was measured for 30 s of stomaching time at speeds from 100 to 300 rpm in 50 rpm increments.

Aqueous chicken homogenates were treated with either endopeptidase or lysophospholipase before prefiltration through a glass microfiber membrane (2.7 μm) cutoff (Whatman, GE Healthcare UK, Amersham, UK). Endopeptidase (Protex 7L) was added to the homogenate at 0.5% (v/v) (equal to 0.27 mg/mL). Protex 7L is formulated for reducing viscosity of solutions of fish or chicken by-products where pH adjustment is not feasible due to the self-buffering capacity of the protein. GZYME G999 (lysophospholipase), flask (Pyrex, catalog no. 5340, NY) Buchner funnel (catalog no. 60243, Coors Tek, Golden, CO) and glass microfiber membranes (125 mL/1 filter paper) were used.

The particle size measurements for the crude aqueous chicken homogenates and those treated with protease and prefiltration were carried out by dynamic light scattering using a Malvern Instrument Zetasizer 3000. The detection angle was 173°. The intensity-weighted mean hydrodynamic size and the width of the particle size distribution were obtained by analyzing the autocorrelation function. Between 10 and 20 measurements were made at 23° C. for each sample with an equilibrium time of 5 min.

HF modules consisting of either 12 PS fibers or 45 PES fibers were used in an automated pumping and recycle system described in a previous article. The modules containing 12 PS fibers were fabricated in our laboratory. The individual HFs were 0.030 cm in outside diameter, with a 0.028 cm inner diameter and 27 cm length. For 12 fiber modules, the resulting surface area per module was 28.5 cm2.

The commercial fiber modules were purchased from Spectrum Labs (Midkros HF module, catalog D02-P20U-05-N, Rancho Dominguez, CA) and consisted of PES HFs with 140 cm2 surface area per module, 0.50 mm inner diameter, 20 cm length, and a nominal pore cutoff of 0.2 mm, with 45 fibers per module. Properties of the fibers are summarized and compared with the in-house constructed modules in Table 9.

TABLE 9

Properties of HF modules used in this work.

| | Fiber Characteristics | | | | Module Characteristics | | | | At Inlet of Individual Fiber | | |
|---|---|---|---|---|---|---|---|---|---|---|---|
| | | | | | Total for All Fibers | | | | | | |
| Module | ID (cm) | OD (cm) | L (cm) | Surface Area (Based on ID) (cm²/fiber) | Number of Fibers | Cross-sectional Area for Flow cm² (Based on ID) | Dead Vol. (cm³) | Surface Area (cm²) | Flow Rate of Water (mL/min) | Interstitial Velocity (cm/s) | Reynolds Number (Re) |
| A: In-house, 12-fiber PS* | 0.028 | 0.036 | 27 | 2.37 | 12 | 0.0074 | 0.199 | 28.5 | 25.5 | 57.6 | 160 |
| B: Commercial PES †, ‡ | 0.050 | — | 20 | 3.14 | 45 | 0.0883 | 1.77 | 141. | 34 | 6.4 | 32 |

*Li et al., 2013.
† At room temperature.
‡ Midikros Modules (Spectrum Labs)

added as 0.5% (v/v) (equal to 0.03 mg protein/mL), is used to disrupt protein emulsions and improve filtration rates. Aqueous chicken homogenate samples were incubated with the enzymes at 37° C. with initial tests carried out for 30 min, with subsequent optimization resulting in selection of protease alone, and a 10 min incubation prior to filtration through a glass microfiber filter. Protein concentrations of stock solutions of Protex 7L (protease) and GZYME G999 (lipase) were 54 and 5.5 mg/mL, respectively, as quantified by the Pierce bicinchoninic acid protein assay, and activities were 1,600 AU/g at pH 6.5 and 458C and 1,000 U/g at pH 4.5 and 55° C., respectively (manufacturer's literature). The enzymes were not inactivated prior to plating.

All samples were prefiltered after the enzyme treatment and before microfiltration using a sterile glass microfiber 2.7 μm cutoff filter to remove colloidal particles while minimizing retention of microorganisms so that they could be collected in the filtrate. For the prefiltration, 1,000 mL filter The flow rates utilized during the microfiltration step gave fiber inlet pressures ranging from 0.2 to 1.4 bar so that the pressure was lower than the pressure limit of the membranes, i.e., 2 bar. This coincided to a volumetric flow rate of 25.5 mL/min, and a linear velocity of 57.6 cm/s per fiber for the in-house module, and 34 and 6.4, respectively, for the commercial module (Table 9). The linear velocities were calculated by dividing the flow rate by the cross-sectional (open) area of the 12 and 45 HF modules, respectively. The flow rate at the inlet corresponded to the maximum linear velocity because the fluid permeated through the HF membrane wall along the length of the fiber.

The Reynolds number at the inlet of the HFs in the two modules was calculated to be 160 and 32, respectively, and corresponded to a laminar regime. The flow rate decreased by about 50% as the fluid passed through the HF (Table 10). Hence, the Reynolds number decreased as a function of distance from the FIF inlet and stayed in the laminar range as fluid passed through the length of the membrane. Flux rates ranged from 0.035 to 0.42 mL/cm2 min, with the highest net fluxes corresponding to water and 12 fiber modules, and the lowest for chicken carcass rinse and the 45 fiber module (Table 3). The flux for carcass rinse decreased by 40%-50% over the course of microfiltering 140 mL, whereas the fluxes for water only were nearly the same at the beginning and end of a run.

Figure 32:
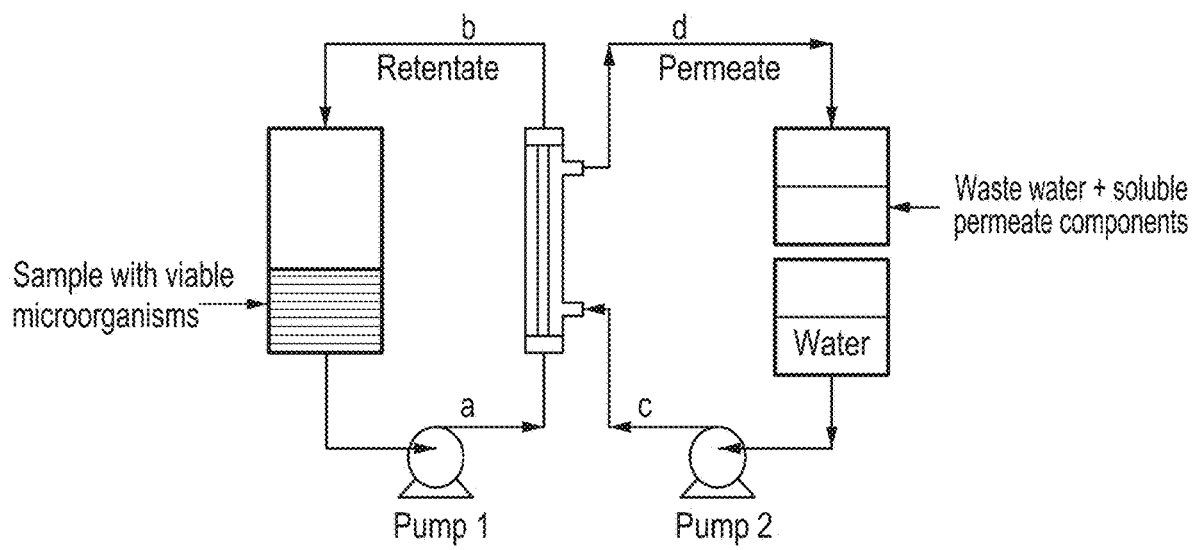
FIG. 32 shows a schematic diagram showing flow streams on retentate and permeate sides.

An automated sequence of microfiltration, sample recovery, cleaning, and sterilization was carried out each time a sample was processed, thus enabling multiple uses of the same module. This is an important consideration because membrane (module) cost is a major contributor to the cost of processing the sample. Runs for the 12 and 45 fiber modules for aqueous chicken homogenates and chicken carcass rinses were carried out, respectively, at net permeate flow rates that decreased from 9 to 5 mL/min for the 12 fiber module and 4 to 16 mL/min for the 45 fiber module over the time course of a microfiltration run (column d-c in Table 10). These correspond to measured volumes at the inlet and outlet of the retentate and permeate sides (FIG. 32). FIG. 32 shows a schematic diagram showing flow streams on retentate and permeate sides. The sample contains living (viable) microorganisms that are recovered in a concentrated form at the completion of the microfiltration step. Pumps 1 and 2 are independently controlled.

inoculated in DI water with and without addition of protease. The recovered concentrate was plated and counted after 20 h.

Chicken carcass was mixed with 400 mL of sterile BPW in a sterile bag at room temperature by inverting the carcass back and forth for 1 min, with a resulting pH of 6.8. The carcass rinses (400 mL) obtained after addition of *Salmonella* at 1-10 CFU/mL were cultured (i.e., enriched) by incubating at 37° C., 200 rpm, for 3 h, after which protease was added (diluted to 0.5% volume stock solution/volume-buffered peptide water) and incubated for an additional 10 min. After 3 h, the rinse was prefiltered. This was followed by microfiltration using a 45 fiber module. About 10 mL of the concentrated samples, recovered from the microfiltration step, were centrifuged at room temperature for 5 min at 14,000 rpm (Centrifuge 5418, Eppendorf, Hamburg, Germany). The resulting concentrate was resuspended in a final volume of 1.0 mL of sterile DI water. Concentrated samples were then plated on selective media for *Salmonella* to estimate the total number of viable microorganisms.

Two different methods were used for DNA extraction from the concentrated samples to test for the effect of PCR inhibitors on *Salmonella* detection. One milliliter of sample was microwaved at 1,250 W using a Model NN-H965WF microwave (Panasonic, Osaka, Japan) for a total of 3 min, vortexed briefly, and then centrifuged at 14,000 rpm for 1

TABLE 10

Flows on Retentate and Permeate Sides of HF Membrane Module (Based on Microfiltration of 140 mL)

| Fluid | Module | Inlet Pressure (Bar) | Elapsed Time (min) | Flow (mL/min)* | | | | | | Net Flux (mL/cm² min) |
|---|---|---|---|---|---|---|---|---|---|---|
| | | | | a | b | a – b | c | d | d – c | |
| Water | A: 12 fiber | 1.36 | — | 25.5 | 13.5 | 12.0 | 18.0 | 30.0 | 12.0 | 0.42 |
| | B: 45 fiber | 0.20 | — | 34.4 | 16.8 | 17.6 | 14.5 | 32.0 | 17.5 | 0.12 |
| Carcass rinse ± enzyme | A: 12 fiber | 1.36 | 2.5 | 20.0 | 11.0 | 9.0 | 25.0 | 34.0 | 9.0 | 0.32 |
| | | 1.36 | 22.5 | 11.0 | 6.0 | 5.0 | 20.0 | 25.5 | 5.0 | 0.18 |
| | B: 45 fiber | 0.27 | 1.6 | 32.0 | 16.0 | 16.0 | 13.0 | 29.0 | 16.0 | 0.113 |
| | | 0.27 | 16.2 | 36.0 | 32.0 | 4.0 | 16.0 | 20.0 | 4.0 | 0.028 |

*Streams a, b, c, and d are shown in FIG. 3. Streams a, b, and d are measured, whereas c is calculated by difference.

The membrane modules were run at constant inlet pressure, with the inlet permeate flow rate being controlled by a second pump that passed water through the permeate side of the HF membrane module at flow rates indicated in Table 10 (refer to flow column c). The permeate flow rate was used to sweep away the fluid that penetrated the HF wall, consequently causing the outlet flow (on the permeate side) to be higher than the inlet flow. The height of a layer of particles on the membrane surface increases with increasing transmembrane pressure for 1.5μ silica spheres in water. This motivated us to introduce flow of water on the permeate side to decrease transmembrane pressure drop below what it would be if there were no sweep fluid in the permeate side.

Effects of optimization of enzyme treatment were measured in terms of cell viability before and after enzyme addition. The effect of protease on *Salmonella* viability was determined by incubating *Salmonella* with enzyme for 0, 10, 20, and 30 min. Protease was added to aqueous chicken homogenates at 0.5% (v/v) (or 0.27 mg/mL), followed by inoculation of *Salmonella* to give a final concentration of 103 CFU/mL. Six different conditions were tested. Conditions 1 and 2 consisted of *Salmonella* inoculated in aqueous chicken homogenates with and without addition of protease; 3 and 4 were *Salmonella* inoculated in BPW with and without addition of protease; and 5 and 6 were *Salmonella* min. The supernatant was used for DNA templates. For the second procedure, DNA was isolated using a commercially available kit (QIAamp DNA Mini Kit, Qiagen, Venlo, Netherlands). Amplification reactions were performed in a final volume of 20 μL containing 2 μL of bacterial DNA, 200 μmol deoxynucleotide mix (Sigma-Aldrich, St. Louis, MO), standard Taq reaction buffer (New England Biolabs, Ipswich, MA; final concentration: 50 mM KCl, 10 mM Tris pH 9.0, 0.1% triton X-100, 2 mM $MgCl_2$), 1.5 units of Taq polymerase (New England Biolabs), and 5 pmol each of the forward and reverse primers. The following primer sets were used to target the hilA and hisJ genes: hilA forward: 50-CTGCCGCAGTGTTAAGGATA-30 (SEQ ID NO: 3), hilA reverse: 50-GTCGCCTTAATCGCATGG-30 (SEQ ID NO: 4), hisJ forward: 50-ACTGGCGT-TATCCCTTTCTCTGGTG-30 (SEQ ID NO: 5), hisJ reverse: 50-GTTGTCCTGCCCCTGGTAAGAGA-30 (SEQ ID NO: 6). PCR amplification was carried out using a thermal cycler (MyCycler Thermocycler, Bio-Rad, Hercules, CA) with temperature cycling as follows: 95° C. for 1 min, followed by 35 cycles at 94° C. for 30 s, 62° C. for 30 s, 72° C. for 30 s, and a final extension step at 72° C. for 2 min, for a total time of 124 min. A negative control was also performed that included the same reaction mixture except that the DNA template was replaced with water. Amplification products were resolved by electrophoresis on a 2.0% (w/v) agarose gel and visualized using ethidium bromide staining and a UV transilluminator.

One-way analysis of variance at the 95% confidence level was performed using MinitabVR 17. Post hoc comparisons by Tukey's test determined the significance of differences in bacterial cell counts in the absence or presence of added protease. Experiments were done at least in triplicate, and data expressed as their average and corresponding standard deviation. Results are shown as error bars in the appropriate figures.

Results

Figure 33:
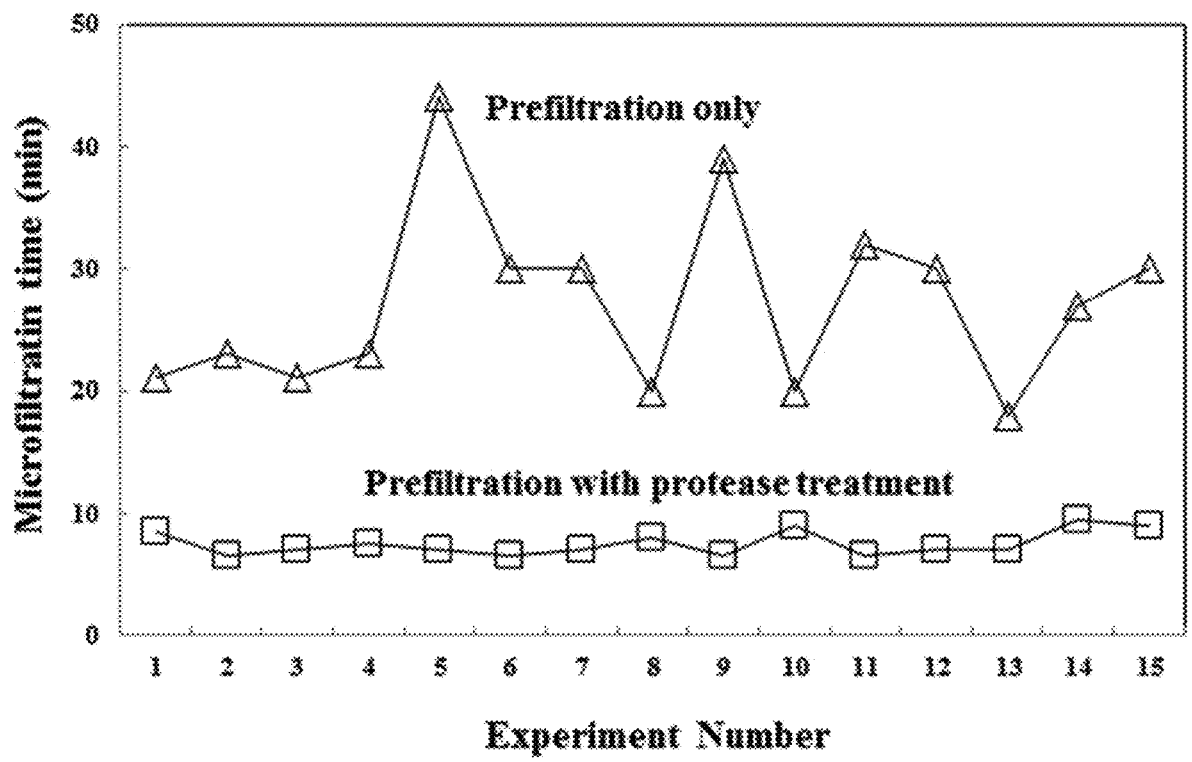
FIG. 33 shows variability in microfiltration times for filtered aqueous chicken homogenates, either pretreated or not pretreated with 0.5% (v/v) protease (at 37° C. and stomached 200 rpm for 30 min). Runs carried out using the 12 fiber modules.

Initial results showed that microfiltration of 50 mL of extract from chicken legs in 8 min was about a third of the time needed to microfilter untreated extract to which enzyme had not been added when the 12 fiber module was used. These experiments also showed that endopeptidase (protease) decreased filtration time more than that with lysophospholipase (lipase), whereas combined protease and lipase gave the same microfiltration rate as endopeptidase alone. Protein was, therefore, indicated as a primary cause of fouling. Subsequent runs confirmed that enzyme treatment reduced the time required for the microfiltration step, and the previously reported cleaning procedure facilitated re-use of the module for at least 15 samples. Run to run variability as measured using the 12 fiber module was also minimized (refer to bottom line in FIG. 33), whereas major differences in microfiltration times occurred if no enzyme was used (difference between two curves in FIG. 33). However, there was concern about the effect of protease on cell viability, and so further tests were carried out. FIG. 33 shows variability in microfiltration times for filtered aqueous chicken homogenates, either pretreated or not pretreated with 0.5% (v/v) protease (at 37° C. and stomached 200 rpm for 30 min). Runs carried out using the 12 fiber modules.

Figure 34:
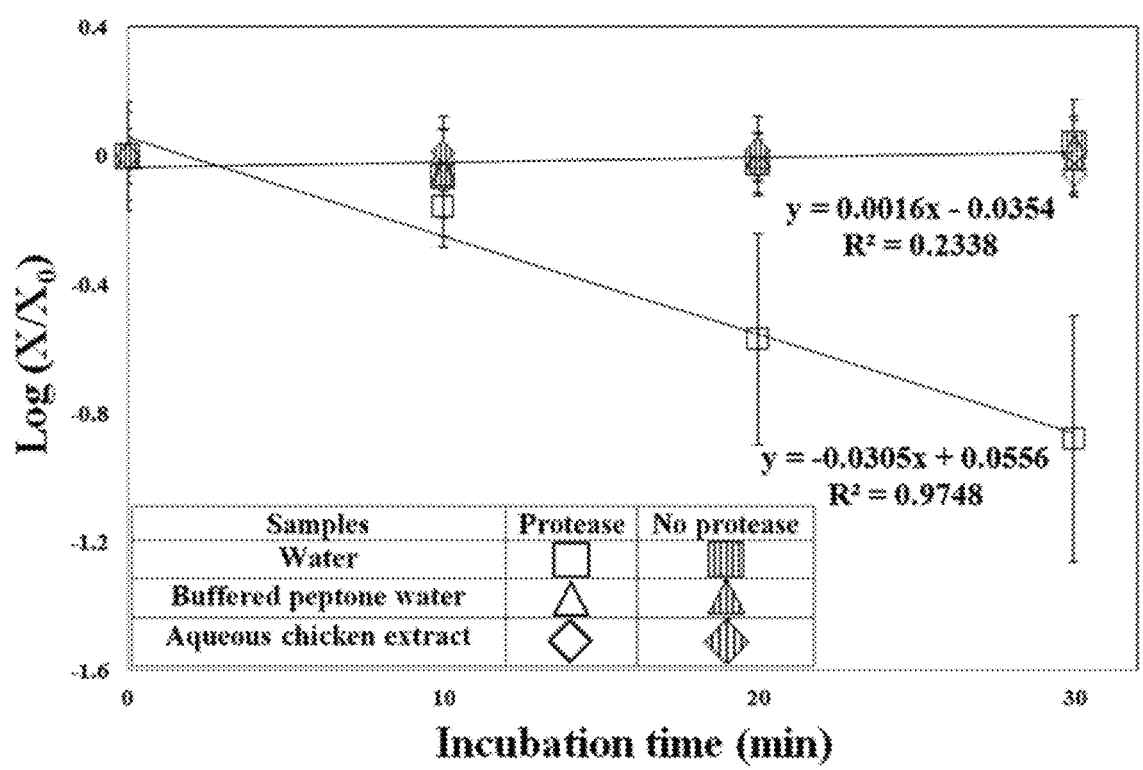
FIG. 34 shows a plot of cell population (*Salmonella*, 103 CFU/mL) growth rate under different experimental conditions.

Salmonella cells are stable when suspended in DI water or incubated with protease in aqueous chicken extracts, BPW, or DI water containing chicken extract. However, 80% viability was lost in 30 min when the cells were suspended with protease in DI water in the absence of protein or peptide (FIG. 34). A protective effect occurs when the protease, viable *Salmonella* cells, and protein are incubated together. An enzyme treatment time of 10 min gave HF microfiltration rates of 6.6+/−0.8 mL/min, equivalent to microfiltration of 50 mL of enzyme-treated extract in 8 min. These rates were the same for enzyme incubation times of 10, 20, and 30 min when protein was present. Retention of cell viability was confirmed by culturing of the resulting samples on BHI agar plates and counting the colonies that formed after 24-36 h of incubation at 37° C. The data for cell growth and filtration times of the three solutions were statistically the same based on analysis of variance evaluation. When extract was incubated with protease for more than 30 min, a decrease in viability of the cells in the homogenate compared with the control (no protease added) was found to be statistically significant (FIG. 34). Hence, 30 min was selected as the upper limit of incubation time after protease is added, with 10 min being sufficient to obtain the desired microfiltration and food sample properties. FIG. 34 shows a plot of cell population (*Salmonella*, 103 CFU/mL) growth rate under different experimental conditions. The plotted different conditions include: 1. protease added to aqueous chicken homogenates at 0.5% (v/v), followed by inoculation of *Salmonella*; 2. *Salmonella* inoculated in aqueous chicken homogenates without addition of protease; 3. Protease added to buffered peptone water at 0.5% (v/v), followed by inoculation of *Salmonella*; 4. *Salmonella* inoculated in buffered peptone water without addition of protease; 5. Protease added to DI water at 0.5% (v/v), followed by inoculation of *Salmonella*; 6. *Salmonella* incubated only in the presence of DI water. Data are the average of three assays. Error bars represent standard deviation. Population growth rates at up to 30 min after inoculation are significantly different at the 95% confidence level. A similar pattern was observed when inoculating the cells in chicken carcass rinses.

The required time to process 400 mL of chicken carcass rinse was 2 h using the commercial, 45 fiber PES modules. *Salmonella* growth that occurred within this 2-h time period provided a short enrichment step, and helped to maximize the number of viable cells recovered at the end of the process as well as to bring the numbers to detectable levels (103 CFU/mL). Recovery of viable (living) cells as determined by plating was about 50% of the initial cells measured after prefiltration (Table 11). When this sample was subsequently processed using HF microfiltration, cell recovery during the microfiltration step was 70%, which is consistent with our previous results 7 for homogenates of chicken meat. Overall recovery was 0.5×0.7 or 0.35 (35%), starting with 1-10 CFU/mL.

TABLE 11

Change in CFU *Salmonella* as a function of sample processing for chicken carcass rinse (based on n = 3)

| Step | Elapsed Time (h) | Volume (mL) | Naturally Occurring (CFU/mL) | Spiked (CFU/mL) |
|---|---|---|---|---|
| Rinse | 0 | 400 | ND | ND* |
| Incubation | 3 | 400 | NA† | 67 ± 20 |
| Enzyme treatment | 0.15 | 400 | ND | 77 ± 28 |
| Prefiltration | 0.15 | 396 ± 2.0 | ND | 40 ± 13 |
| C³D | 1.7 | 9.6 ± 2.4 | 31 ± 7 | 1,707 ± 1,363 |
| Centrifugation | 0.15 | 1.0 ± 0.3 | 159 ± 15 | 8,170 ± 3,402 |
| At completion | 5.15 | 1 | 159 ± 15 | 8,170 ± 3,402 |

*Spiked at a level equivalent to 5 CFU/10 mL of chicken carcass extract.
†A short enrichment step was not done in this case. ND, not detected; NA, not applicable.

Confirming previous reports in the literature, the depth filter (glass microfiber membrane) is efficient in removing potential foulants, but retains significant numbers of microorganisms. A 3-h enrichment step was, therefore, added to precede the 10 min enzyme treatment and subsequent prefiltration. This approach increased the number of cells by a factor of 2 (from 35% to 70%). The total elapsed time for enrichment, enzyme treatment, prefiltration, microfiltration, centrifugation, and cell recovery was 6 h. PCR of the recovered cells required an additional 2 h.

Figure 36:
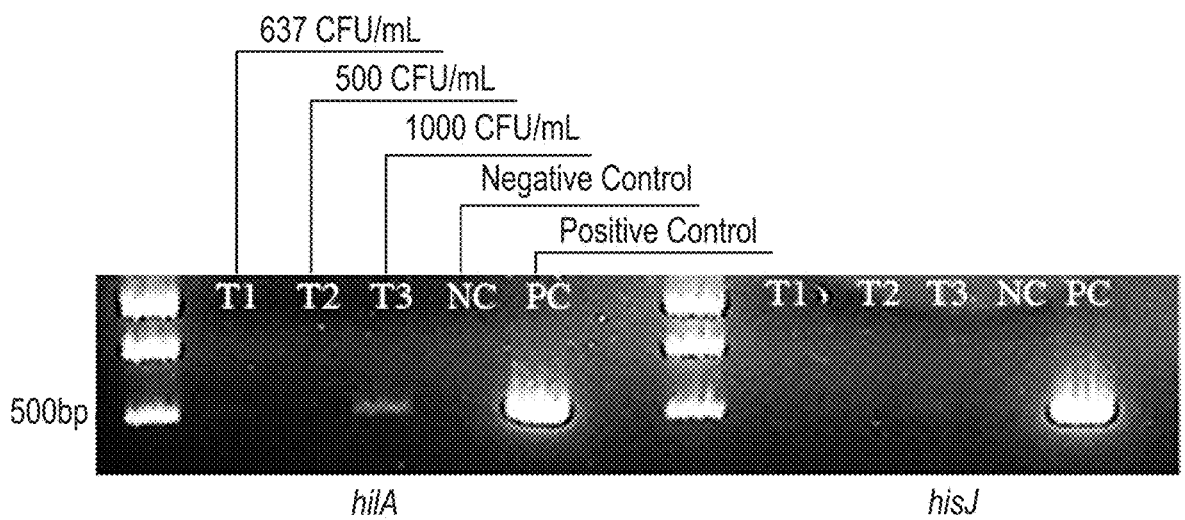
FIG. 36 shows PCR of naturally occurring microbiota showing *Salmonella* from chicken carcass rinse after cell concentration and recovery process with a detection limit of 103 CFU/mL indicated (light band for hilA, sample T3).

PCR requires use of a DNA extraction/recovery kit because simple isolation using microwave to disrupt the cells and release DNA does not remove them. This is shown in FIG. 34, the (a) plot shows where bands were not observed, even when samples S1 through S5 corresponding to the different steps involved in preparing chicken carcass rinse were spiked with 108 CFU *Salmonella*/mL. In contrast, the positive control consisting of buffer and *Salmonella* only gave a strong band. A commercial kit removed PCR inhibitors from the samples as indicated by the 500 bp bands shown in FIG. 34 in the (b) plot for both hilA and hisJ primers. When the commercial kit was used to recover DNA from chicken carcass rinse that had been enzyme treated, microfiltered, and centrifuged, 1,000 CFU Salmonella/mL were detected (light band for T3 with hilA), whereas 500 and 640 CFU/mL were not detected (samples T1 and T2) (FIG. 36). Cell counts were confirmed by plating.

The effects of mechanical pretreatment on food, in this case chicken leg meat, shows that an increased stomaching speed released more protein, but only a small number of additional viable microorganisms (FIG. 31). The decrease in bacterial viability could have several causes: (i) mechanical forces become too great for injured bacteria to recover, (ii) bacterial inhibition agents are released from the animal food matrix, which inhibit bacterial growth, and (iii) bacteria could re-attach to the stomached food matrix as extended times or increased speeds result in finer food particles. Whatever the circumstance, a less severe stomaching condition produced a more desirable result by detaching an increased number of viable microorganisms from the food substrate. Additionally, increasing the time of mechanical pretreatment seems to have a detrimental effect on the number of viable microorganisms present in the chicken homogenate solution.

Another factor is shearing of cells as they pass through a HF. Because the Reynolds number is in the laminar range and vigorous stomaching (shearing for up to 30 min) has little effect on cell viability, cell loss due to shear within the HF is expected to be small.

Naturally occurring *Salmonella* cells present in chicken carcass rinse were also concentrated, recovered, and then detected by plating on XLD agar, but in the absence of an enrichment step. The resulting 0.5-5 mL sample volumes obtained from microfiltration make it practical to use centrifugation in a microfuge to achieve an overall increase in cell count by five times or more. Plating of these samples on XLD agar showed that *Salmonella* increased from nondetectable levels in the initial 400 mL of chicken rinse to 159 CFU/mL after processing the rinse through HF microfiltration and centrifuging the resulting 1 mL sample (Table 11).

Figure 35:
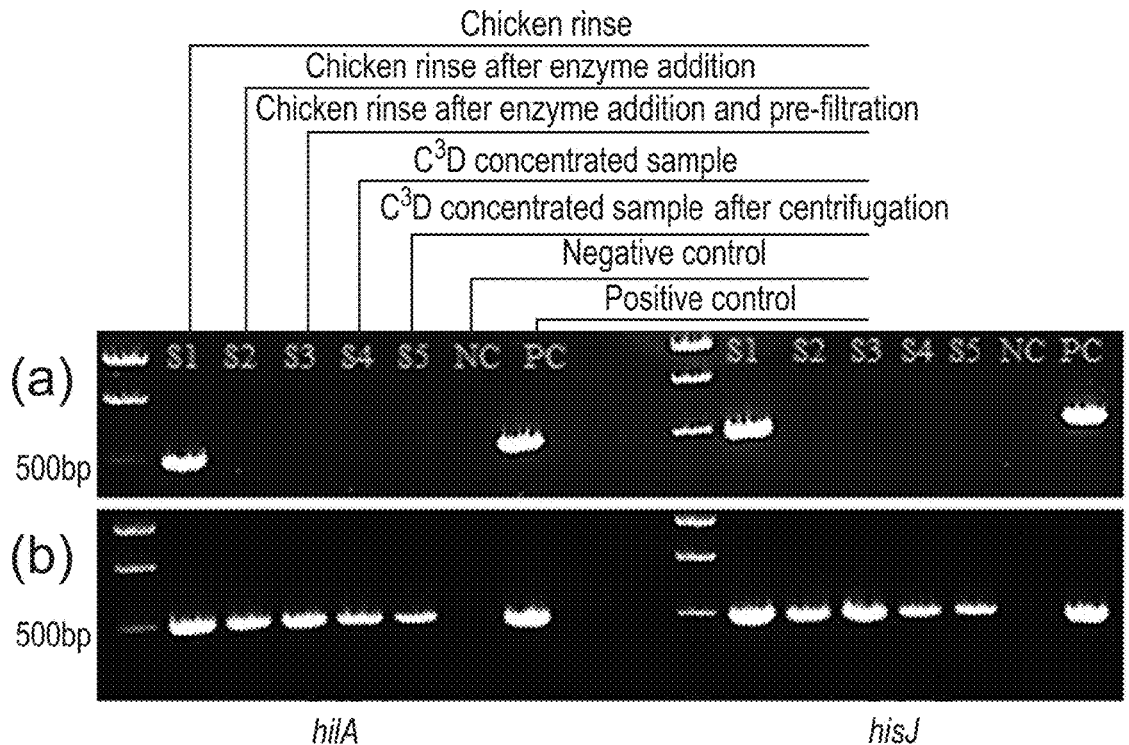
FIG. 35 shows the identification of source of PCR inhibitors and their removal. In panel (a), the upper panel, 108 CFU/mL of *Salmonella* were added (to assure excess number of cells is present for PCR detection) to samples following each of the processing steps. Isolation of DNA was carried out by microwaving the samples. PCR Inhibitors formed during sample processing persist in all the steps. In panel (b), the lower panel, isolation of DNA was carried out using a commercial kit. PCR inhibitors were removed, and DNA amplification targeting *Salmonella* cells was observed in all steps (light bands shown across lower panel). S1 through S5 represent samples from different steps as indicated by labels above the figure. NC is negative control, and PC is positive control. hilA and hisJ are commonly used primer sets for PCR-based identification of *Salmonella*.

PCR inhibitors present in chicken carcass rinses, or poor efficiency during microwave treatment, may cause the absence of bands in samples S1 through S5 for hilA and hist (FIG. 35, plot (a)). Inhibitor removal or higher efficiency may explain the positive results obtained when the commercial DNeasy Blood and Tissue kit was used (FIG. 35, plot (b)).

Microfiltration of samples from food matrices must address the colloidal and soluble components that are released during stomaching and which interfere with the microfiltration process due to fouling and clogging of microfiltration membranes. Although the colloidal matter may be removed by prefiltration, the dissolved protein flows through the prefiltration membrane together with the microorganisms. When followed by microfiltration, the 0.20 μm pores in the HF membranes should be small enough to retain microorganisms and large enough to allow proteins and other smaller components to flow through. In theory, this would leave a more concentrated sample of microorganisms free of smaller soluble components. In practice, a membrane with a relatively large pore size, i.e., 0.20-0.45 μm, does not perform as anticipated because of fouling by proteins that form films at the membrane surface or travel into pores and form aggregates that plug the membrane. As a consequence, flux through the membrane quickly and markedly decreased in the presence of some proteins. This mechanism was originally shown using bovine serum albumin and provides an explanation for phenomena encountered when homogenized (i.e., stomacher) samples are processed by microfiltration.

Figure 37:
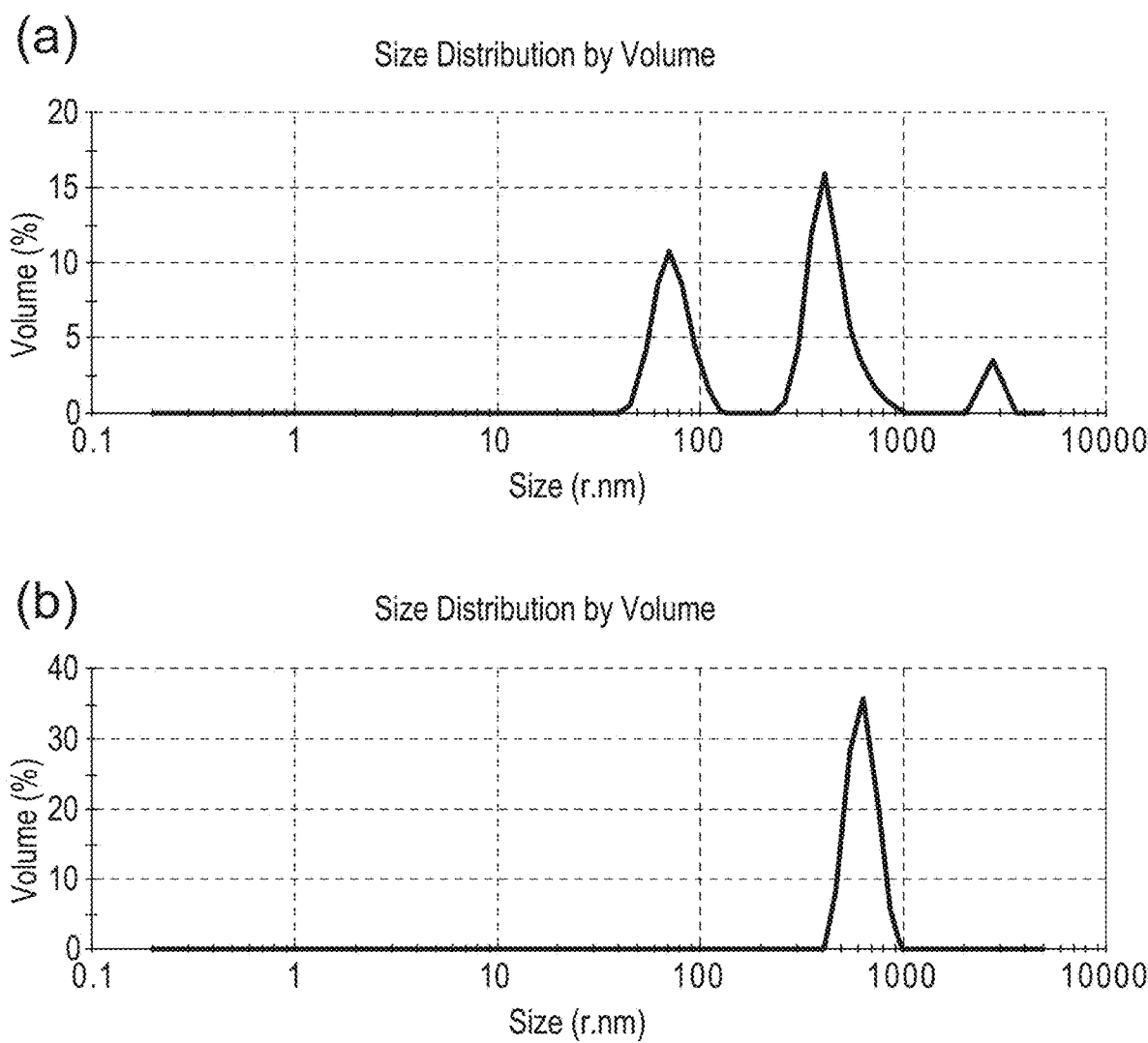
FIG. 37 shows Particle size distribution with (a) untreated and enzyme-treated and (b) prefiltered chicken homogenates.

The particle size distribution analysis of extract from enzyme-treated chicken meat shows that the extract contains 40-4,000 nm particles, prior to microfiltration (FIG. 37). Incubation of artificially spiked *S. enteritidis* PT 21 (103 CFU/mL) for up to 30 min in the presence of protease (0.5% v/v) had no significant reduction in the number of viable microorganisms recovered, although the enzyme consolidated the particle size distribution into the 400-1,000 nm radius range (FIG. 37). FIG. 37 shows Particle size distribution with (a) untreated and enzyme-treated and (b) prefiltered chicken homogenates.

Fouling was confirmed by cutting open a 12-fiber module after being used for five runs to process 250 mL aqueous chicken homogenates, each at a feed flow rate of $3.5\times10^{-7}$ m3/s (21 mL/min) with cleaning the module between runs. The scanning electron microscopy of the inlet, middle, and outlet sections of the HF shows that the new membrane is highly porous (FIG. 38 (a)). After five uses, the most significant layer formation is observed near the inlet of membrane module (FIG. 38 (b)). These results show non-uniform deposition along the membrane. Some deposition occurs near the outlet, whereas the middle section seems relatively free of an adsorbed layer (compare FIG. 38 (a)-(d)). These images are consistent with maximal flux (and therefore build-up of a fouling layer) initially occurring near the inlet, with a different type of deposition near the outlet where flow rate is the lowest.

Figure 38:
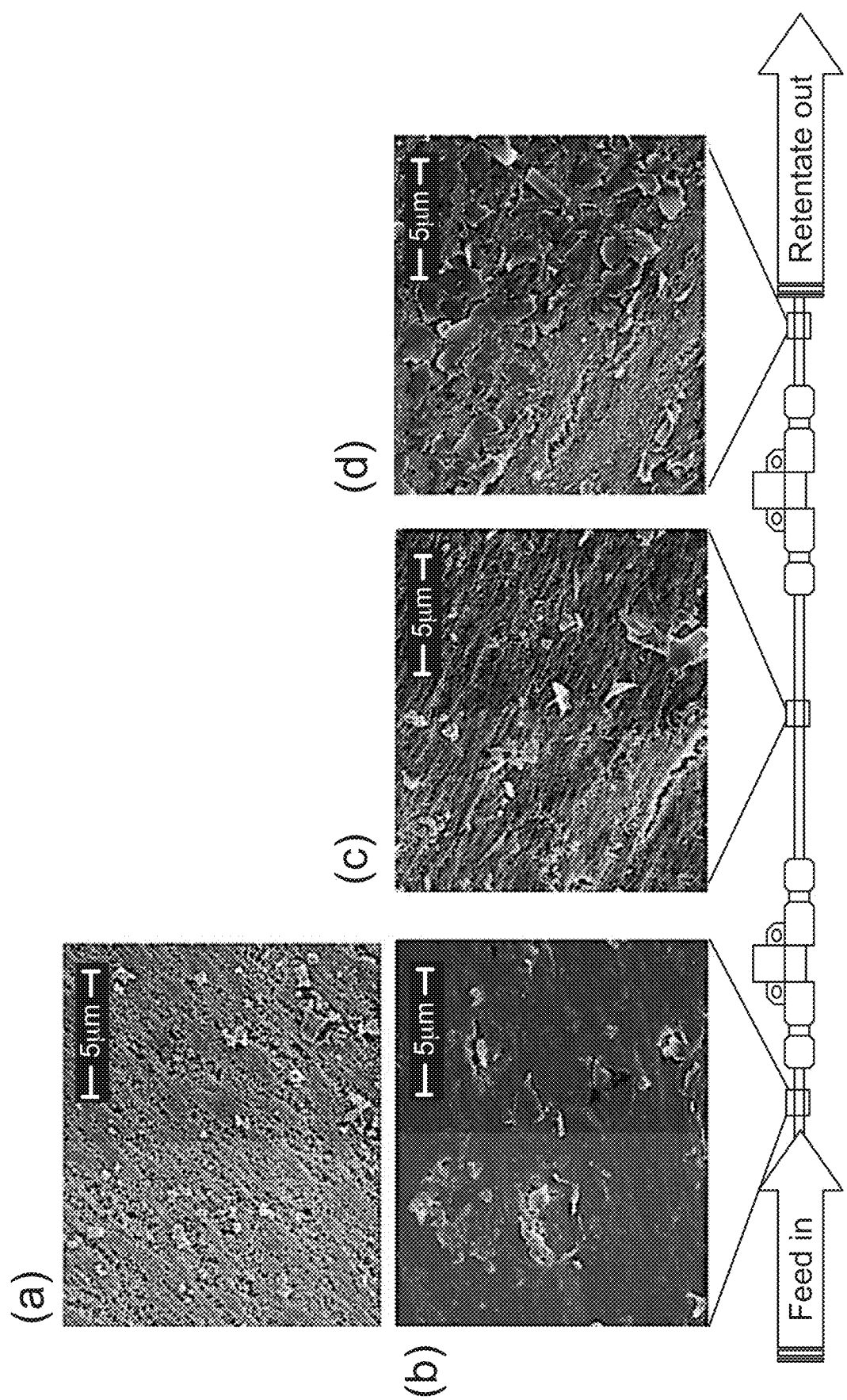
FIG. 38 shows microscopic analysis of (a) the original inner layer of polysulfone membranes taken from the inlet part, and fouled inner layer of polysulfone membranes by chicken homogenates taken from the inlet (b), middle (c), and outlet (d).

FIG. 38 shows microscopic analysis of (a) the original inner layer of polysulfone membranes taken from the inlet part, and fouled inner layer of polysulfone membranes by chicken homogenates taken from the inlet (b), middle (c), and outlet (d).

Microfiltration has been examined over the last 30 years as a way to reduce the time required to obtain a suitably concentrated sample for interrogation by PCR or other detection techniques. Our work determined that the addition of an enzyme treatment step reduces microfiltration time, increases reproducibility, and maintains viability of recovered microorganisms.

We have also shown that addition of endopeptidase modifies soluble protein and colloidal particles in a manner that minimizes fouling while not affecting viability of *Salmonella* when concentrated using cross-flow HF microfiltration membranes. In this work, we reported protocols, combined with the previously described automated system for carrying out microfiltration, where combination of a short enrichment (to bring low cell numbers to detectable levels), preprocessing using enzyme, and concentration gave samples in which *Salmonella* at 1-10 CFU/mL in volumes of 400 mL could be detected within 8 h using PCR. Enzyme treatment of chicken carcass rinses using endopeptidase not only reduces membrane fouling, but also decreases microfiltration time, enhances reproducibility, and enables membrane re-use for at least 15 cycles for a commercially available PES HF module. The decrease in sample volume achieved through microfiltration enables centrifugation to further concentrate *Salmonella* cells at the bottom of a microcentrifuge tube after 5 min of centrifugation.

Example 10

Microfiltration of Enzyme Treated Egg Whites for Accelerated Detection of Viable *Salmonella*: We report detection of less than 13 CFU of *Salmonella* per 25 g egg white within 7 hours by concentrating the bacteria using microfiltration through 0.2 μm cutoff polyethersulfone hollow fiber membranes. A combination of enzyme treatment of the egg white, controlled cross-flow on both sides of the hollow fibers, and media selection were key to controlling membrane fouling so that rapid concentration and the subsequent detection of low numbers of microbial cells were achieved. We leveraged the protective effect of egg white proteins and peptone so that the proteolytic enzymes did not attack the living cells while hydrolyzing the egg white proteins responsible for fouling. The molecular weight of egg white proteins was reduced from about 70 kDa to 15 kDa during hydrolysis. This enabled a 50 fold concentration of the cells when a volume of 525 mL of peptone and egg white, containing 13 CFU of *Salmonella*, was decreased to a 10 mL volume in 50 min. A 10 min microcentrifugation step further concentrated the viable *Salmonella* cells by 10×. The final cell recovery exceeded 100%, indicating that microbial growth occurred during the 3 hour processing time. The experiments leading to rapid concentration, recovery, and detection provided further insights on the nature of membrane fouling enabling fouling effects to be mitigated. The developed protocols also allowed the hollow fiber modules, when sterilized between runs, to be reused at least 20 times, thereby decreasing cost of microfiltration on a per sample basis. Unlike most membrane processes where protein recovery is the goal, recovery of viable microorganisms for pathogen detection is the key measure of success, with modification of cell-free proteins being both acceptable and required to achieve rapid microfiltration of viable microorganisms.

Materials and Methods

*Salmonella enterica* serovar *enteritidis* was incubated overnight in 5 mL of BBL™ brain heart infusion (BHI, Sparks, Baltimore, MD) broth at 37° C., in a G24 environmental incubator shaker at 200 rpm (New Brunswick Scientific Co., Inc., Enfield, CT).

The standard ISO 6579:2002 method (Microbiology of food and animal feed stuffs: Horizontal method for the detection of *Salmonella* spp) was modified by increasing the buffered peptone water (BPW) from 225 mL to 500 mL and substituting a Kenmore® Model Power 10 blender (Sears Holdings, Hoffman Estates, IL) in place of a stomacher. The blender was sterilized between uses by soaking in 10% bleach for 10 minutes and then 70% (v/v) ethanol overnight at room temperature. Fresh grade A shell eggs were purchased from a local grocery store (West Lafayette, IN). Four fresh shell whole eggs (grade A) were soaked in 70% (v/v) ethanol for 30 minutes at room temperature and air-dried in a sterile hood to prevent sample contamination before they were broken. Shells were broken using a sterile spoon and placed in the sterile blender. After removing the egg yolk using a sterile spoon, 100 g of egg whites were homogenized in a blender for 15 seconds, and then artificially spiked with *Salmonella Enteritidis* to obtain an initial level of about 13 CFU/25 g egg whites. The aqueous egg white homogenates were then prepared by mixing 25 g of homogenized egg whites and 500 mL of buffered peptone water (BPW) (pH 6.9±0.2). The procedure is summarized in FIG. 39.

Figure 39:
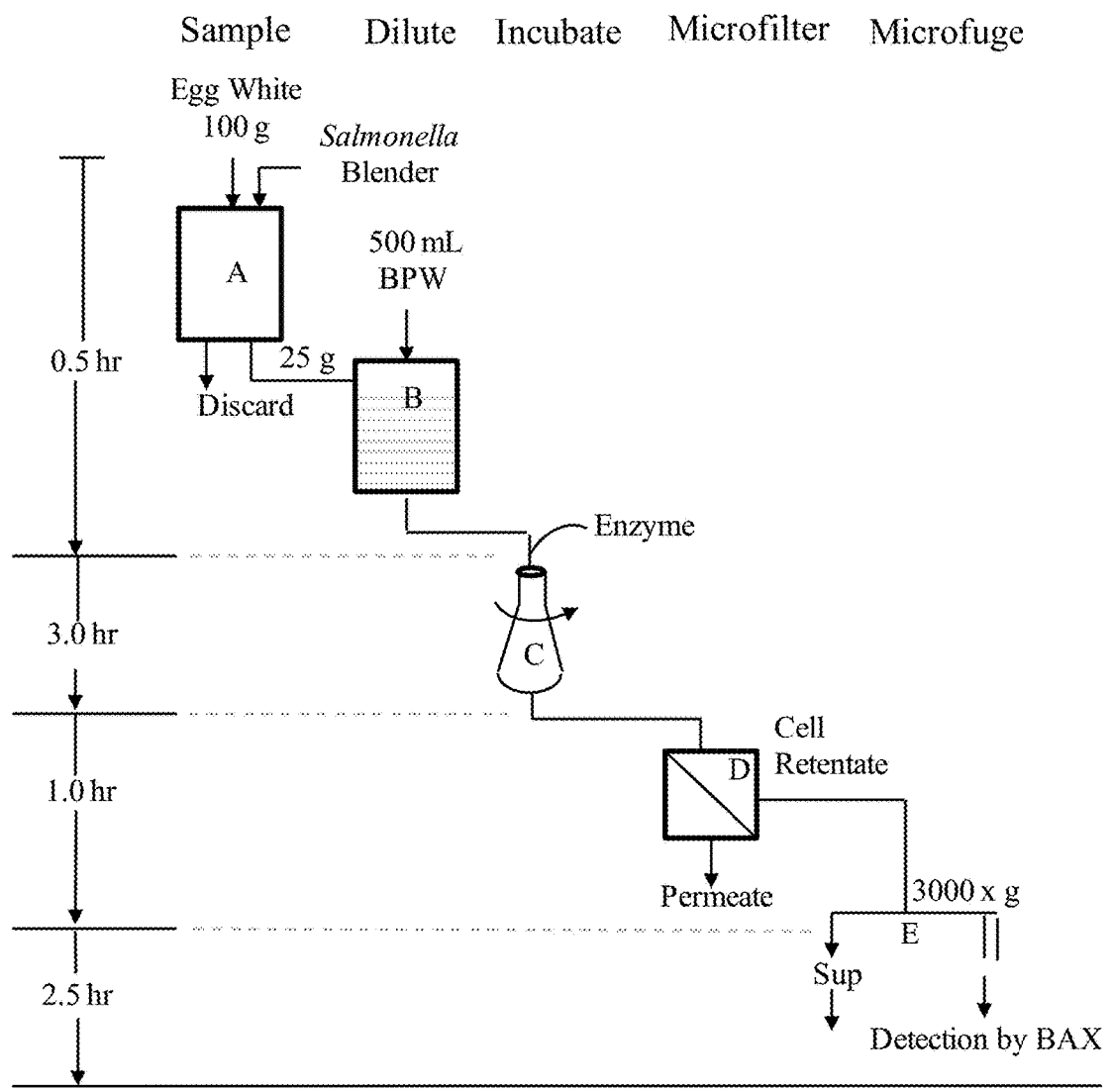
FIG. 39 shows a Schematic representation for *Salmonella* concentration and recovery from egg white homogenates.

FIG. 39 shows a Schematic representation for *Salmonella* concentration and recovery from egg white homogenates. A: Spiking *Salmonella* into 100 g of egg whites and collecting 25 g of egg whites after homogenizing by blender for 15 sec; B: Mixing 500 mL of buffered peptone water with 25 g of egg whites and proteolytic enzymes resulting in egg white homogenate; C: Simultaneous hydrolysis and enrichment at 37° C.; D: Microfiltration using automated system; E: Centrifugation for further sample concentration followed by *Salmonella* detection using BAX.

Inappropriate sampling may result in false negatives. Therefore, the collected sample should represent the original food material as exactly as possible.[26] In the classical protocols, stomaching or rinsing has been used to extract microorganisms from the surface of food samples. However, for cases of egg contamination, *Salmonella* can swim and move inside egg whites. Therefore, we used mechanical blending of the separated egg white to obtain a homogeneous mixture of both interior and surface pathogens.

Protex™ 7 L was provided by Genencor Division of Danisco (Rochester, NY), and Promod™ 298 L was purchased from Biocatalysts Ltd. (Wales, UK). Both Protex™ 7 L and Promod™ 298 L are proteolytic enzymes extracted from *Bacillus* species. Protein concentrations of stock solutions of Protex™ 7 L and Promod™ 298 L were 39.6 mg/mL and 42.4 mg/mL, respectively, and activities were 1,600 AU/g and 150 AU/g, respectively. The concentration of protein in the commercial enzymes was determined by the Pierce (Thermo Scientific, Rockford, IL) bicinchoninic acid protein assay based on manufacturer's instructions. Based on manufacturer data the optimal temperature for Protex™ 7 L was between 40 to 60° C. and for Promod™ 298 L 50 to 65° C. with optimal pH for both enzymes between 6.8 to 8.0.

The effect of protease on *Salmonella* viability was determined by incubating the microorganism in the presence of the enzyme for 2 hours at 37° C. under different experimental conditions. Enzymes were added to the egg white homogenates at 0.2 mg/mL respectively for 2 hours, after inoculation of *Salmonella* at 102 CFU/mL. During the enzyme incubation period, the homogenates were collected and plated. The doubling time for *Salmonella* was estimated using the equation $t_d = t/(3.3(\log X/X_0))$ where $t_d$ is the doubling time, t is the time period of cell growth, X is the number of *Salmonella* at time t, $X_0$ is the number of *Salmonella* at the starting time. Cell colonies were counted after 20 hours.

The food homogenates were concentrated by microfiltration using a commercial hollow fiber module consisting of 45 polyethersulfone fibers with a pore cut-off of 0.2 m, 0.50 mm inner diameter and 20 cm length fibers with 3.14 cm² fiber surface area per fiber for a total of 140 cm² surface area per module (Spectrum Laboratories, Inc., catalog D02-P20U-05-N, Rancho Dominguez, CA). The hollow fiber module was integrated into an automated instrument developed in our laboratory to enable rapid microfiltration of food extracts containing viable microorganisms. The sequence preceding hollow fiber microfiltration (FIG. 39) evolved from research with rinses and with homogenized (stomached) chicken meat.

Xylose lysine deoxycholate (XLD) agar (VWR, Batavia, IL) was used as the selective medium for enumeration of *Salmonella*. Two different sizes of petri dishes were used to determine the number of viable cells. Aliquots of 100 μL of aqueous egg white homogenates in addition to concentrated and recovered samples were spread on the 100×15 mm petri dishes (VWR, Catalog No. 25384-094, Batavia, IL). For blended egg whites, 1 g was spread on 150×15 mm petri dishes (VWR, Catalog No. 25384-326, Batavia, IL) to count cell numbers initially present. For all experiments, colonies were plated on XLD and counted after 20 h of incubation at 37° C.

Figure 40:
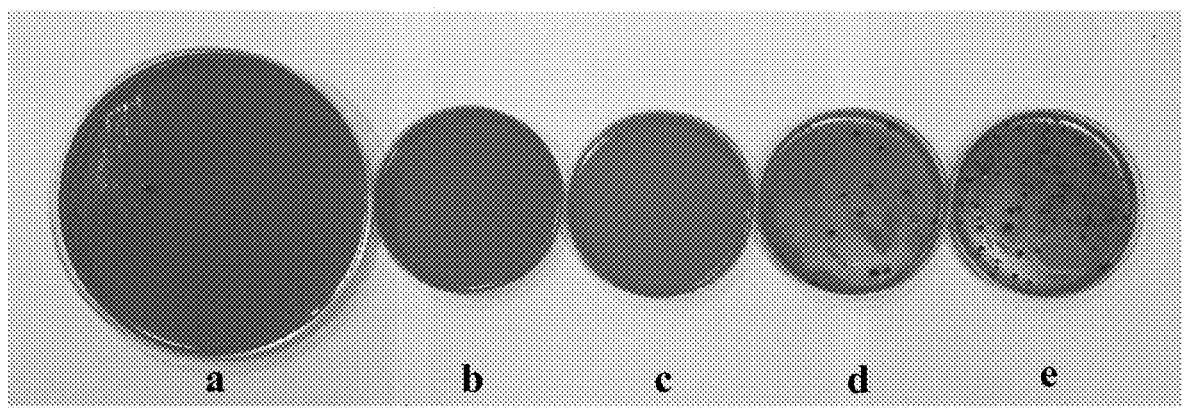
FIG. 40 shows Plating 1 g of sample on XLD media to enumerate an initial microbial concentration.

The 5 steps between sampling and PCR are summarized in the graphic shown in FIG. 39. In the first step, 100 g egg whites were spiked with *Salmonella* and homogenized using a sterilized blender (FIG. 39, step A). After blending, 1 g (1000 μL) of egg white was collected and spread onto 150×15 mm sized XLD plates (FIG. 40, a). The initial count of viable microorganisms was less than about 13 CFU/25 g egg white (i.e., 0.5 CFU/g). The large diameter plate was necessitated by the low level of microorganisms in the sample and the need to use a relatively large volumetric sample (1000 μL) to detect these. From the blender 25 g of egg whites were collected and mixed in 500 mL of BPW containing 0.2 mg/mL of Promod 298L (FIG. 39, step B). 100 μL samples were collected and spread on to 100×15 mm sized XLD plates; (FIG. 40, b). After 3 hours of incubation with enzyme (FIG. 39, step C) 100 μL samples of the BPW from step C were plated on to 100×15 mm sized XLD plates (FIG. 40, c). The initial 525 mL sample was decreased to 10 mL final retentate volume using the microfiltration process (FIG. 39, step D). 100 μL samples were collected again and spread on to 100×15 mm sized XLD plates to enumerate cell concentration (FIG. 40, d).

FIG. 40 shows Plating 1 g of sample on XLD media to enumerate an initial microbial concentration; (a) on a 150×15 mm sized mm petri dish. Plating 100 μL sample on XLD media to enumerate microbial concentrations at selected steps on 100×15 mm sized petri dishes after each of the steps (b) after step B; (c) after step C; (d) after step D; (e) after step E. The red color of the agar is from the XLD media. Black dots in D and E are due to growth of *Salmonella* after 20 hours of incubation, with samples obtained from steps D and E, respectively.

Once the volume is decreased from 525 mL to 10 mL using hollow fiber microfiltration, the volume is small enough so that microcentrifugation in a set of 1.5 mL tubes is possible (FIG. 39, step E). After 10 min microcentrifugation at 14,000 rpm [20,800×g (centrifuge 5418, Eppendorf, Hamburg, Germany)], the supernatant was decanted and 600 μL of sterile phosphate buffered saline (PBS; 137 mM NaCl, 4.3 mM Na2HPO$_4$, 2.7 mM KCl, 1.47 mM KH$_2$PO$_4$, pH 7.4) was added to resulting pellet and remaining fluid that contained microbial cells. The final volume was about 1 mL (FIG. 38, step E). From this liquid, 100 μL samples were collected and spread on to 100×15 mm sized XLD plates to check the change in cell concentration after step E (FIG. 38, corresponding plate in FIG. 40(*e*)).

Microfiltration of 525 mL egg white sample containing *Salmonella* cells enabled examination of membrane properties based on measurements of permeate flux and permeate and retentate side pressures at 100 second intervals. The instrument was programmed with an automated cleaning and sterilization cycle that followed microfiltration. After sterilization, the entire system was prepared for re-use by circulating volumes of 65 mL of 0.2 M sodium hydroxide, 70% (v/v) ethanol, and sterilized DI water. This protocol enabled 23 reuses of the hollow fiber membrane module.

BAX® System PCR Assay (Qualicon DuPont, Wilmington, DE) and conventional PCR were used for rapid *Salmonella* detection from the concentrated samples (follows step E in FIG. 39). BAX® System PCR Assay was performed by the manufacturer's instructions. Conventional PCR experiments for invA (284 bp) gene fragment amplification were carried out using methods reported earlier.[12] The following primer sets were used to target the invA gene: invA forward (5'-GTGAAATTATCGCCACGTTCGGGCAA-3' SEQ ID NO: 1), and invA reverse (5'-TCATCGCACCGTCAAAGGAACC-3' SEQ ID NO: 2).

All the samples were prepared by mixing Laemmli Sample Buffer (Bio-Rad, Catalog No. 161-0737, Hercules, CA) with 5% (v/v) of 2-mercaptoethanol (Bio-Rad, Catalog No. 161-0710, Hercules, CA) and heating at 95° C. for 5 minutes based on provided instructions (Bio-Rad, Hercules, CA). Sodium Dodecyl Sulfate Polyacrylamide Gel Electrophoresis (SDS-PAGE) was performed by loading 10 μL samples containing 0.5 to 17 μg protein on 12% Mini-PROTEAN® TGX™ Precast Gels (Bio-Rad, Catalog No. 456-1044, Hercules, CA). Gels were stained for 2 hours in Coomassie Brilliant Blue R-250 Staining Solution (Bio-Rad, Catalog No. 161-0436, Hercules, CA), and de-stained in Coomassie Blue R-250 de-staining solution (methanol:acetic acid:DI water=4:1:5).

For statistical evaluation of cell growth activities over the enzyme incubation process, an ANOVA test was performed using Minitab® 16. This was followed by post hoc comparisons using Tukey's test. To analyze differences in microfiltration times from the enzyme treated egg white homogenates and BPW groups, the two sample t-test method was performed using Microsoft® Excel 2013. Regression analysis using Minitab® 16 was applied to counts of initially spiked cell numbers in egg white and to the recovered cell numbers (bacilli of *Salmonella*) from centrifugation of the microfiltered solution (FIG. 39, step E). Statistical significance was determined at $p<0.05$ with three to eight experiments carried out at each condition.

Results and Discussion

After incubation for 3 hours, plating of 100 μL of the BPW sample from step B in FIG. 39 on a 100 mm plate gave the result shown in FIG. 40. Plates b and c in FIG. 40 spread with 100 μL samples after dilution with BPW (FIG. 39, step B), and mixing and incubation with enzyme (FIG. 39, step C), respectively, did not show viable microorganisms after 20 hours of incubation even though they are present as shown in the subsequent microfiltration and centrifugation (FIG. 39, steps D and E) (FIG. 40*s d* and *e*). This reflects the low concentration of viable microorganisms in the egg white suspended in the 500 mL of BPW.

At a level of 13 CFU/525 mL of egg white homogenates, detection would require plating of more than 40 samples, if 1 mL of sample were used to streak each plate. This is avoided by reducing the initial 525 mL volume to 10 mL final retentate using the cross flow microfiltration system. In this case, initially 13 CFU of microorganisms were concentrated into a volume of 10 mL. This results in detectable colonies when <10 samples are plated on XLD media (FIG. 40, d). Once the volume is reduced from 525 mL to 10 mL using microfiltration (FIG. 39, step D) subsequent microcentrifugation in a 1.5 mL tube was possible, so that 14,000 rpm (20800×g) for 10 min results in concentration of *Salmonella* to a detectable level using PCR (FIG. 39, step E). As confirmed by plating (FIG. 40, e), the protease enzyme did not kill *Salmonella* which we attribute to the decoy effect of the egg white proteins. This is an important result since hydrolysis of egg white proteins resulted in stable pressure drops during microfiltration of 525 mL BPW/egg white solutions. In comparison, untreated egg whites in BPW showed an increased pressure drop and decreased flux with increasing microfiltration time (FIG. 41).

FIG. 41 shows (A) Pressure drop as a function of time during microfiltration process at room temperature. Enzyme hydrolyzed group (Δ) (n=5) and untreated group (□) (n=3). (B) Permeate flux as a function of time during microfiltration process at room temperature. Permeate flux of enzyme hydrolyzed group (Δ) (n=5) and untreated group (□) (n=3).

Treatment of egg whites with proteolytic enzymes hydrolyzed the proteins to low MW fragments and thereby minimized the fouling effects of these proteins during microfiltration. The addition of protease to egg whites hydrolyzed the ovalbumin, ovotransferrin, and lysozyme (FIG. 2, lane 2) to low MW fragments (FIG. 2, lane 3), after incubation at room temperature for 2 hours. Enzyme treatment also changed the color and decreased turbidity (FIG. 1). Subsequent microfiltration tests showed a decrease in flux was avoided and repeated microfiltration runs were possible, while at the same time, the number of viable microorganisms increased showing how inactivation of bacteria by proteolytic enzymes is avoided.

Figure 42:
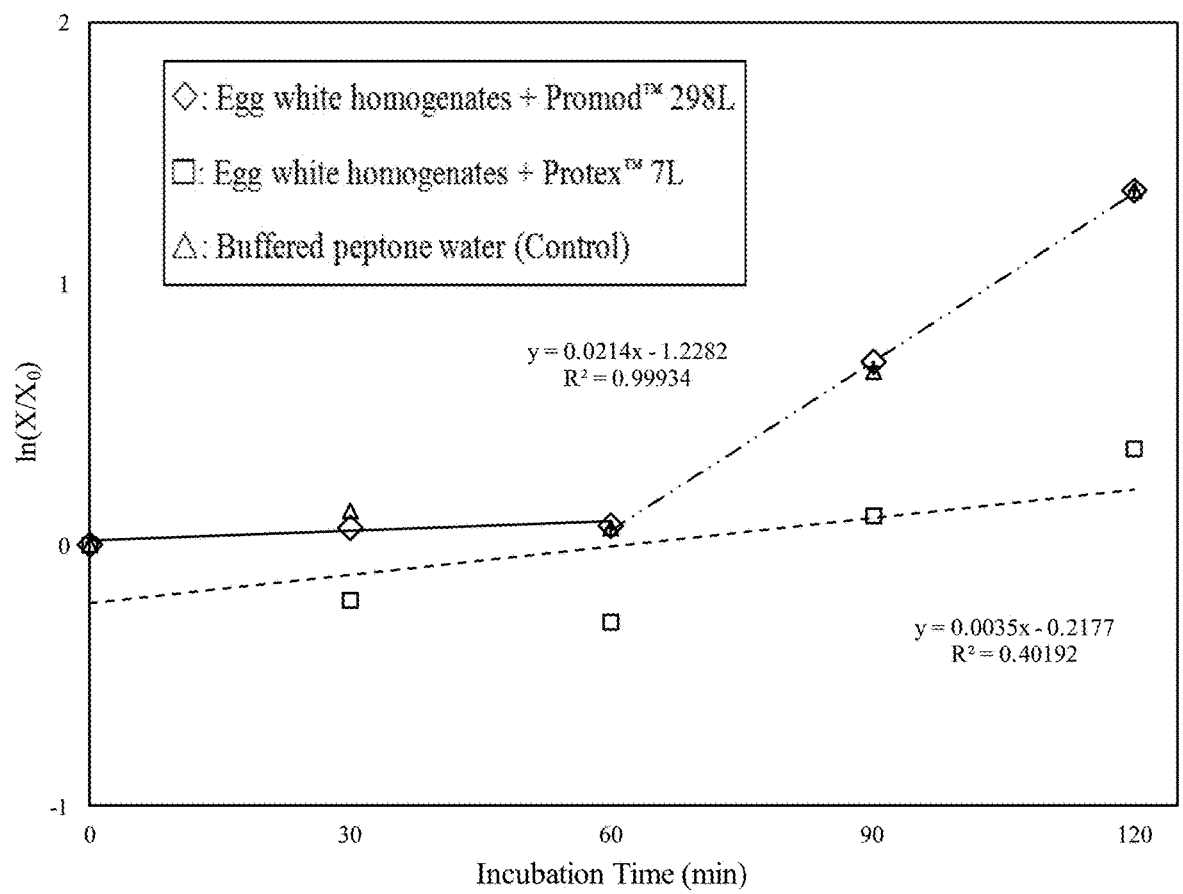
FIG. 42 shows a plot of cell population (*Salmonella*, 103 CFU/mL) growth rate when inoculated with 0.2 mg/mL of Promod™ 298L (◇), 0.2 mg/mL of Protex™ 7L (□), or without enzyme as control group (Δ) in egg white homogenates.

A comparison of the enzyme effects on the growth of *Salmonella Enteritidis* was carried out using Protex™ 7L (0.2 mg/mL) and Promod™ 298L (0.2 mg/mL) (treatment for a period of 2 h (FIG. 42). FIG. 42 shows a plot of cell population (*Salmonella*, 103 CFU/mL) growth rate when inoculated with 0.2 mg/mL of Promod 298L (◇), 0.2 mg/mL of Protex™ 7L (□), or without enzyme as control group (Δ) in egg white homogenates. Data are the average of three replicates. Error bars represent standard deviation. Our results showed that cell growth activities of the three different incubations were not significantly different at up to 60 minutes. However, from 90 to 120 minutes, the samples treated with Protex™ 7L had significantly slower growth rates of *Salmonella* ($P<0.05$) at incubation times between 60 and 120 min compared to the microorganisms in BPW or in BPW with Promod 298L. Protex™ 7L can had a negative impact on cell growth when incubation times were more than 1 hour. The statistical analysis using an ANOVA shows no significant differences in the average cell growth between the control group (BPW) and Promod™ 298L group ($P>0.05$) treated with enzyme for 2 hours. These results were explained by different optimal temperatures and specific activities of enzymes. The specific activity of Protex™ 7 L was about 10 times higher than Promod™ 298 L and the optimal temperature for Protex™ 7 L is about 37° C. Since Promod 298L was effective, we utilized this enzyme in subsequent runs.

The pressure drop across a membrane module and the permeate flux are the key indicators of microfiltration membrane fouling. During the microfiltration process, the pressure drop gradually increased and flux gradually decreased due to the presence of proteins. Here microfiltration of enzyme treated egg white homogenates was completed within 60 minutes with a permeate flux of 41.9±0.9 L/h·m$^2$ and a pressure drop of 30.3±0.7 kPa. This microfiltration time (<60 minutes) did not show statistically significant differences compared to the processing time for 525 mL of egg white-free BPW ($P>0.05$). However, microfiltration of samples that had not been treated with enzymes could not be completed due to the clogging of the hollow fiber membrane.

Clogging of filter pores by BSA can be caused by the accumulation and sedimentation of denatured protein particulates, which provides a nucleation site for attachment of other proteins and accumulation due to formation of intermolecular covalent bonds between sulfhydryl groups. With four free sulfhydryl groups, ovalbumin formed more intermolecular disulfide bonds than BSA with only one free sulfhydryl group. Lysozyme does not have free sulfhydryl groups. Hence, ovalbumin showed the highest decrease in flux compared to lysozyme and BSA. The results in FIG. 41 confirm that Promod™ 298 L treatment of egg white homogenates improves microfiltration by degrading protein components in egg white homogenates that would otherwise aggregate and cause fouling.

Detection of 5.9 CFU *Salmonella* per g egg white and yolk-albumen samples has be achieved in 20 hours when 16 hours enrichment was followed by PCR. Our work was able to detect *Salmonella* at a level equivalent to 13 CFU *Salmonella* per 25 g egg whites in 7 hours when incubation, microfiltration, and centrifugation were followed by BAX® System PCR. The combination of steps A through E, shown in FIG. 39, were completed in 4.5 hours resulting in a 102 to 103 CFU/mL sample. Detection of *Salmonella* by BAX® system PCR was completed in about 2.5 hours with Ct values of 45.7±1 which is within specifications for the instrument (FIG. 43).

Figure 43:
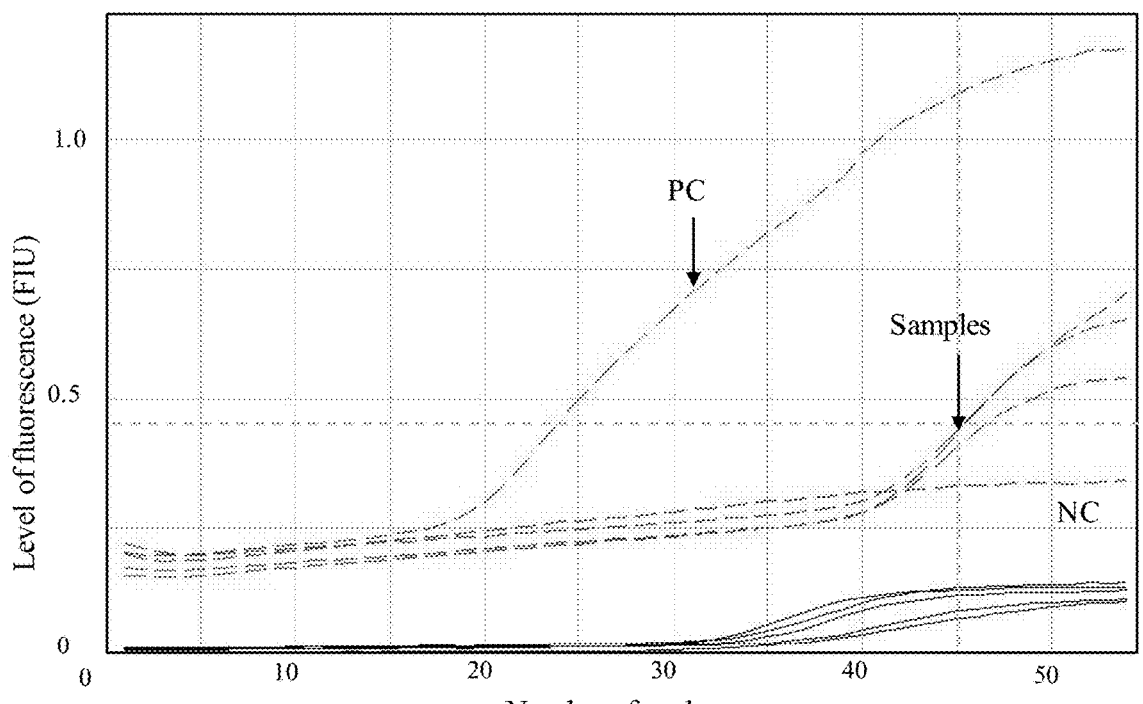
FIG. 43 shows Records of the BAX® System PCR Assay for detection of concentrated *Salmonella*.

FIG. 43 shows Records of the BAX® System PCR Assay for detection of concentrated *Salmonella* (n=3). NC (Negative control; *Salmonella* free egg whites concentrates), PC (Positive control; 108 CFU of *Salmonella* cells). Samples denotes cell concentrate from Step E in FIG. 39. The Ct values for the PC were compared to 31.1 experimental samples of 45.6, 44.7, and 46.7 for egg white samples prepared and processed as given in Materials and Methods.

Figure 44:
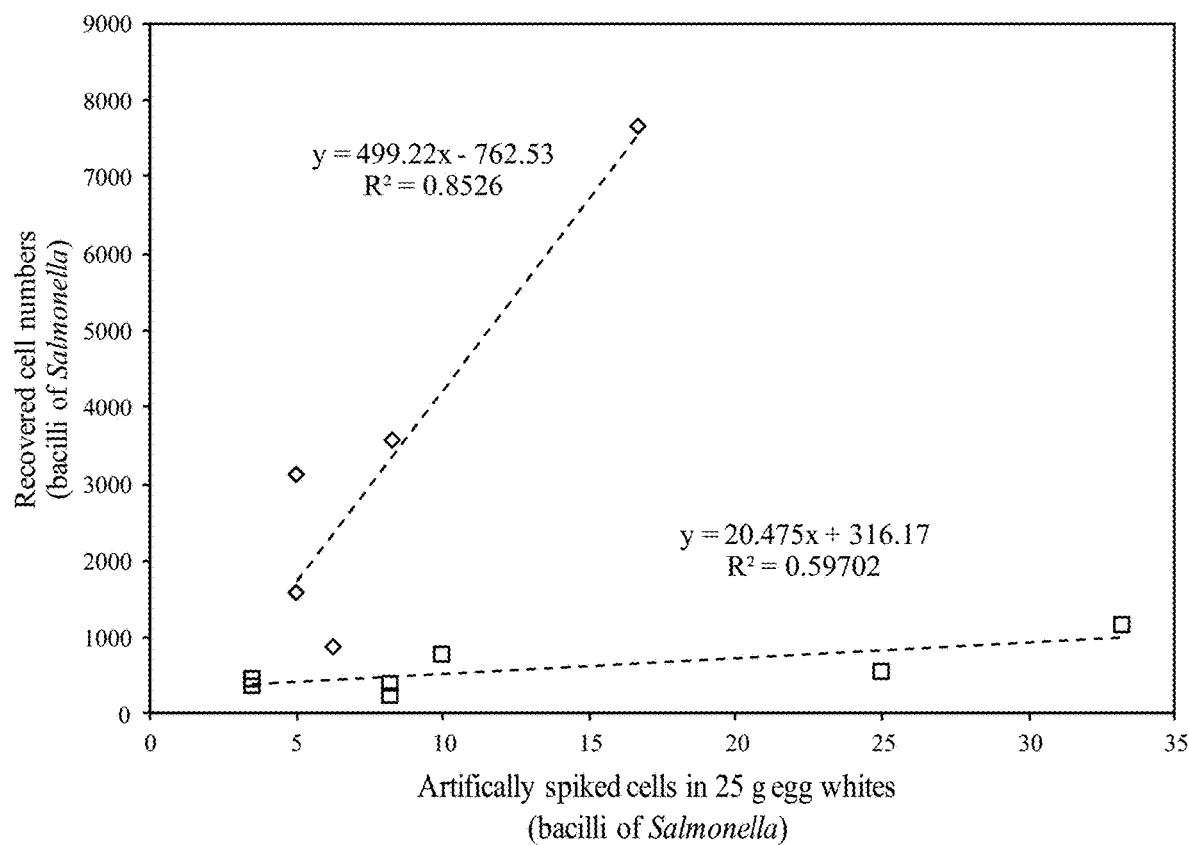
FIG. 44 shows the correlation between the numbers of artificially spiked cells added to 25 g of egg whites and the recovered cells after cell concentration and recovery process.

The detection limit of the combined egg white sampling, preparation, cell concentration, and detection was determined for different levels of *Salmonella* by changing enzyme incubation times. The number of *Salmonella* was enumerated for each process via plating on selective agar media (XLD). The third (n=8) and fourth (n=5) experiments in Table 12 are further described in FIG. 44. FIG. 44 shows the correlation between the numbers of artificially spiked cells added to 25 g of egg whites and the recovered cells after cell concentration and recovery process. The data were plotted after 3 h (□, n=8, p<0.05) or 5 h (◇, n=5, p<0.05) enzyme incubation process. As the number of artificially spiked cells increased, the number of recovered cells increased as well. A positive correlation was present between level of initial inoculum and recovered cell levels. With a P-value of <0.05 indicating our data are statistically significant. However, there were no significant correlation between the level of artificially spiked cells and the number of recovered cells in the 1 h (P>0.05, R2=0.002) and 2 h enzyme hydrolysis groups (P>0.05, R2=0.315). As an enrichment time, one hour cultivation is the middle of lag phase and two hours are very beginning of lag phase (FIG. 42). Therefore, the level of initial inoculum might not significantly affect the recovered amount of cells.

TABLE 12

Concentration and recovery of artificially spiked *Salmonella* in 25 g of egg whites. The *Salmonella* cells were enumerated for each step by plating on selective XLD medium. Data are presented as mean ± standard deviation where the number of samples, n = 5 or 8.

| Experiment | Enzyme hydrolysis time (h) | Cells in egg white (CFU/g) | Cells in egg white homogenates after each processing step | | | |
|---|---|---|---|---|---|---|
| | | | Microfiltration | | Centrifugation | |
| | | | (CFU/mL) | volume (mL) | (CFU/mL) | volume (mL) |
| 1 (n = 5) | 1 | 0.9 ± 0.5 | 7 ± 4 | 8 ± 1 | 66 ± 23 | 0.9 ± 0.4 |
| 2 (n = 5) | 2 | 0.8 ± 0.4 | 41 ± 16 | 8 ± 1 | 299 ± 146 | 1.0 ± 0.5 |
| 3 (n = 8) | 3 | 0.5 ± 0.4 | 87 ± 38 | 9 ± 1 | 559 ± 465 | 1.1 ± 0.3 |
| 4 (n = 5) | 5 | 0.3 ± 0.2 | 441 ± 375 | 11 ± 1 | 3379 ± 2640 | 1.1 ± 0.4 |

Figure 45:
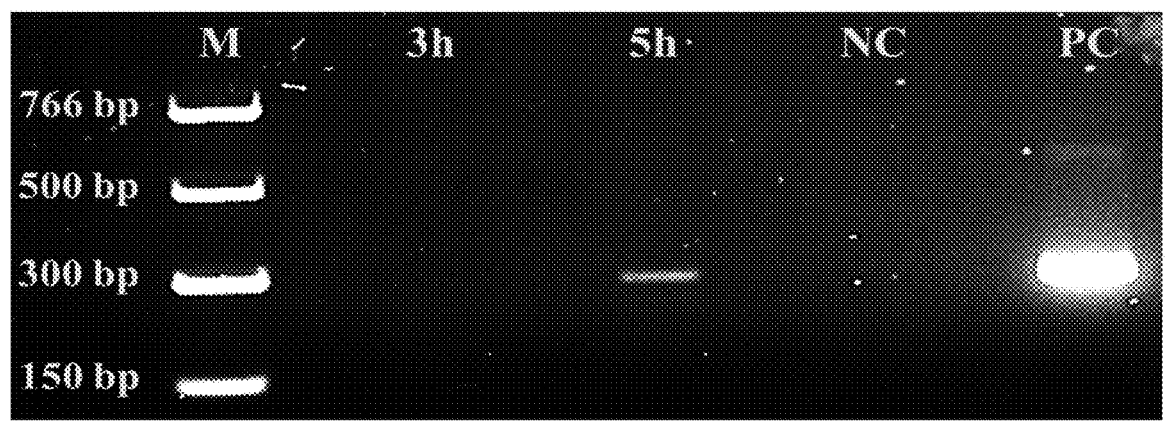
FIG. 45 shows the results of a PCR to determine the minimum enzyme hydrolysis time for rapid *Salmonella* detection.

Multiple researchers reported that when the number of cells are more than 103 CFU/mL, significant bands become visible when they used conventional PCR. Our study supports this result for egg white homogenates incubated with protease for 5 hours (See Experiment 4 in Table 12). The recovered sample showed a positive signal band (invA: 284 bp) as shown in FIG. 45. FIG. 45 shows the results of a PCR to determine the minimum enzyme hydrolysis time for rapid *Salmonella* detection. Samples were the microbial lysate extracted by commercial DNA kit from *Salmonella Enteritidis* after the 3 hour and 5 hour enrichment (enzyme hydrolysis) step. NC (Negative control), PC (Positive control) were the microbial lysate extracted by commercial DNA kit from 108 CFU of *Salmonella Enteritidis*. When the egg white homogenates were incubated with protease for 3 hours (Experiment 3 in Table 12), there was no significant positive signal band indicating the need for additional enrichment if standard PCR is used. In comparison BAX® PCR was able to detect *Salmonella*, since its where sensitivity is greater, resulting in a 2 hr enrichment time saving at these conditions.

This work reported that a combination of microfiltration and short enzyme incubation (3 hours) can replace culture enrichment that requires more than 24 hours. The major impediment of membrane fouling was overcome by treating egg white homogenates with an endopeptidase, Promod™ 298 L. Enzyme treatment increased permeate flux and reduced membrane fouling, while preserving the viability of low levels of *Salmonella*. Promod™ 298 L pretreatment occurred simultaneously with a 3 hour pre-enrichment step during sample processing. This facilitated *Salmonella* growth in egg white homogenates and reduced microfiltration time to less than one hour. This combination resulted in a detectable level of *Salmonella* to be recovered when starting from <0.5 CFU/g in egg whites. Detection of *Salmonella* is achieved within 7 hours from the start of the assay.

What is claimed is:

1. A method for detecting pathogens in food samples, the method comprising:
- obtaining a food sample comprising a pathogen;
- selecting an enzyme;
- treating the food sample comprising the pathogen with the enzyme at a selected concentration in a buffered solution for a period of time, wherein the period of time and the selected concentration are based on the enzyme selected and a known time period and concentration at which point the enzyme impacts cellular viability of the pathogen in the food sample, wherein the period of time and the selected concentration for the treating step optimizes pathogen cell recovery and does not extend past the known time by which the selected enzyme impacts the cellular viability of the pathogen;
- microfiltering the treated food sample using a membrane having a pore size of about 0.2 μm or less;
- centrifuging the microfiltered sample to produce a concentrated food sample; and
- assaying the concentrated food sample for presence of a pathogen,
- wherein the cellular viability of the pathogen is maintained throughout the treating and microfiltering steps.

2. The method of claim 1 wherein the treated food sample comprises a solution.

3. The method of claim 2 further comprising preparing the food sample before the treating step wherein preparing comprises mechanically blending the food sample.

4. The method of claim 3 wherein the prepared food sample comprises coagulated proteins.

5. The method of claim 1 wherein the food sample comprises egg.

6. The method of claim 1 wherein the food sample comprises chicken.

7. The method of claim 1, wherein the food sample comprises spinach.

8. The method of claim 1, wherein the food sample comprises beef.

9. The method of claim 1, wherein the food sample comprises turkey.

10. The method of claim 1, wherein treating the food sample comprises hydrolyzing proteins in the food sample.

11. The method of claim 10, wherein the enzyme comprises is a protease.

12. The method of claim 11 wherein the treating step comprises incubating the food sample with the protease for less than about 90 minutes.

13. The method of claim 1 wherein the enzyme comprises a lipase.

14. The method of claim 1 wherein the assaying step comprises plating the microfiltered food sample on a selective media to detect the pathogen.

15. The method of claim 1 wherein the assaying step comprises a polymerase chain reaction (PCR)-based detection of nucleic acid of the pathogen.

16. The method of claim 1 wherein the pathogen comprises *Salmonella*.

17. The method of claim 1 wherein the pathogen comprises *E. coli*.

18. The method of claim 1 comprising prefiltering the treated food sample prior to the microfiltering step.

19. The method of claim 1 comprising prefiltering the food sample prior to the treating step.

20. The method of claim 1 wherein microfiltering comprises cross flow microfiltration.

21. The method of claim 20 wherein microfiltering comprises concentrating the food sample by passing the food sample through a hollow fiber membrane.

\* \* \* \* \*